US012589161B2

(12) United States Patent
Lam et al.

(10) Patent No.: US 12,589,161 B2
(45) Date of Patent: Mar. 31, 2026

(54) PEGYLATED SYNTHETIC KL4 PEPTIDE, COMPOSITIONS AND METHODS THEREOF

(71) Applicant: THE UNIVERSITY OF HONG KONG, Hong Kong (CN)

(72) Inventors: Ka Wing Lam, Hong Kong (CN); Yingshan Qiu, Hong Kong (CN); Yee Tak Chow, Hong Kong (CN)

(73) Assignee: The University of Hong Kong, Hong Kong (CN)

( * ) Notice: Subject to any disclaimer, the term of this patent is extended or adjusted under 35 U.S.C. 154(b) by 1086 days.

(21) Appl. No.: 17/625,212

(22) PCT Filed: Jul. 10, 2020

(86) PCT No.: PCT/CN2020/101299
§ 371 (c)(1),
(2) Date: Jan. 6, 2022

(87) PCT Pub. No.: WO2021/004524
PCT Pub. Date: Jan. 14, 2021

(65) Prior Publication Data
US 2022/0249678 A1 Aug. 11, 2022

Related U.S. Application Data

(60) Provisional application No. 62/872,336, filed on Jul. 10, 2019.

(51) Int. Cl.
| | |
|---|---|
| *A61K 47/64* | (2017.01) |
| *A61K 9/00* | (2006.01) |
| *A61K 9/14* | (2006.01) |
| *A61K 9/19* | (2006.01) |
| *A61K 47/54* | (2017.01) |
| *A61K 47/60* | (2017.01) |
| *A61K 48/00* | (2006.01) |
| *A61P 11/00* | (2006.01) |
| *C12N 15/113* | (2010.01) |

(52) U.S. Cl.
CPC ........ *A61K 47/6455* (2017.08); *A61K 9/0043* (2013.01); *A61K 9/0075* (2013.01); *A61K 9/145* (2013.01); *A61K 9/19* (2013.01); *A61K 47/549* (2017.08); *A61K 47/60* (2017.08); *A61P 11/00* (2018.01); *C12N 15/113* (2013.01); *A61K 48/00* (2013.01); *C12N 2310/14* (2013.01); *C12N 2310/351* (2013.01); *C12N 2310/3513* (2013.01); *C12N 2320/32* (2013.01)

(58) Field of Classification Search
None
See application file for complete search history.

(56) References Cited

FOREIGN PATENT DOCUMENTS

| | | | | |
|---|---|---|---|---|
| CA | 2682135 | * | 4/2008 | ............... A61K 9/12 |
| WO | 2009027337 | A1 | 3/2009 | |
| WO | 2015061467 | A1 | 4/2015 | |
| WO | 2018156617 | A1 | 8/2018 | |

OTHER PUBLICATIONS

Morys et al., Polymers 2017, 9, 142; doi: 10.3390/polym9040142 (Year: 2017).*

Shokrzadeh et al., Bioorganic & Medicinal Chemistry Letters 24 (2014) 5758-576 (Year: 2014).*

Sahin U, Kariko K, and Tureci O: mRNA-based therapeutics—developing a new class of drugs. Nat Rev Drug Discov 2014; 13(10): pp. 759-780.

Wolff JA, Malone RW, Williams P Chong W, Acsadi G, Jani A, and Felgner PL: Direct gene transfer into mouse muscle in vivo. Science 1990; 247(4949 Pt 1): pp. 1465-1468.

Jirikowski GF, Sanna PP, Maciejewski-Lenoir D, and Bloom FE: Reversal of diabetes insipidus in Brattleboro rats: Intrahypothalamic injection of vasopressin mRNA. Science 1992; 255(5047): pp. 996-998.

Uchida S, Kataoka K, and Itaka K: Screening of mRNA Chemical Modification to Maximize Protein Expression with Reduced Immunogenicity. Pharmaceutics 2015; 7(3): pp. 137-151.

Holtkamp S, Kreiter S, Selmi A, Simon P, Koslowski M, Huber C, Tureci O, and Sahin U: Modification of antigen-encoding RNA increases stability, translational efficacy, and T-cell stimulatory capacity of dendritic cells. Blood 2006; 108(13): pp. 4009-4017.

Sahu I, Haque A, Weidensee B, Weinmann P, and Kormann MSD: Recent Developments in mRNA-Based Protein Supplementation Therapy to Target Lung Diseases. Mol Ther 2019; 27(4): pp. 803-823.

Mays LE, Ammon-Treiber S, Mothes B, Alkhaled M, Rottenberger J, Muller-Hermelink ES, Grimm M, Mezger M, Beer-Hammer S, von Stebut E, Rieber N, Nurnberg B, Schwab M, Handgretinger R, Idzko M, Hartl D, and Kormann MS: Modified Foxp3 mRNA protects against asthma through an IL-10-dependent mechanism. J Clin Invest 2013; 123(3): pp. 1216-1228.

Kormann MS, Hasenpusch G, Aneja MK, Nica G, Flemmer AW, Herber-Jonat S, Huppmann M, Mays LE, Illenyi M, Schams A, Griese M, Bittmann I, Handgretinger R, Hartl D, Rosenecker J, and Rudolph C: Expression of therapeutic proteins after delivery of chemically modified mRNA in mice. Nat Biotechnol 2011; 29(2): pp. 154-157.

Chow MY and Lam JK: Dry Powder Formulation of Plasmid DNA and siRNA for Inhalation. Curr Pharm Des 2015; 21 (27): pp. 3854-3866.

Mitchell J and Nagel M: Particle size analysis of aerosols from medicinal inhalers. KONA Powder and Particle Journal 2004; 22: pp. 32-65.

Malcolmson RJ and Embleton JK: Dry powder formulations for pulmonary delivery. Pharmaceutical science & technology today 1998; 1(9): pp. 394-398.

Chan HK: Dry powder aerosol delivery systems: current and future research directions. J Aerosol Med 2006; 19(1): pp. 21-27.

(Continued)

*Primary Examiner* — Christina M Borgeest
(74) *Attorney, Agent, or Firm* — Leason Ellis LLP

(57) ABSTRACT
Provided are relating to pulmonary delivery of mRNA as inhaled dry powder formulation and compositions comprising the mRNA; also provided are methods of using and making the composition.

20 Claims, 40 Drawing Sheets

Figure 1A:
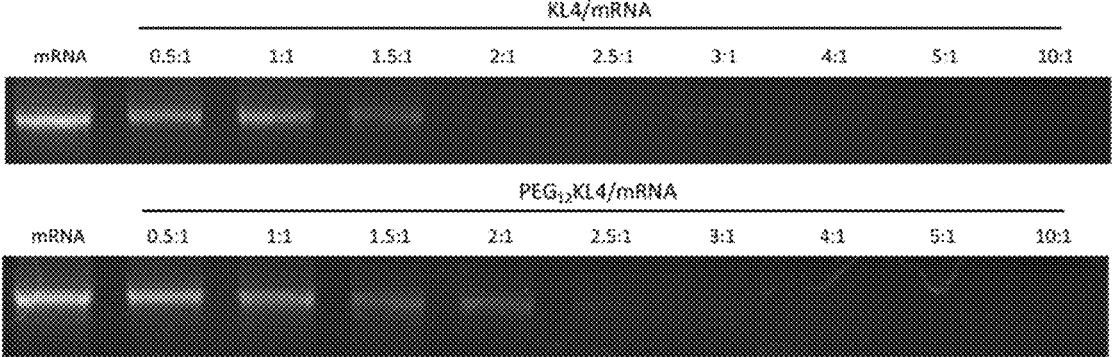

Specification includes a Sequence Listing.

(56)             References Cited

OTHER PUBLICATIONS

Tavernier G, Andries O, Demeester J, Sanders NN, De Smedt SC, and Rejman J: mRNA as gene therapeutic: how to control protein expression. J Control Release 2011; 150(3): pp. 238-247.

Johler SM, Rejman J, Guan S, and Rosenecker J: Nebulisation of IVT mRNA Complexes for Intrapulmonary Administration. PLoS One 2015; 10(9): ppe0137504.

Patel AK, Kaczmarek JC, Bose S, Kauffman KJ, Mir F, Heartlein MW, DeRosa F, Langer R, and Anderson DG: Inhaled Nanoformulated mRNA Polyplexes for Protein Production in Lung Epithelium. Adv Mater 2019; 31(8): ppe1805116.

Robinson E, MacDonald KD, Slaughter K, McKinney M, Patel S, Sun C, and Sahay G: Lipid Nanoparticle-Delivered Chemically Modified mRNA Restores Chloride Secretion in Cystic Fibrosis. Mol Ther 2018; 26(8): pp. 2034-2046.

Qiu Y, Chow MYT, Liang W, Chung WWY, Mak JCW, and Lam JKW: From Pulmonary Surfactant, Synthetic KL4 Peptide as Effective siRNA Delivery Vector for Pulmonary Delivery. Mol Pharm 2017; 14(12): pp. 4606-4617.

Kinbara K: Monodisperse engineered PEGs for bio-related applications. Polymer Journal 2018; 50(8): pp. 689.

Chow MYT, Qiu Y, Lo FFK, Lin HHS, Chan HK, Kwok PCL, and Lam JKW: Inhaled powder formulation of naked siRNA using spray drying technology with I-leucine as dispersion enhancer. Int J Pharm 2017; 530(1-2): pp. 40-52.

Liang W, Chow MYT, Chow SF, Chan HK, Kwok PCL, and Lam JKW: Using two-fluid nozzle for spray freeze drying to produce porous powder formulation of naked siRNA for inhalation. Int J Pharm 2018; 552(1-2): pp. 67-75.

Liao Q, Yip L, Chow MYT, Chow SF, Chan HK, Kwok PCL, and Lam JKW: Porous and highly dispersible voriconazole dry powders produced by spray freeze drying for pulmonary delivery with efficient lung deposition. Int J Pharm 2019; 560: pp. 144-154.

Guan S and Rosenecker J: Nanotechnologies in delivery of mRNA therapeutics using nonviral vector-based delivery systems. Gene therapy 2017; 24(3): pp. 133.

Ito T, Okuda T, Takayama R, and Okamoto H: Establishment of an Evaluation Method for Gene Silencing by Serial Pulmonary Administration of siRNA and pDNA Powders: Naked siRNA Inhalation Powder Suppresses Luciferase Gene Expression in the Lung. J Pharm Sci 2019.

Asai-Tajiri Y, Matsumoto K, Fukuyama S, Kan-o K, Nakano T, Tonai K, Ohno T, Azuma M, Inoue H, and Nakanishi Y: Small interfering RNA against CD86 during allergen challenge blocks experimental allergic asthma. Respiratory research 2014; 15(1): pp. 132.

Goh FY, Cook KL, Upton N, Tao L, Lah LC, Leung BP, and Wong WF: Receptor-interacting protein 2 gene silencing attenuates allergic airway inflammation. The Journal of Immunology 2013; 191(5): pp. 2691-2699.

Miwata K, Okamoto H, Nakashima T, Ihara D, Horimasu Y, Masuda T, Miyamoto S, Iwamoto H, Fujitaka K, and Hamada H: Intratracheal Administration of siRNA Dry Powder Targeting Vascular Endothelial Growth Factor Inhibits Lung Tumor Growth in Mice. Molecular Therapy-Nucleic Acids 2018; 12: pp. 698-706.

Agnoletti M, Bohr A, Thanki K, Wan F, Zeng X, Boetker JP, Yang M, and Foged C: Inhalable siRNA-loaded nano-embedded microparticles engineered using microfluidics and spray drying. European Journal of Pharmaceutics and Biopharmaceutics 2017; 120: pp. 9-21.

Sebastian M, Papachristofilou A, Weiss C, Fruh M, Cathomas R, Hilbe W, Wehler T, Rippin G, Koch SD, Scheel B, Fotin-Mleczek M, Heidenreich R, Kallen KJ, Gnad-Vogt U, and Zippelius A: Phase Ib study evaluating a self- adjuvanted mRNA cancer vaccine (RNActive(R)) combined with local radiation as consolidation and maintenance treatment for patients with stage IV non-small cell lung cancer. BMC Cancer 2014; 14: pp. 748.

Bahl K, Senn JJ, Yuzhakov O, Bulychev A, Brito LA, Hassett KJ, Laska ME, Smith M, Almarsson O, Thompson J, Ribeiro AM, Watson M, Zaks T, and Ciaramella G: Preclinical and Clinical Demonstration of Immunogenicity by mRNA Vaccines against H10N8 and H7N9 Influenza Viruses. Mol Ther 2017; 25(6): pp. 1316-1327.

D'Souza A A and Shegokar R: Polyethylene glycol (PEG): a versatile polymer for pharmaceutical applications. Expert Opin Drug Deliv 2016; 13(9): pp. 1257-1275.

Osman G, Rodriguez J, Chan SY, Chisholm J, Duncan G, Kim N, Tatler AL, Shakesheff KM, Hanes J, Suk JS, and Dixon JE: PEGylated enhanced cell penetrating peptide nanoparticles for lung gene therapy. J Control Release 2018; 285: pp. 35-45.

Huckaby JT and Lai SK: PEGylation for enhancing nanoparticle diffusion in mucus. Adv Drug Deliv Rev 2018; 124: pp. 125-139.

Okuda T, Morishita M, Mizutani K, Shibayama A, Okazaki M, and Okamoto H: Development of spray-freeze-dried SiRNA/PEI powder for inhalation with high aerosol performance and strong pulmonary gene silencing activity. J Control Release 2018; 279: pp. 99-113.

Wu J, Wu L, Wan F, Rantanen J, Cun D, and Yang M: Effect of thermal and shear stresses in the spray drying process on the stability of siRNA dry powders. Int J Pharm 2019; 566: pp. 32-39.

Liu B and Zhou X: Freeze-drying of proteins. Methods Mol Biol 2015; 1257: pp. 459-476.

Maa YF, Nguyen PA, Sweeney T, Shire SJ, and Hsu CC: Protein inhalation powders: spray drying vs spray freeze drying. Pharm Res 1999; 16(2): pp. 249-254.

Farkas DR, Hindle M, and Longest PW: Characterization of a New High-Dose Dry Powder Inhaler (DPI) Based on a Fluidized Bed Design. Ann Biomed Eng 2015; 43(11): pp. 2804-2815.

Sanders N, Rudolph C, Braeckmans K, De Smedt SC, and Demeester J: Extracellular barriers in respiratory gene therapy. Advanced drug delivery reviews 2009; 61(2): pp. 115-127.

Price DN, Kunda NK, and Muttil P: Challenges Associated with the Pulmonary Delivery of Therapeutic Dry Powders for Preclinical Testing. KONA Powder and Particle Journal 2019; 36: pp. 129-144.

Fire, A., et al., Potent and specific genetic interference by double-stranded RNA in Caenorhabditis elegans. Nature, 1998. 391(6669): p. 806-11.

Adams, D., et al., Patisiran, an RNAi Therapeutic, for Hereditary Transthyretin Amyloidosis. N Engl J Med, 2018. 379 (1): p. 11-21.

Ruger, J., et al., Oligonucleotides to the (Gene) Rescue: FDA Approvals 2017-2019. Trends Pharmacol Sci, 2020. 41 (1): p. 27-41.

Scott, L.J., Givosiran: First Approval. Drugs, 2020.

De Paula Brandao, P. R., S.S. Titze-de-Almeida, and R. Titze-de-Almeida, Leading RNA Interference Therapeutics Part 2: Silencing Delta-Aminolevulinic Acid Synthase 1, with a Focus on Givosiran. Mol Diagn Ther, 2020. 24(1): p. 61-68.

Garbuzenko, O.B., et al., Strategy to enhance lung cancer treatment by five essential elements: inhalation delivery, nanotechnology, tumor-receptor targeting, chemo- and gene therapy. Theranostics, 2019. 9(26): p. 8362-8376.

Choi, M., et al., Targeted delivery of Chil3/Chil4 siRNA to alveolar macrophages using ternary complexes composed of HMG and oligoarginine micelles. Nanoscale, 2020. 12(2): p. 933-943.

Park, A.M., et al., Heat Shock Protein 27 Plays a Pivotal Role in Myofibroblast Differentiation and in the Development of Bleomycin-Induced Pulmonary Fibrosis. PLoS One, 2016. 11(2): p. e0148998.

Bohr, A., et al., Anti-Inflammatory Effect of Anti-TNF-alpha SiRNA Cationic Phosphorus Dendrimer Nanocomplexes Administered Intranasally in a Murine Acute Lung Injury Model. Biomacromolecules, 2017. 18(8): p. 2379-2388.

Merckx, P., et al., Surfactant protein B (SP-B) enhances the cellular siRNA delivery of proteolipid coated nanogels for Inhalation therapy. Acta Biomater, 2018. 78: p. 236-246.

Nucci, M.L., R. Shorr, and A. Abuchowski, The therapeutic value of poly (ethylene glycol)-modified proteins. Advanced drug delivery reviews, 1991. 6(2): p. 133-151.

Harris, J.M. and R.B. Chess, Effect of pegylation on pharmaceuticals. Nature reviews Drug discovery, 2003. 2(3): p. 214-221.

Luo, T., et al., PEGylation of paclitaxel largely improves its safety and anti-tumor efficacy following pulmonary delivery in a mouse model of lung carcinoma. J Control Release, 2016. 239: p. 62-71.

(56)           References Cited

OTHER PUBLICATIONS

Aldayel, A.M., et al., Lipid nanoparticles with minimum burst release of TNF-$\alpha$ siRNA show strong activity against rheumatoid arthritis unresponsive to methotrexate. Journal of Controlled Release, 2018. 283: p. 280-289.

Malhotra, M., et al., Development and characterization of chitosan-PEG-TAT nanoparticles for the intracellular delivery of siRNA. International journal of nanomedicine, 2013. 8: p. 2041.

Aldrian, G., et al., PEGylation rate influences peptide-based nanoparticles mediated siRNA delivery in vitro and in vivo. Journal of Controlled Release, 2017. 256: p. 79-91.

Lechanteur, A., et al., PEGylation of lipoplexes: The right balance between cytotoxicity and siRNA effectiveness. European Journal of Pharmaceutical Sciences, 2016. 93: p. 493-503.

Mao, S., et al., Influence of polyethylene glycol chain length on the physicochemical and biological properties of poly (ethylene imine)-graft-poly (ethylene glycol) block copolymer/SiRNA polyplexes. Bioconjugate chemistry, 2006. 17(5): p. 1209-1218.

Santiwarangkool, S., et al., PEGylation of the GALA peptide enhances the lung-targeting activity of nanocarriers that contain encapsulated siRNA. Journal of pharmaceutical sciences, 2017. 106(9): p. 2420-2427.

Kinbara, K., Monodisperse engineered PEGs for bio-related applications. Polymer Journal, 2018. 50(8): p. 689-697.

Gaziova, Z., et al., Chemically defined polyethylene glycol siRNA conjugates with enhanced gene silencing effect. Bioorg Med Chem, 2014. 22(7): p. 2320-6.

Dohmen, C., et al., Defined Folate-PEG-siRNA Conjugates for Receptor-specific Gene Silencing. Mol Ther Nucleic Acids, 2012. 1: p. e7.

Zhang, C.Y., et al., Native chemical ligation for conversion of sequence-defined oligomers into targeted pDNA and siRNA carriers. J Control Release, 2014. 180: p. 42-50.

He, D., et al., Combinatorial Optimization of Sequence-Defined Oligo(ethanamino)amides for Folate Receptor-Targeted pDNA and siRNA Delivery. Bioconjug Chem, 2016. 27(3): p. 647-59.

Liang, W., et al., Inhalable dry powder formulations of siRNA and pH-responsive peptides with antiviral activity against H1N1 influenza virus. Mol Pharm, 2015. 12(3): p. 910-921.

Suk, J.S., et al., PEGylation as a strategy for improving nanoparticle-based drug and gene delivery. Adv Drug Deliv Rev, 2016. 99(Pt A): p. 28-51.

Milla, P., F. Dosio, and L. Cattel, PEGylation of proteins and liposomes: a powerful and flexible strategy to improve the drug delivery. Curr Drug Metab, 2012. 13(1): p. 105-19.

D'Souza A, A. and R. Shegokar, Polyethylene glycol (PEG): a versatile polymer for pharmaceutical applications. Expert Opin Drug Deliv, 2016. 13(9): p. 1257-75.

Bakota, E.L., et al., Self-assembling multidomain peptide fibers with aromatic cores. Biomacromolecules, 2013. 14(5): p. 1370-8.

Wu, Y., et al., A Supramolecular Vaccine Platform Based on alpha-Helical Peptide Nanofibers. ACS Biomater Sci Eng, 2017. 3(12): p. 3128-3132.

Deshpande, M.C., et al., Influence of polymer architecture on the structure of complexes formed by PEG-tertiary amine methacrylate copolymers and phosphorothioate oligonucleotide. J Control Release, 2002. 81(1-2): p. 185-99.

Qiu, Y., et al., Modification of KL4 Peptide Revealed the Importance of Alpha-Helical Structure for Efficient Small Interfering RNA Delivery. Nucleic Acid Ther, 2020.

Rodriguez-Martinez, J.A., et al., Stabilization of alpha-chymotrypsin upon PEGylation correlates with reduced structural dynamics. Biotechnol Bioeng, 2008. 101(6): p. 1142-9.

Lawrence, P. B. and J.L. Price, How PEGylation influences protein conformational stability. Curr Opin Chem Biol, 2016. 34: p. 88-94.

Plesner, B., et al., Effects of PEG size on structure, function and stability of PEGylated BSA. Eur J Pharm Biopharm, 2011. 79(2): p. 399-405.

Merkel, O.M., et al., Nonviral siRNA delivery to the lung: investigation of PEG-PEI polyplexes and their in vivo performance. Mol Pharm, 2009. 6(4): p. 1246-60.

Yan, Y., et al., Aerosol delivery of stabilized polyester-siRNA nanoparticles to silence gene expression in orthotopic lung tumors. Biomaterials, 2017. 118: p. 84-93.

Feldmann, D.P., et al., The impact of microfluidic mixing of triblock micelleplexes on in vitro / in vivo gene silencing and Intracellular trafficking. Nanotechnology, 2017. 28(22): p. 224001.

Kanehira, Y., et al., Intratumoral delivery and therapeutic efficacy of nanoparticle-encapsulated anti-tumor siRNA following intrapulmonary administration for potential treatment of lung cancer. Pharm Dev Technol, 2019. 24(9): p. 1095-1103.

M.G. Ivanov, D.M.I., Chapter 14—Nanodiamond Nanoparticles as Additives to Lubricants, in Ultrananocrystalline Diamond: Synthesis, Properties, and Applications, D.M.G. Olga A. Shenderova, Editor. 2012, William Andrew.

Brown, M.A., A. Goel, and Z. Abbas, Effect of Electrolyte Concentration on the Stern Layer Thickness at a Charged Interface. Angew Chem Int Ed Engl, 2016. 55(11): p. 3790-4.

Mishra, S., P. Webster, and M.E. Davis, PEGylation significantly affects cellular uptake and intracellular trafficking of non-viral gene delivery particles. Eur J Cell Biol, 2004. 83(3): p. 97-111.

Bartlett, D.W. and M.E. Davis, Physicochemical and biological characterization of targeted, nucleic acid-containing nanoparticles. Bioconjug Chem, 2007. 18(2): p. 456-68.

O'Mahony, A.M., et al., Cationic and PEGylated Amphiphilic Cyclodextrins: Co-Formulation Opportunities for Neuronal Sirna Delivery. PLoS One, 2013. 8(6): p. e66413.

Capel, V., et al., Insight into the relationship between the cell culture model, cell trafficking and siRNA silencing efficiency. Biochem Biophys Res Commun, 2016. 477(2): p. 260-5.

Danilkovitch-Miagkova, A., et al., Hyaluronidase 2 negatively regulates RON receptor tyrosine kinase and mediates transformation of epithelial cells by jaagsiekte sheep retrovirus. Proc Natl Acad Sci U S A, 2003. 100(8): p. 4580-5.

Ramachandran, S., et al., Efficient delivery of RNA interference oligonucleotides to polarized airway epithelia in vitro. Am J Physiol Lung Cell Mol Physiol, 2013. 305(1): p. L23-32.

Stewart, C.E., et al., Evaluation of differentiated human bronchial epithelial cell culture systems for asthma research. J Allergy (Cairo), 2012. 2012: p. 943982.

Noah, T.L., et al., Tight junctions and mucin mRNA in BEAS-2B cells. In Vitro Cell Dev Biol Anim, 1995. 31(10): p. 738-40.

Ghio, A.J., et al., Growth of human bronchial epithelial cells at an air-liquid interface alters the response to particle exposure. Part Fibre Toxicol, 2013. 10: p. 25.

Veronese, F.M. and A. Mero, The impact of PEGylation on biological therapies. BioDrugs, 2008. 22(5): p. 315-29.

Zheng, J.C., et al., PEGylation is effective in reducing immunogenicity, immunotoxicity, and hepatotoxicity of alpha-momorcharin in vivo. Immunopharmacol Immunotoxicol, 2012. 34(5): p. 866-73.

Xu, Y., et al., Structure-based antigenic epitope and PEGylation improve the efficacy of staphylokinase. Microb Cell Fact, 2017. 16(1): p. 197.

Qiu, Y.S. et al, "Effective mRNA pulmonary delivery by dry powder formulation of PEGylated synthetic KL4 peptide", Journal of Controlled Release, vol. 314, Oct. 16, 2019 (Oct. 16, 2019), 1-59 pp. 102-115.

Qiu, Y.S. et al, "From pulmonary surfactant—synthetic KL4 peptide as effective siRNA delivery vector for pulmonary delivery", Molecular Pharmaceutics, vol. 14, Nov. 9, 2017 (Nov. 9, 2017), 1-59 abstract, experimental section.

Muralidharan, P. et al, "Inhalable PEGylated Phospholipid Nanocarriers and PEGylated Therapeutics for Respiratory Delivery as Aerosolized Colloidal Dispersions and Dry Powder Inhalers", Pharmaceutics, vol. 6, Jun. 20, 2014 (Jun. 20, 2014), 1-59 abstract; p. 337, paragraph 2—p. 347, table 4.

Gao, H.L.et al, "Applicaiton of Target Peptide in siRNA Delivery for the Research of Lung Cancer Therapy", Chin.J. Lung Cancer, vol. 17, No. 9, Jul. 31, 2015 (Jul. 31, 2015), 1-59 pp. 674-678.

* cited by examiner

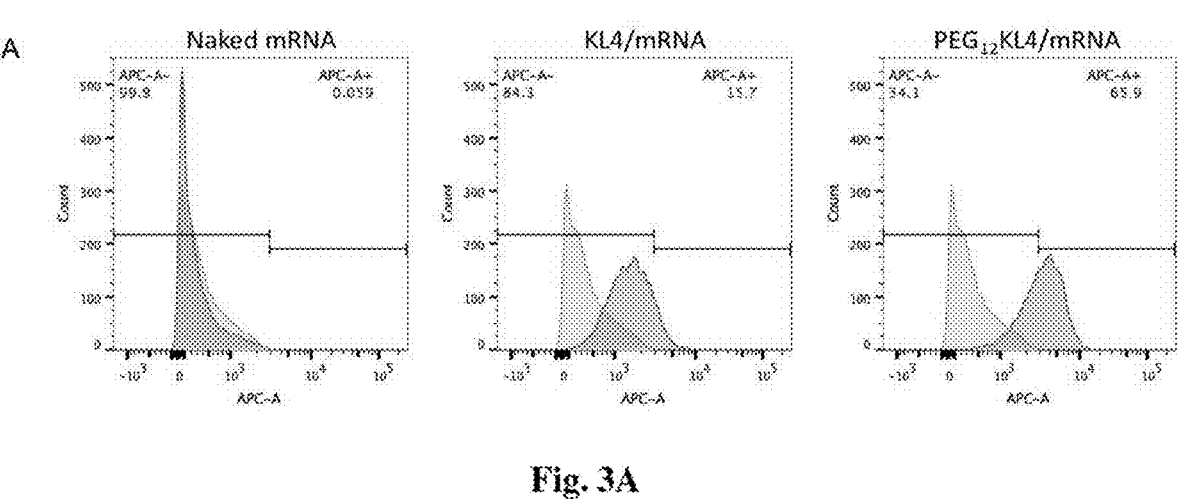
Fig. 3A
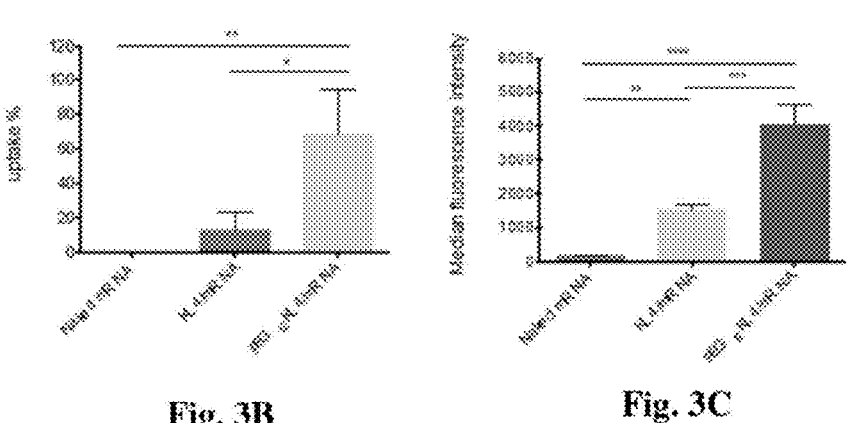
Fig. 3B                    Fig. 3C
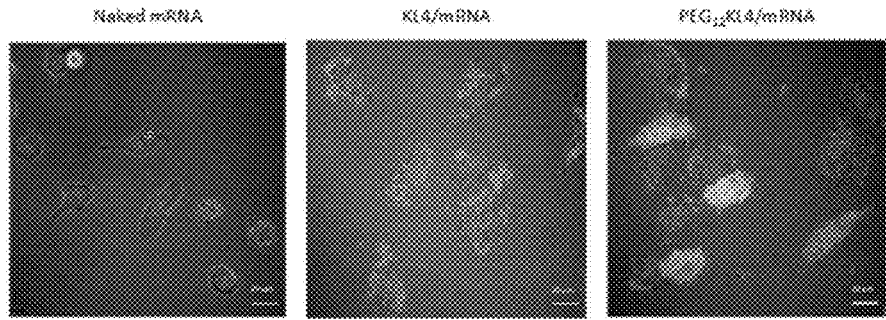
Fig. 3D

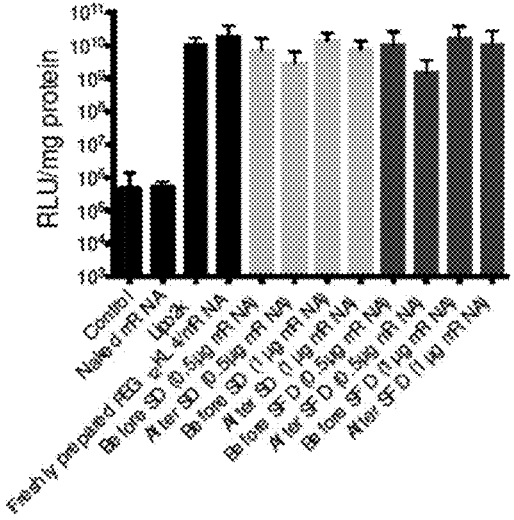
Fig. 7A                                    Fig. 7B

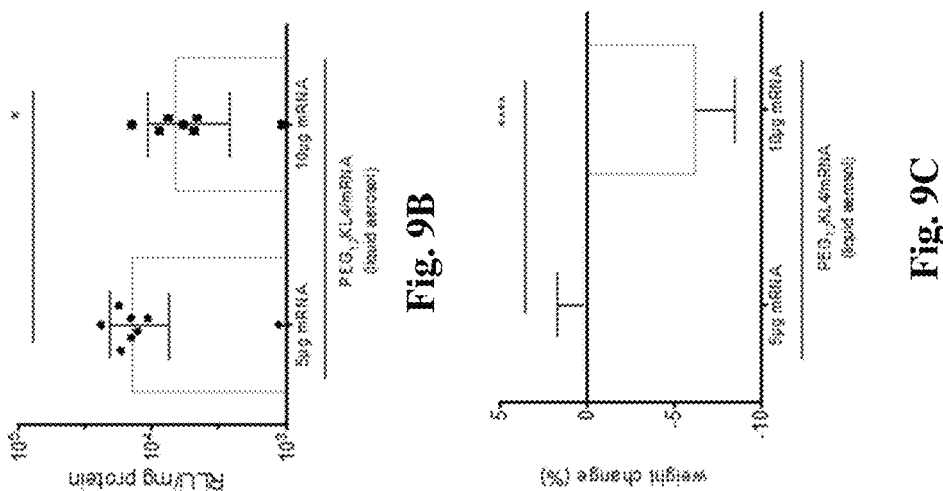
Fig. 9B
Fig. 9C
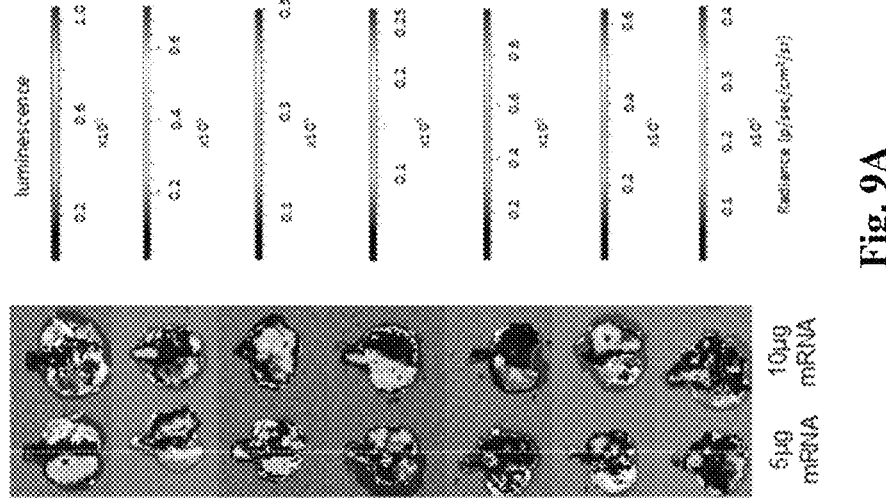
Fig. 9A

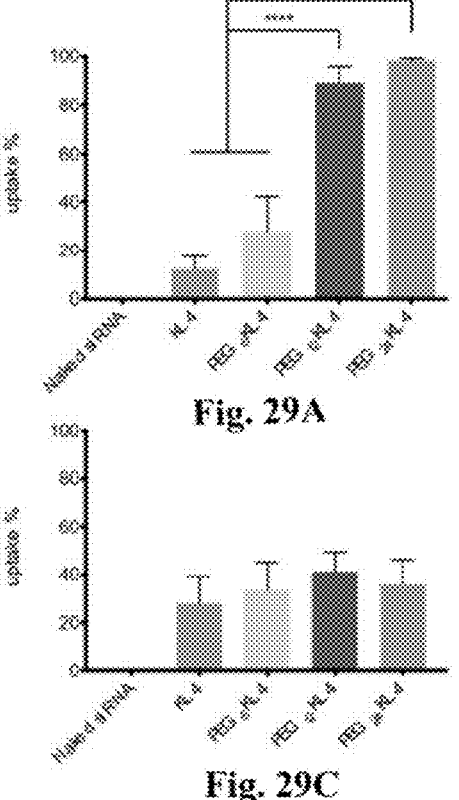
Fig. 29A
Fig. 29C
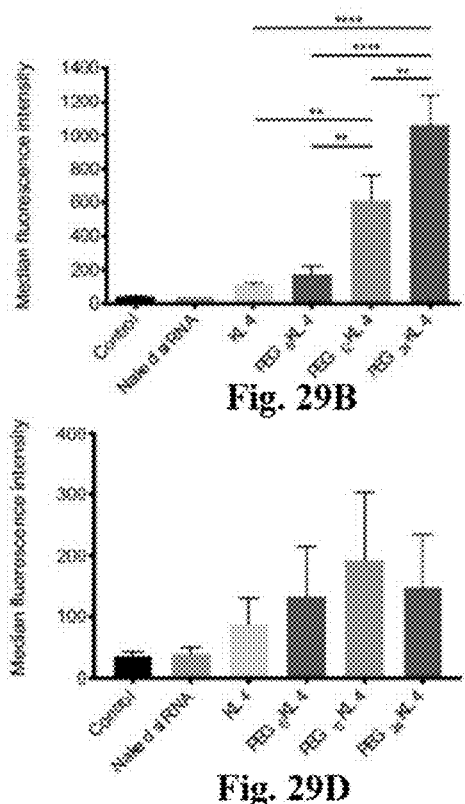
Fig. 29B
Fig. 29D

Comparison within the same peptide prepared at different peptide to siRNA ratios.

| Cell lines | KL4 | PEG$_6$KL4 | PEG$_{12}$KL4 | PEG$_{24}$KL4 |
|---|---|---|---|---|
| A549 | 5:1 vs 10:1 ** <br> 5:1 vs 20:1 ** <br> 5:1 vs 30:1 *** | n.s. | 5:1 vs 10:1 ** <br> 5:1 vs 20:1 * | 5:1 vs 20:1 * |
| JAWSII | 5:1 vs 30:1 ** <br> 10:1 vs 30:1 * | n.s. | 5:1 vs 10:1 * | 5:1 vs 10:1 *** <br> 5:1 vs 20:1 **** <br> 5:1 vs 30:1 **** <br> 10:1 vs 20:1 * |

Comparison between different peptides prepared the same peptide to siRNA ratios.

| Cell lines | 5:1 | 10:1 | 20:1 | 30:1 |
|---|---|---|---|---|
| A549 | KL4 vs PEG$_6$KL4 ** <br> KL4 vs PEG$_{12}$KL4 ** <br> PEG$_6$KL4 vs PEG$_{24}$KL4 ** <br> PEG$_{12}$KL4 vs PEG$_{24}$KL4 ** | KL4 vs PEG$_{12}$KL4 * | KL4 vs PEG$_6$KL4 * <br> KL4 vs PEG$_{12}$KL4 *** <br> KL4 vs PEG$_{24}$KL4 **** <br> PEG$_6$KL4 vs PEG$_{12}$KL4 * <br> PEG$_6$KL4 vs PEG$_{24}$KL4 * | n.s. |
| JAWSII | KL4 vs PEG$_6$KL4 * <br> KL4 vs PEG$_{12}$KL4 **** <br> KL4 vs PEG$_{24}$KL4 ** <br> PEG$_6$KL4 vs PEG$_{12}$KL4 *** <br> PEG$_{12}$KL4 vs PEG$_{24}$KL4 ** | KL4 vs PEG$_6$KL4 * <br> KL4 vs PEG$_{12}$KL4 **** <br> KL4 vs PEG$_{24}$KL4 **** <br> PEG$_6$KL4 vs PEG$_{12}$KL4 **** <br> PEG$_6$KL4 vs PEG$_{24}$KL4 **** <br> PEG$_{12}$KL4 vs PEG$_{24}$KL4 * | KL4 vs PEG$_{12}$KL4 **** <br> KL4 vs PEG$_{24}$KL4 **** <br> PEG$_6$KL4 vs PEG$_{12}$KL4 *** <br> PEG$_6$KL4 vs PEG$_{24}$KL4 **** | KL4 vs PEG$_{12}$KL4 **** <br> KL4 vs PEG$_{24}$KL4 **** <br> PEG$_6$KL4 vs PEG$_{12}$KL4 **** <br> PEG$_6$KL4 vs PEG$_{24}$KL4 **** |

The data were analyzed by one-way ANOVA followed by Tukey's post hoc test. n.s. not significant. *p<0.05, p<0.01, *p<0.001, ****p<0.0001

Fig. 34

| Formulation | SD-0.1% mRNA | SFD-0.1% mRNA | SD-0.5% mRNA | SFD-0.5% mRNA |
|---|---|---|---|---|
| Date of preparation | 19/11/18 | 13/01/19 | 23/01/19 | 23/01/19 |
| Duration of storage | 19 months | 17 months | 17 months | 17 months |

Fig. 39

PEGYLATED SYNTHETIC KL4 PEPTIDE, COMPOSITIONS AND METHODS THEREOF

CROSS-REFERENCE TO RELATED PATENT APPLICATIONS

This application is a U.S. National Stage Application under 35 U.S.C. § 371 of International Patent Application No. PCT/CN2020/101299 filed Jul. 10, 2020, which claims the benefit of priority of U.S. Patent Application No. 62/872,336 filed Jul. 10, 2019, both of which are incorporated by reference in their entireties. The International Application was published on Jan. 14, 2021, as International Publication No. WO/2021/004524 A1.

SEQUENCE LISTING

The instant application contains a Sequence Listing which has been submitted electronically in ASCII format and is hereby incorporated by reference in its entirety. Said ASCII copy, created on Sep. 26, 2025, is named 10030_007947-US1_SL.txt and is 1,865 bytes in size.

1. FIELD

The present disclosure relates to pulmonary delivery of mRNA as inhaled dry powder formulation and composition comprising the mRNA. Also provided are methods of using and making the composition.

2. BACKGROUND

The use of nucleic acids to manipulate gene expression is a powerful therapeutic strategy for the treatment of many diseases. One example is to exploit messenger RNA (mRNA) to generate therapeutic proteins in vivo [1]. The successful uses of in vitro transcribed mRNA techniques for the production of proteins in animals were first reported in the 1990s [2, 3], but these early promising results did not immediately translate into clinic benefits due to the concerns of mRNA instability, risk of innate immunogenicity and inefficient in vivo delivery. Thanks to the advancement of biotechnological innovation in the last decade, chemically modified mRNA can now be produced with enhanced stability and reduced immunogenicity, as well as increased protein expression compared to the unmodified mRNA [4, 5]. However, safe and efficient in vivo delivery remains a major obstacle in mRNA therapeutics development.

Local administration of mRNA by inhalation for the treatment of lung diseases is desirable due to its non-invasive nature, increased local drug concentration and reduced systemic side effects, hence improve treatment efficacy. In particular, dry powder formulation is highly desirable for pulmonary delivery. While liquid aerosol can be delivered to the lungs of patients through nebulization, dry powder formulation of nucleic acids offers several additional advantages such as superior stability, better sterility and longer shelf-life [9]. However, formulation of dry powder aerosol of mRNA is highly challenging. The powder must be highly dispersible and exhibits good aerodynamic properties for effective lung deposition. The integrity and biological activity of the mRNA must be preserved during the drying process, considering that the long single-stranded mRNA molecule is fragile and easily degraded by thermal and shear stresses [13, 14]. Although there are few papers reported the liquid aerosol formulation of mRNA [8, 15, 16], inhaled dry powder formulations of mRNA to generate therapeutic proteins for pulmonary delivery have not been reported so far. The clinical application of KL4 peptide as delivery vector is hindered by its poor solubility due to the presence of hydrophobic leucine residue in the sequence. There is a need to provide a stable and effective mRNA delivery vehicle.

3. SUMMARY

Pulmonary delivery of messenger RNA (mRNA) to generate therapeutic proteins has considerable potential as therapy or vaccine for a range of lung diseases. Inhaled dry powder formulation of mRNA is particularly attractive as it has superior stability and dry powder inhaler is easy to use. Both a safe and effective mRNA delivery vector and a suitable particle engineering method are required to produce a formulation that is respirable and mediates robust transfection in the lung.

Provided herein is a novel RNA delivery vector. In one embodiment, the RNA delivery vector is $PEG_{12}KL4$. In one embodiment, the synthetic cationic KL4 peptide is attached to a monodisperse linear polyethylene glycol (PEG) of 12-mers. In certain embodiments, the $PEG_{12}KL4$ formed nano-sized complexes with mRNA at 10:1 ratio (w/w) and mediated effective transfection on human lung epithelial cells. In certain embodiments, provided herein are $PEG_{12}KL4$/mRNA complexes that are formulated into dry powder by spray drying (SD) and spray freeze drying (SFD) techniques. In certain embodiments, both SD and SFD powder exhibited satisfactory aerosol properties for inhalation, with mass median aerodynamic diameter (MMAD) of 4.5 μm and 1.5 μm, respectively. In certain embodiments, the biological activity of the $PEG_{12}KL4$/mRNA complexes are preserved after drying. In one embodiment, using luciferase mRNA, the intratracheal administration of the liquid or powder aerosol of $PEG_{12}KL4$/mRNA complexes at a dose of 5 μg mRNA resulted in luciferase expression in the deep lung region of mice at 24 h post-transfection. The transfection efficiency was superior to naked mRNA or lipoplexes (Lipofectamine 2000), in which luciferase expression was weaker and restricted to the tracheal region only. There was no sign of immunogenicity or toxicity of the $PEG_{12}KL4$/mRNA complexes after single intratracheal administration.

Provided herein is a mRNA transfection agent for pulmonary delivery. Also provided herein is the preparation of dry powder mRNA formulations that are inhalable with good in vivo transfection efficiency.

Provided herein is the KL4 peptide system for mRNA delivery. In one embodiment, hydrophilic polyethylene glycol (PEG) is covalently attached to the KL4 peptide.

Furthermore, provided herein are two particle engineering techniques, namely spray drying (SD) and spray freeze drying (SFD), to produce inhaled powder formulation of mRNA. The physicochemical properties, aerosol performance, transfection efficiency and the safety profile of the formulations were thoroughly evaluated. The overall goal is to develop a safe, stable and reliable delivery platform for robust mRNA transfection in the airways that could be applied for the treatment of a range of respiratory diseases or mRNA vaccines.

Provided herein is a pegylated peptide comprising a cationic KL4 peptide and a monodisperse linear PEG comprising 6-24 units. In one embodiment, the peptide comprises 12 PEG units which peptide is $PEG_{12}KL4$. In one embodiment, the $PEG_{12}KL4$/mRNA complex comprises a $PEG_{12}KL4$ peptide and a mRNA. In one embodiment, the ratio of $PEG_{12}KL4$ to mRNA is 10:1.

Provided herein is a composition comprising the peptide, mRNA and a bulking agent. In one embodiment, the bulking agent is mannitol. In one embodiment, the composition is in a dry powder formulation. In one embodiment, the dry powder formulation has a powder size of below 5 μm. In one embodiment, the powder has a dispersion property of a fine particle fraction that is >40% in cascade impactor study.

Provided herein is a method of delivering a mRNA to a subject comprising the steps of administering a $PEG_{12}KL4/$ mRNA complex to the subject via inhalation or nasal administration. In one embodiment, the mRNA is delivered to lung epithelial cells of the subject.

Provided herein is a method of treating a lung disease or providing vaccination, said method comprising the step of administering the $PEG_{12}KL4/$mRNA complex via inhalation or nasal administration. In one embodiment, the lung disease is cystic fibrosis or lung inflammatory diseases. In one embodiment, the vaccination is against influenza.

Provided herein is a method of producing a dry powder formulation comprising the steps of:
    (i) providing a solution comprising a $PEG_{12}KL4$, mRNA and a bulking agent; and
    (ii) spray drying or spray freeze drying the solution in step (i).

In one embodiment, the mass median aerodynamic diameter is about 4.5 μm using spray drying method. In one embodiment, the mass median aerodynamic diameter is about 1.5 μm using spray freeze drying method.

Provided herein is a $PEG_{6-24}KL4/DNA$ complex comprising a $PEG_{6-24}KL4$ peptide and a DNA. In one embodiment, the $PEG_{6-24}KL4/DNA$ complex is a $PEG_{12}KL4/DNA$ complex. In one embodiment, the ratio of $PEG_{12}KL4$ to DNA is 10:1, 15:1, or 20:1.

Provided herein is a composition comprising the peptide, DNA and a bulking agent. In one embodiment, the bulking agent is mannitol. In one embodiment, the composition is in a dry powder formulation. In one embodiment, the dry powder formulation has a powder size of about 5 μm. In one embodiment, the powder has a dispersion property of a fine particle fraction that is >40% in cascade impactor study.

Provided herein is a method of delivering a DNA to a subject comprising the steps of administering a $PEG_{6-24}$ KL4/DNA complex to the subject via inhalation or nasal administration. In one embodiment, the $PEG_{6-24}KL4/DNA$ complex is a $PEG_{12}KL4/DNA$ complex. In one embodiment, the DNA is delivered to lung epithelial cells of the subject.

Provided herein is a method of treating a lung disease or providing vaccination, said method comprising the step of administering the $PEG_{6-24}KL4/DNA$ complex via inhalation or nasal administration. In one embodiment, the $PEG_{6-24}$ KL4/DNA complex is a $PEG_{12}KL4/DNA$ complex. In one embodiment, the lung disease is cystic fibrosis or lung inflammatory diseases. In one embodiment, the vaccination is against influenza.

Provided herein is a method of producing a dry powder formulation comprising the steps of:
    (i) providing a solution comprising a $PEG_{6-24}KL4$, DNA and a bulking agent; and
    (ii) spray drying or spray freeze drying the solution in step (i).

In one embodiment, the $PEG_{6-24}KL4$ is a $PEG_{12}KL4$. In one embodiment, the mass median aerodynamic diameter is about 4.5 μm using spray drying method.

In one embodiment, the mass median aerodynamic diameter is about 1.5 μm using spray freeze drying method.

4. DESCRIPTION OF THE FIGURES

Figure 1B:
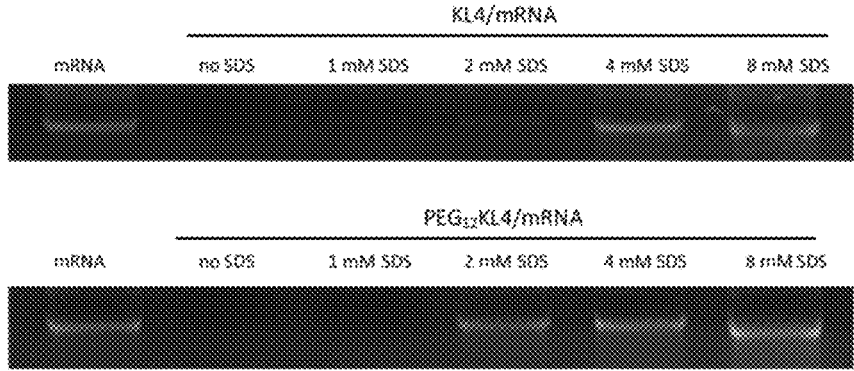

FIGS. 1A-1B. Gel retardation assay of (1A) mRNA binding and (1B) mRNA release. For mRNA binding, KL4/mRNA and $PEG_{12}KL4/$mRNA complexes were prepared at 0.5:1 to 10:1 ratio (w/w). For mRNA release, the complexes were prepared at 10:1 ratio (w/w) and sodium dodecyl sulphate (SDS) solutions at 1 to 8 mM were added to dissociate the complexes. Unbound mRNA was included as control.

Figure 2A:
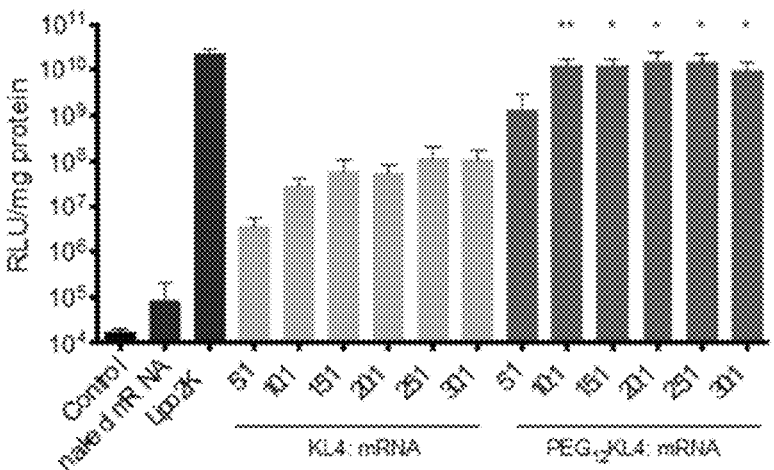
Figure 2B:
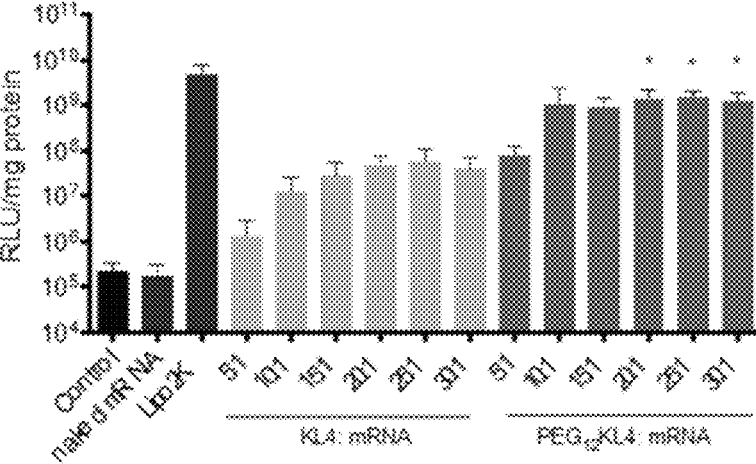

FIGS. 2A-2B. Luciferase mRNA transfection on (2A) A549 cells and (2B) BEAS-2B cells. KL4/mRNA or $PEG_{12}KL4/$mRNA complexes were prepared at 5:1 to 30:1 ratio (w/w) with 1 μg of mRNA in a 24-well plate. Untreated cells, naked mRNA and Lipofectamine 2000 (Lipo2K)/mRNA complexes (2:1 v/w) were included as controls. Luciferase expression was measured at 24 h post-transfection. The data was expressed as the mean value of relative light unit (RLU) per mg of protein±standard deviation (n=3). The data were analyzed by unpaired two-tailed Student's t-test. $*p<0.05$, $**p<0.01$ between KL4/mRNA and $PEG_{12}KL4/$mRNA complexes prepared at the same ratio.

FIGS. 3A-3D. Cellular uptake study using flow cytometry and confocal microscopy. A549 cells were treated with naked mRNA, KL4/mRNA and $PEG_{12}KL4/$mRNA prepared at 10:1 ratio (w/w) with cyanine-5 labeled mRNA. Cells were examined at 4 h post-transfection using flow cytometry—(3A) representative histograms showing the population of cyanine-5 positive cells (red) compared to the untreated control (blue); (3B) percentage of cells with mRNA uptake; and (3C) median fluorescence intensity of the cells. Values are the mean±standard deviation. The data was analyzed by one-way ANOVA followed by Tukey's post-hoc test. $*p<0.05$, $p<0.01$, $*p<0.001$, $****p<0.0001$ (n=3). (3D) Confocal images of cells transfected with cyanine-5 (red) labelled mRNA and EGFP (green) expression; the nuclei (blue) were stained with Hoechst. Scale bar=20 μm.

Figures 4A, 4B:
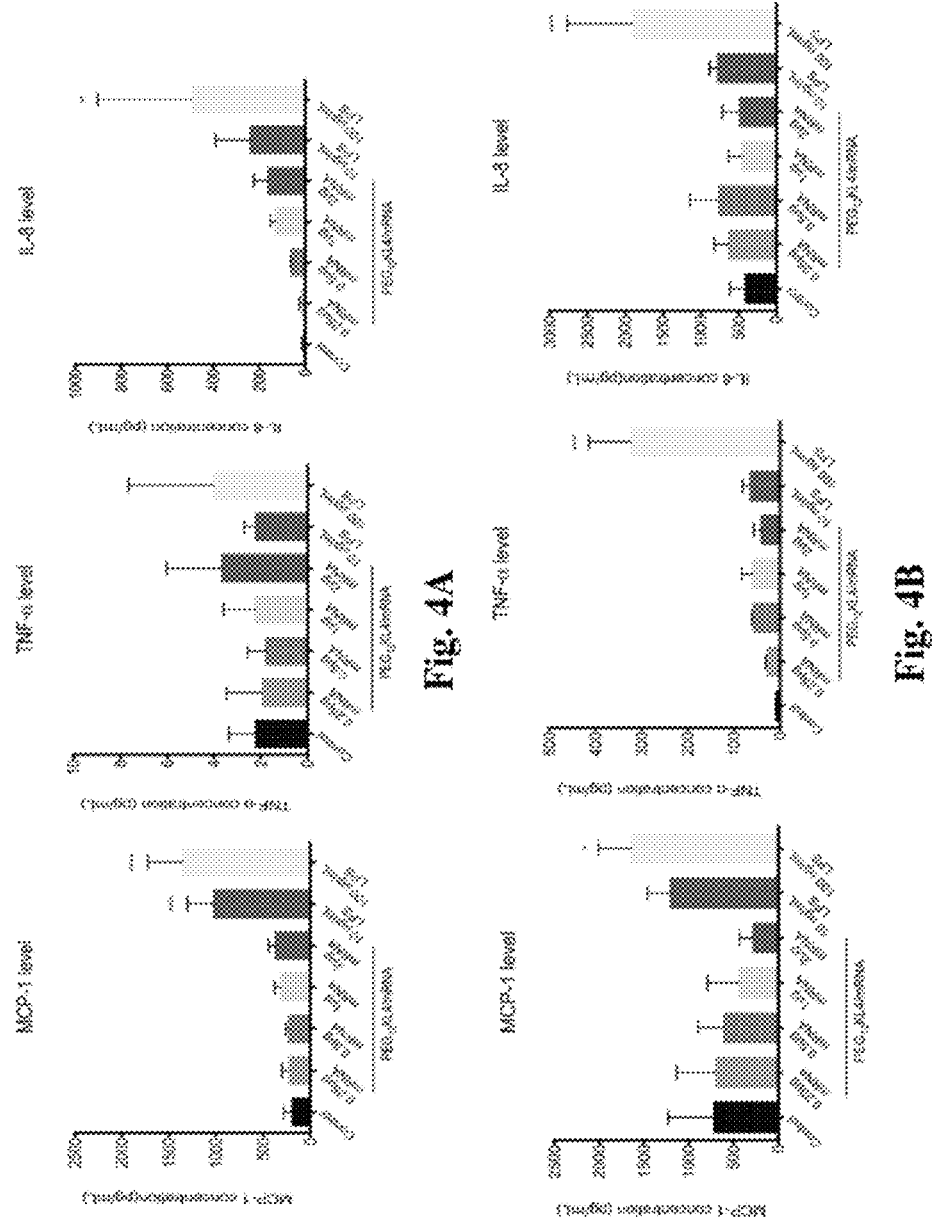

FIGS. 4A-4B. Release of pro-inflammatory cytokines in (4A) A549 cells and (4B) THP-1 cells after mRNA transfection. The cells were transfected with $PEG_{12}KL4/$mRNA complexes prepared at 10:1 ratio (w/w) in 0.25 to 2 μg mRNA per well in 24-well plate. Untreated cells and cells treated with LPS were used as negative and positive control, respectively. The level of MCP-1, TNF-α and IL-8 released from the cells were measured at 24 h post-transfection. The data was analysed by one-way ANOVA followed by Dunnett's post-hoc test as compared with the negative control. $*p<0.05$, $p<0.01$, $**p<0.0001$. Data were presented as mean±standard deviation (n=3).

Figure 5:
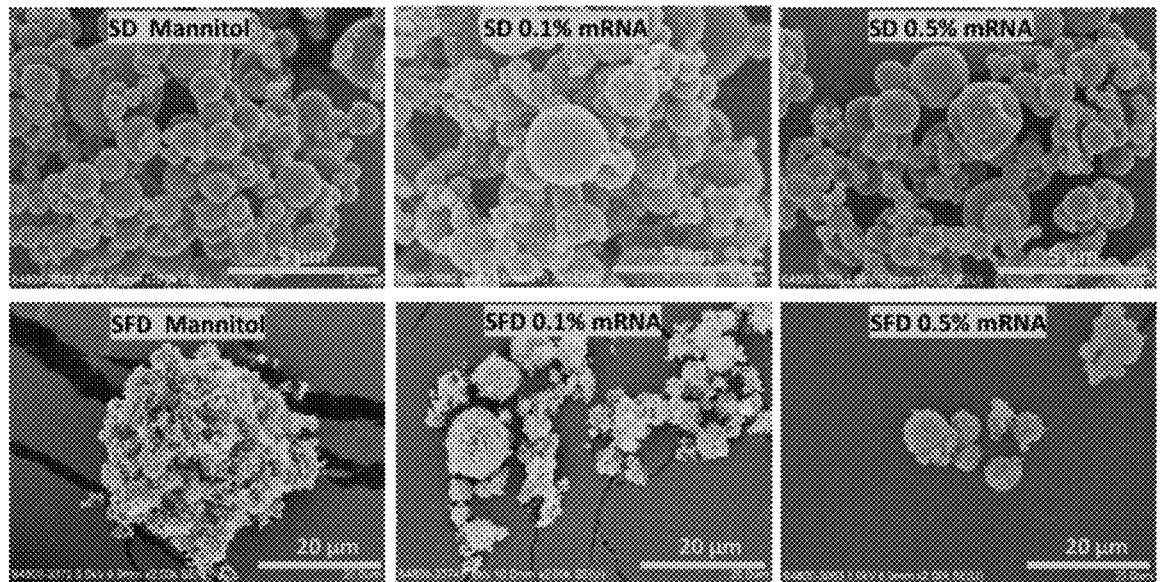

FIG. 5. The scanning electron microscopy (SEM) images of different spray dried (SD) and spray freeze dried (SFD) formulations of $PEG_{12}KL4/$mRNA complexes. Formulations containing mannitol only were included for comparison. The images of SD formulations were taken at ×10,000 magnification (scale bar=5 μm) and the images of SFD formulations were taken at ×2,000 magnification (scale bar=20 μm).

Figure 6A:
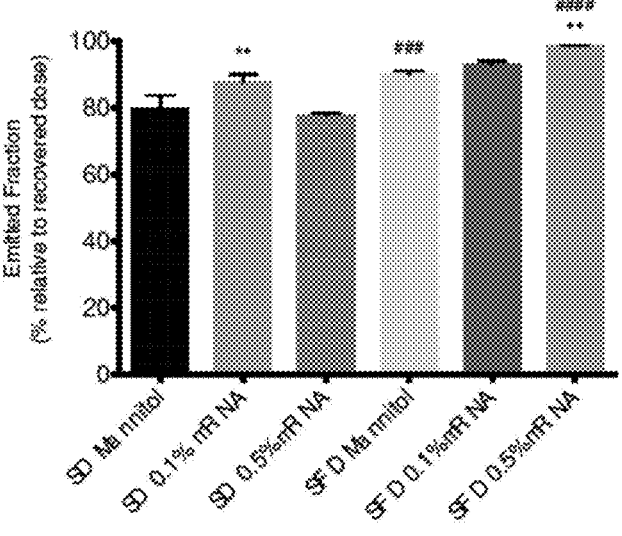
Figure 6B:
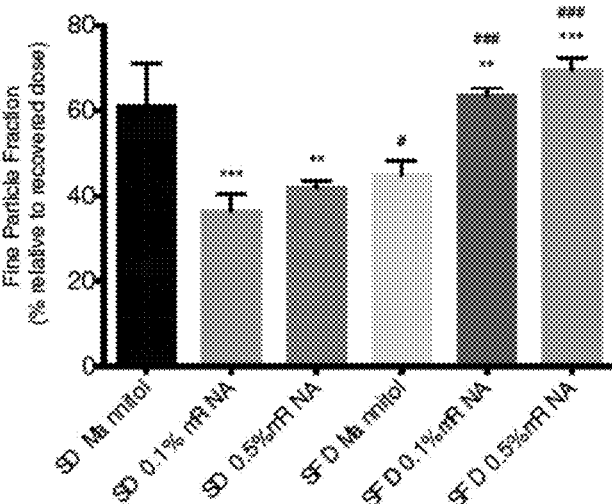

FIGS. 6A-6B. Aerosolization performance of spray dried (SD) and spray freeze dried (SFD) powder evaluated by the Next Generation Impactor (NGI). (6A) The emitted fraction (EF) and (6B) fine particle fraction (FPF) were expressed as the percentage by mass of mannitol relative to the recovered mass. The data were analysed by one-way ANOVA followed by Tukey's post-hoc test. p<0.01, *p<0.001 compared to the mannitol only formulation prepared by the same drying method. ##p<0.01, ###p<0.001, ####p<0.0001 compared between the SD and SFD formulations of the same mRNA concentration. Data were presented as mean±standard deviation (n=3).

FIGS. 7A-7B. Luciferase mRNA transfection on A549 cells with dry powder formulations with (A) 0.1% mRNA formulations and (B) 0.5% mRNA formulations. Dry powders were reconstituted and added to the cells at 0.5 or 1 μg mRNA per well in a 24-well plate. Naked mRNA, Lipofectamine 2000 (Lipo2k)/mRNA complexes (2:1 v/w ratio) and freshly prepared PEG$_{12}$KL4/mRNA complexes (10:1 w/w ratio) containing 1 μg mRNA were used as controls. Luciferase expression was measured at 24 h post-transfection. The data were analyzed by unpaired two-tailed Student's t-test. *p<0.05 compared samples before and after drying. Relative light unit (RLU)/mg protein were shown as mean±standard deviation (n=3).

Figures 8A, 8B:
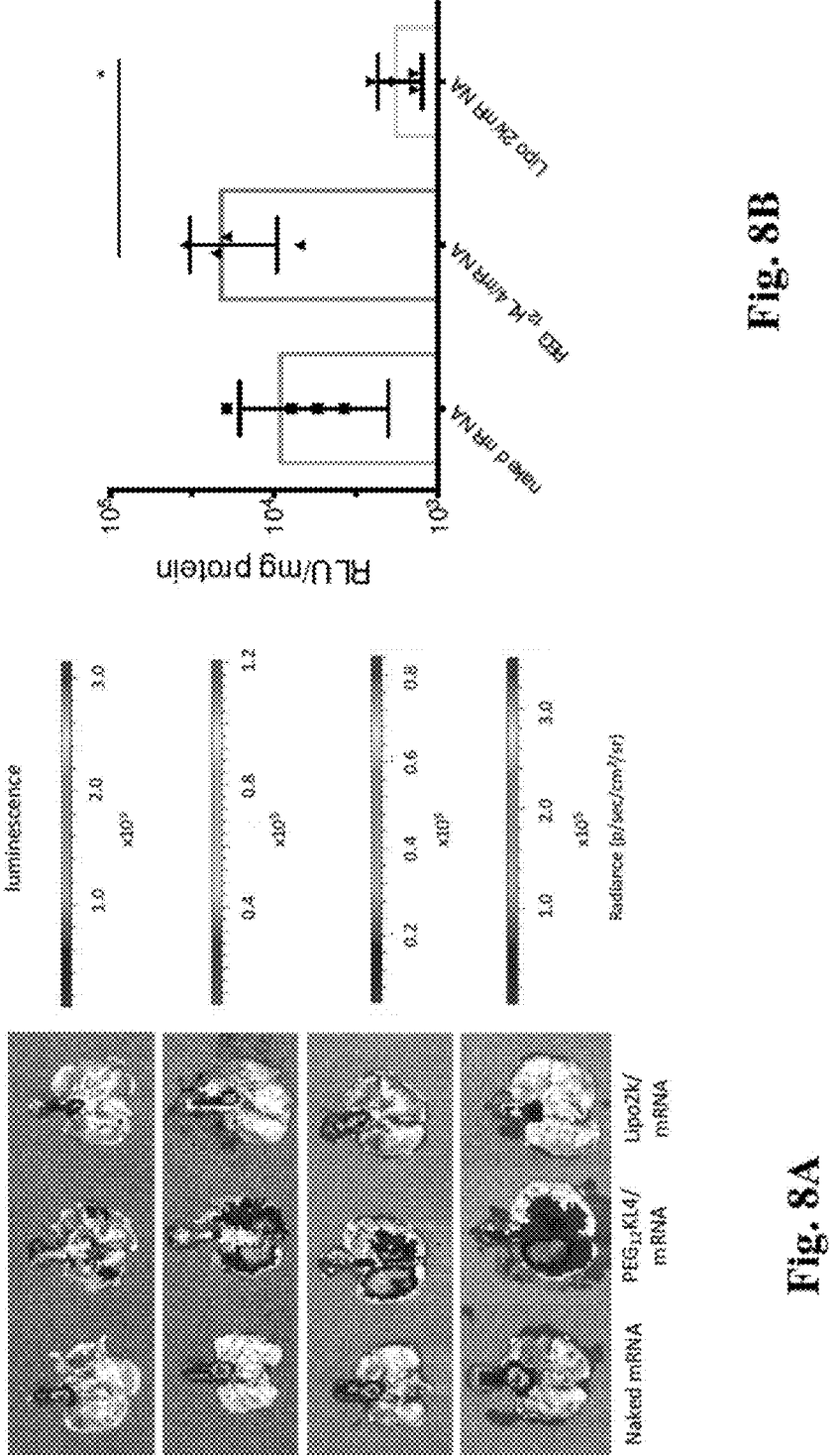

FIGS. 8A-8B. Pulmonary delivery of mRNA formulations with different transfection agents. BALB/c mice (~20 g) were administered intratracheally with (i) naked mRNA; (ii) PEG$_{12}$KL4/mRNA complexes at 10:1 ratio (w/w); and (iii) Lipofectamine 2000 (Lipo2k)/mRNA complexes at 2:1 ratio (v/w). Each mouse received 10 μg of mRNA in a final volume of 75 μL PBS. At 24 h post-administration, (8A) the lungs were isolated for bioluminescence imaging; (8B) luciferase protein expression of lung tissues were measured, and the data was expressed at the mean value of relative light unit (RLU) per mg of protein±standard deviation (n=4). The data were analysed by one-way ANOVA followed by Tukey's post-hoc test, *p<0.05.

FIGS. 9A-9C. Pulmonary delivery of mRNA formulations with different mRNA dose. BALB/c mice (~20 g) were administered intratracheally with PEG$_{12}$-KL4/mRNA complexes at 10:1 ratio (w/w), containing either (i) 5 μg or (ii) 10 μg of mRNA in a final volume of 75 μL PBS. At 24 h post-administration, (9A) the lungs were isolated for bioluminescence imaging; (9B) luciferase protein expression of lung tissues were measured, and the data was expressed at the mean value of relative light unit (RLU) per mg of protein±standard deviation. (9C) Body weight of the mice was monitored before and at 24 h after administration, and the data was presented as mean value of percentage of weight change±standard deviation (n=7-8). The data were analyzed by unpaired two-tailed Student's t-test, *p<0.05, ****p<0.0001.

Figure 10A:
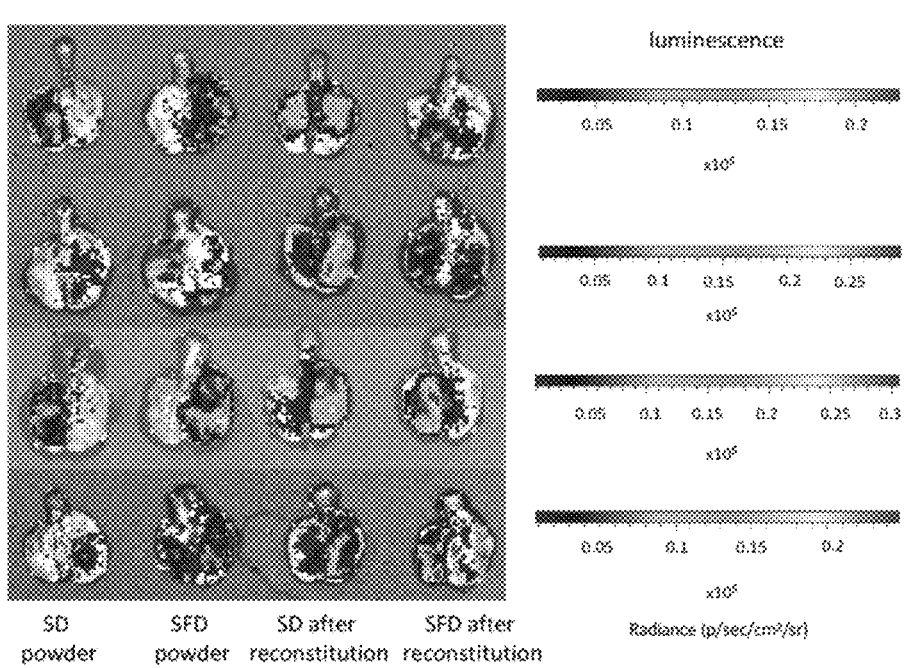
Figure 10B:
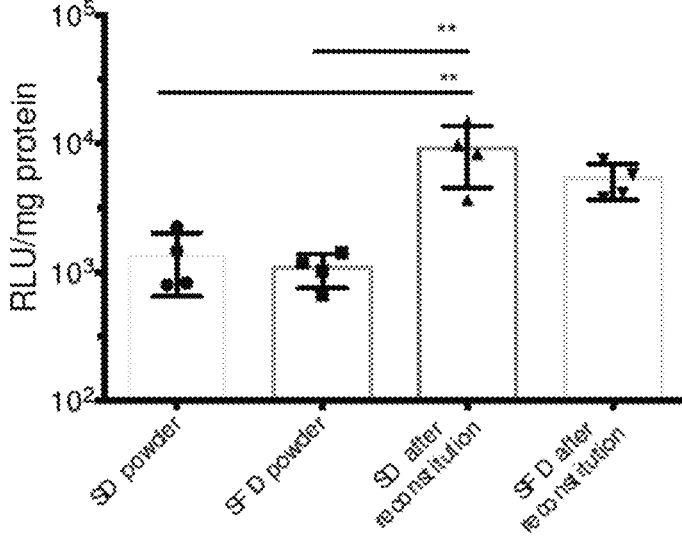

FIGS. 10A-10B. Pulmonary delivery of mRNA formulations as powder aerosol or reconstituted liquid aerosol. BALB/c mice (~20 g) were administered intratracheally with (i) SD-0.5% mRNA formulation as powder aerosol (1 mg); (ii) SFD-0.5% mRNA formulation as powder aerosol (1 mg); (iii) SD-0.5% mRNA formulation reconstituted as liquid aerosol (1 mg in 75 μL PBS); (iv) SFD-0.5% mRNA formulation reconstituted as liquid aerosol (1 mg in 75 μL PBS). Each mouse received a dose of 5 μg mRNA. At 24 h post-administration, (10A) the lungs were isolated for bioluminescence imaging; (10B) luciferase protein expression of lung tissues were measured, and the data was expressed at the mean value of relative light unit (RLU) per mg of protein±standard deviation (n=4). The data were analysed by one-way ANOVA followed by Tukey's post-hoc test, **p<0.01.

Figures 11A, 11B:
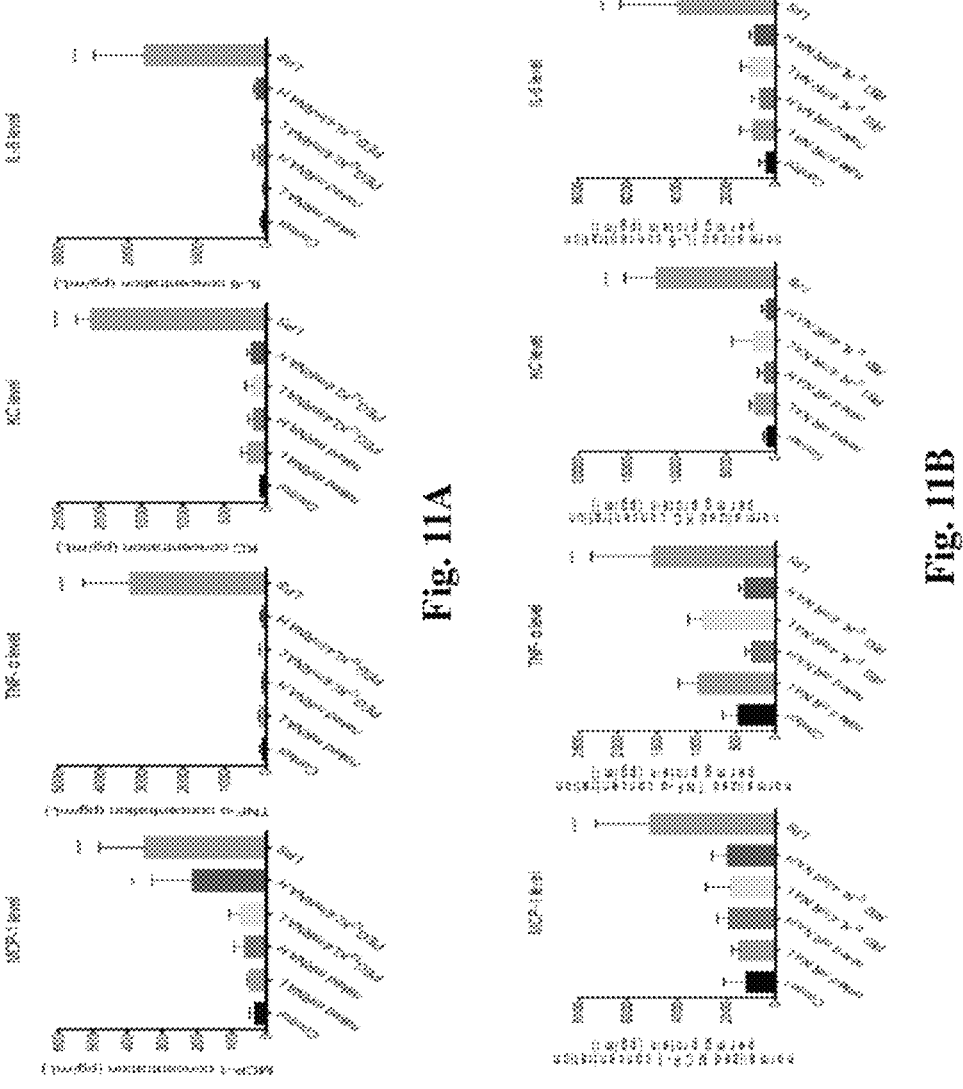
Figures 12A, 12B, 12C, 12D, 12E, 12F, 12G:
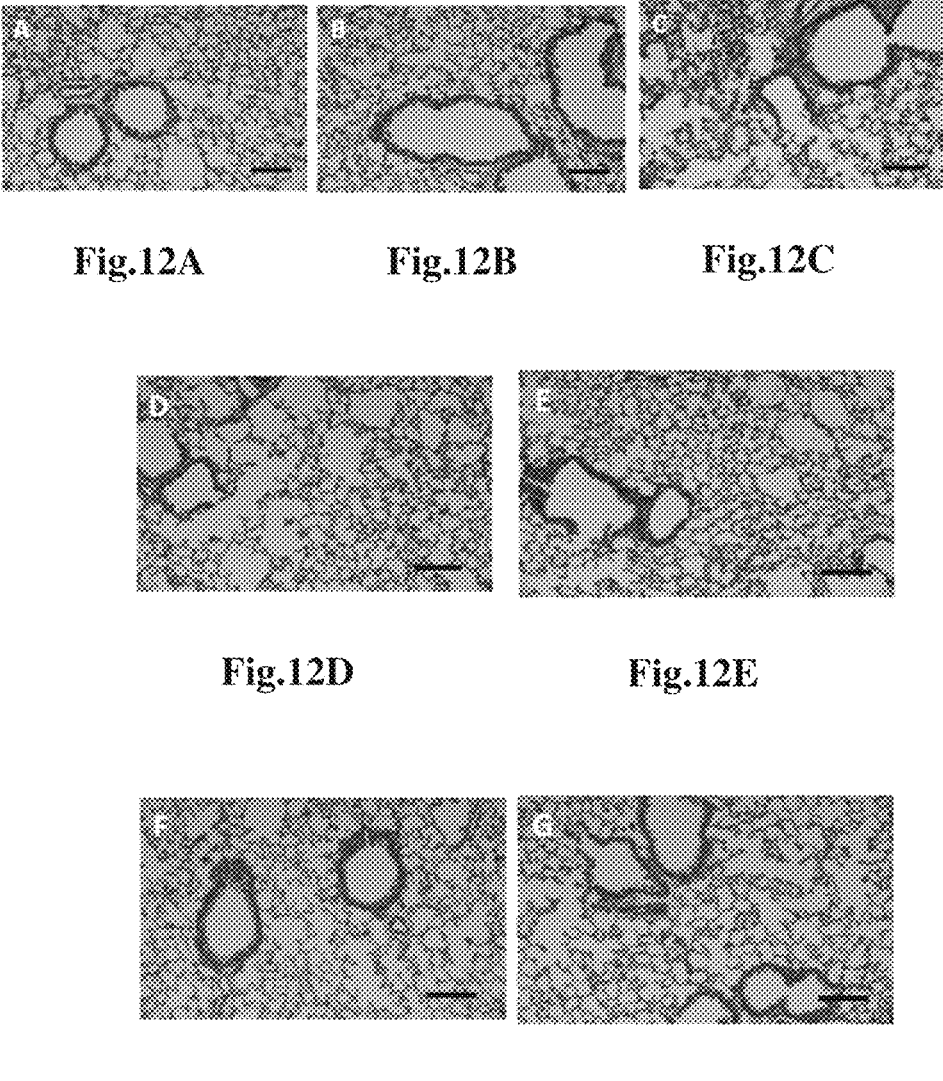

FIGS. 11A-11B. Level of pro-inflammatory cytokines following pulmonary delivery of mRNA formulations. BALB/c mice were administered intratracheally with (i) PBS as control; (ii) naked mRNA L (low dose of 5 μg); (iii)

naked mRNA H (high dose of 10 μg); (iv) PEG$_{12}$KL4/mRNA L (low dose of 5 μg); (v) PEG$_{12}$KL4/mRNA H (high dose of 10 μg); and (vi) LPS (10 μg), all in a final volume of 75 μL PBS. At 24 h post-administration, cytokines levels in (11A) bronchoalveolar lavage fluid (BALF) and (11B) lung homogenates were detected by ELISA. Data are expressed as mean±standard deviation (n=4-6). Statistical analysis was conducted by one-way ANOVA followed by Dunnett's post-hoc test as compared with control. p<0.01, *p<0.001, ****p<0.0001.

FIGS. 12A-12G. Histology of the lungs of BALB/c mice following pulmonary delivery of mRNA formulation—(12A) untreated control; mice were intratracheally administered with (12B) PBS (75 μL); (12C) LPS (10 μg in 25 μL PBS); (12D) mRNA (5 μg in 75 μL PBS); (12E) freshly prepared PEG$_{12}$KL4/mNRA complexes (5 μg mRNA in 75 μL PBS); (12F) SFD-0.5% mRNA powder (1 mg); and (12G) SD-0.5% mRNA powder (1 mg). Slides were viewed using an upright microscope at 20× magnification (scale bar=100 μm).

Figure 13A:
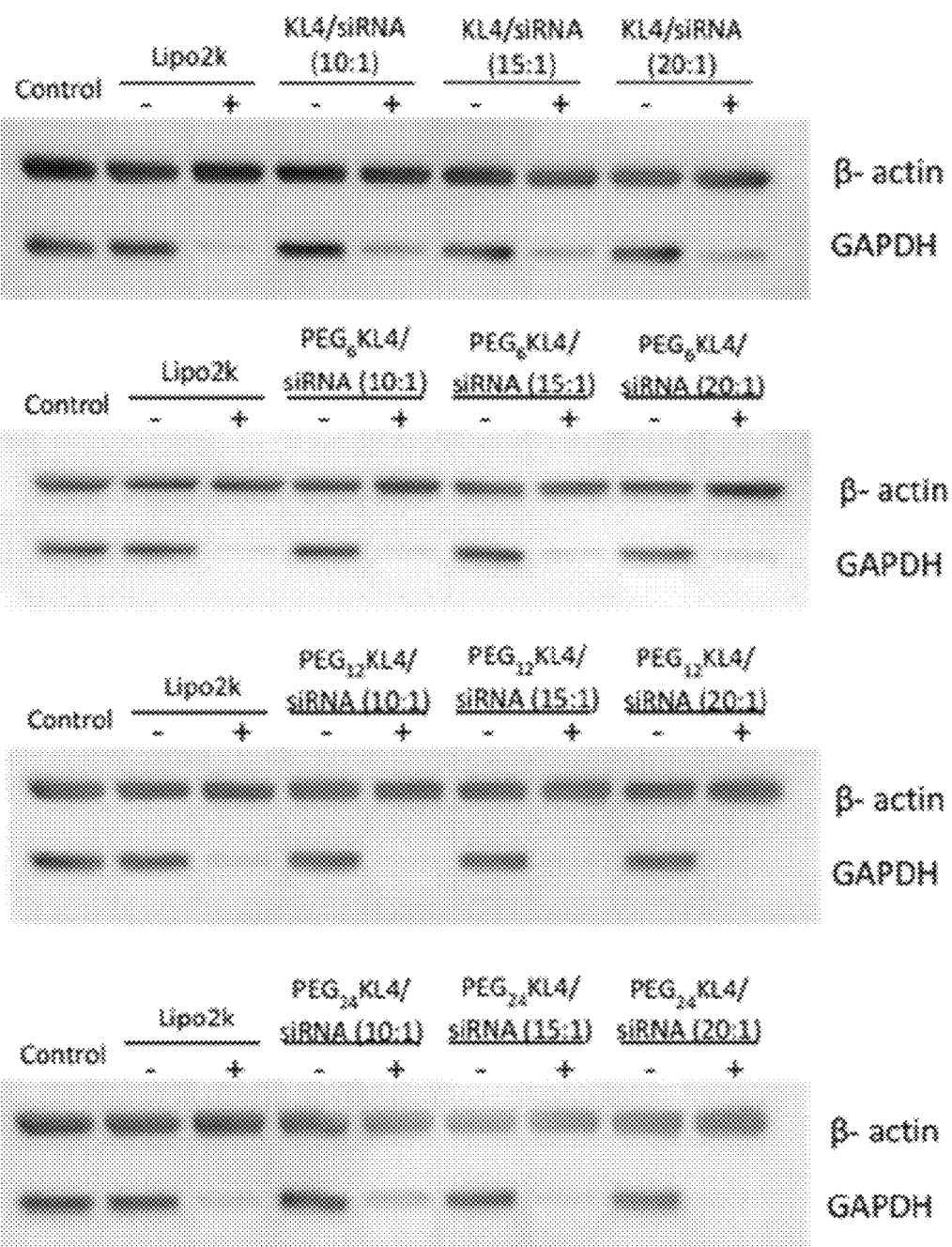
Figure 13B:
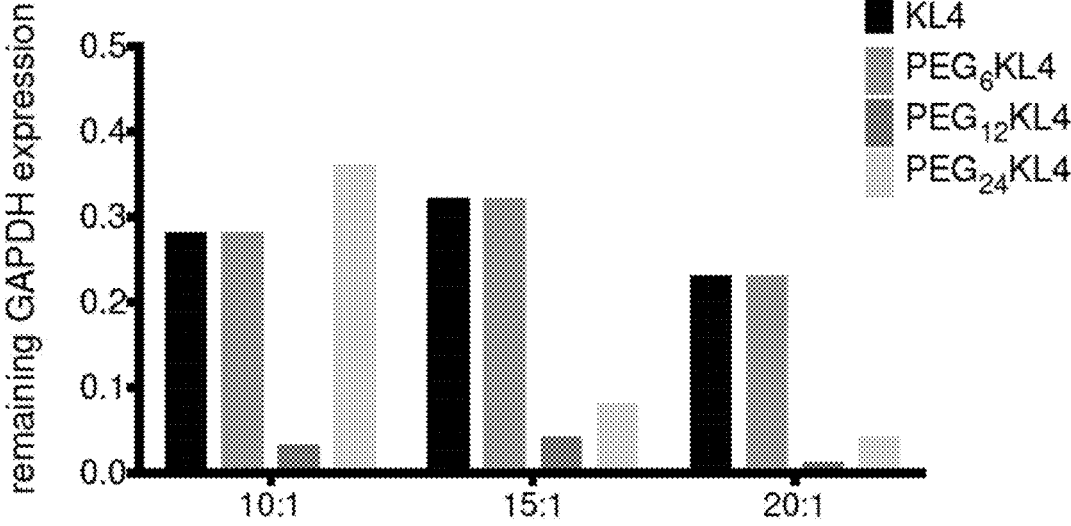

FIGS. 13A-13B siRNA transfection on A549 cells. KL4, PEG$_6$KL4, PEG$_{12}$KL4 and PEG$_{24}$KL4 were used to form complexes with siRNA at 10:1, 15:1 and 20:1 ratios (w/w). The complexes containing 50 pmol of GAPDH siRNA (+) or negative control scramble siRNA (−) were added to the cells in a six-well plate. Untreated cells and Lipofectamine 2000 (Lipo2k)/siRNA at 2:1 (v/w) ratio were included for comparison. Western blot analysis (left) of GAPDH was performed at 72 h post-transfection with β-actin used as internal control. Densitometry results (right) were shown as remaining GAPDH expression compared to the negative siRNA control (n=1). PEG$_{12}$KL4 was superior to KL4 in mediating siRNA transfection at all tested ratios.

Figure 14:
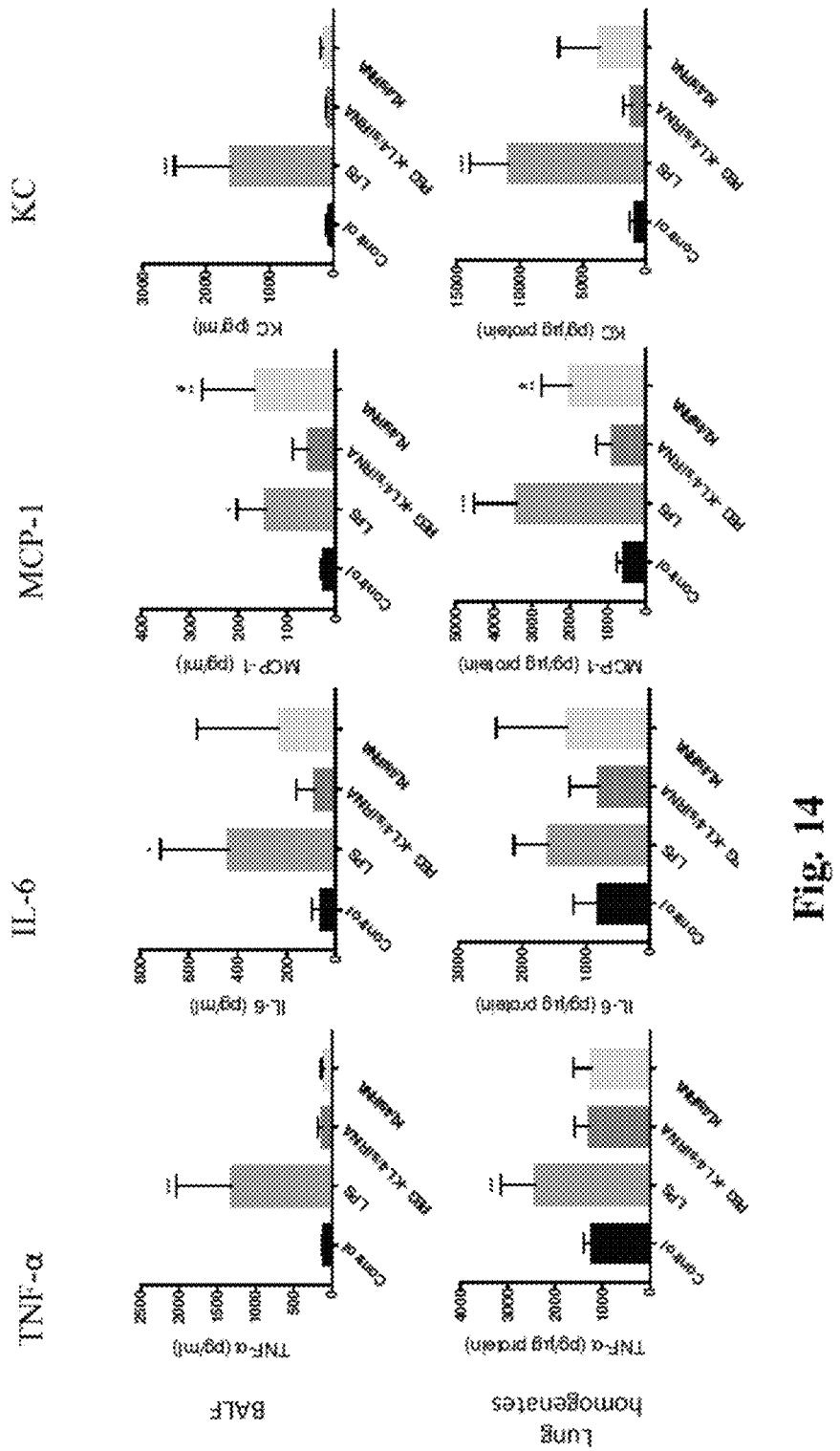

FIG. 14. In vivo immunogenicity study. BALB/c mice (~20 g) and scramble siRNA were used. LPS (10 μg), PEG12-KL4/siRNA (100 μg/10 μg) or KL4/siRNA (100 μg/10 μg) in 75 μl PBS were administered to the mice through intratracheal route using MicroSprayer (Penn Century). At 24 h post-administration, cytokines and chemokines levels in BALF and lung homogenates were detected by ELISA. Data are expressed as mean±SD of 6-7 mice per group. Statistical analysis was conducted by one-way ANOVA (Tukey post-hoc test). *p<0.05, p<0.01, *p<0.001, ****p<0.0001 vs control group treated with PBS; #p<0.05 vs PEG12-KL4/siRNA group. There was no significant difference between the control and PEG12KL4/siRNA group.

Figure 15:
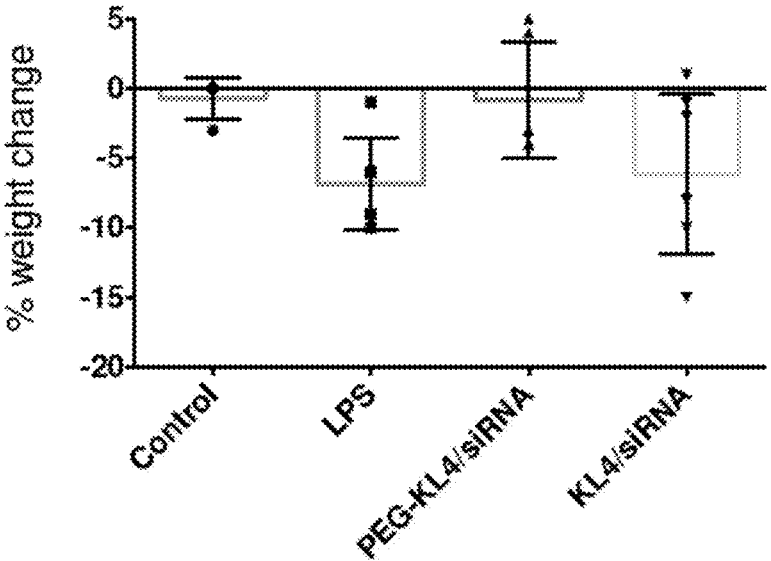

FIG. 15. Change of body weight. BALB/c mice (~20 g) and scramble siRNA were used. LPS (10 μg), PEG$_{12}$-KL4/siRNA (100 μg/10 μg) or KL4/siRNA (100 μg/10 μg) in 75 μl PBS were administered to the mice through intratracheal route using MicroSprayer Aerosolizer (PennCentury). The body weight of the mice were measured before and 24 h post-administration. The percentage of body weight was calculated. Data are expressed as mean±SD of 4-7 mice per group. There was no significant body weight loss in mice treated with PEGylated KL4 peptide/siRNA complexes.

Figure 16B:
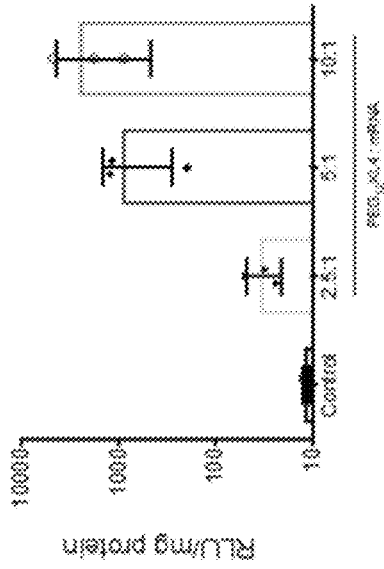
Figure 16A:
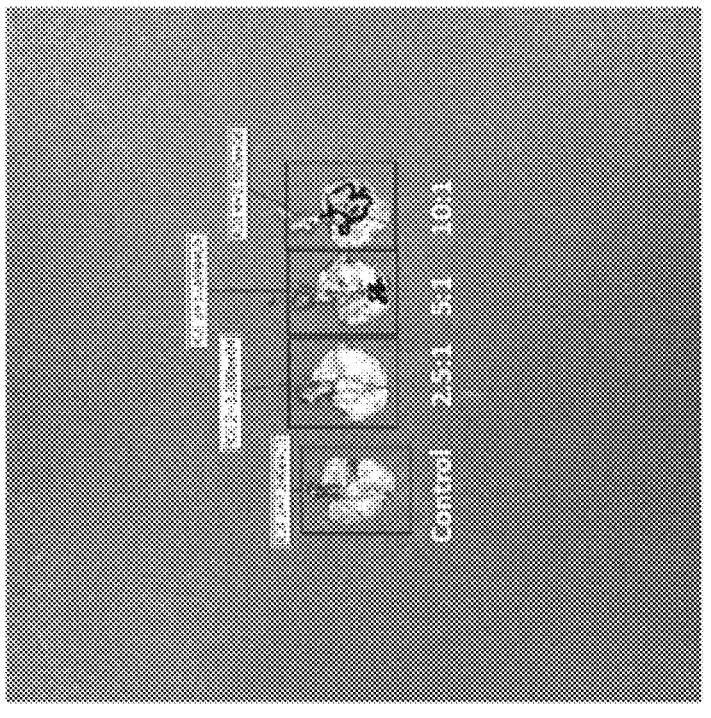

FIGS. 16A-16B. Pulmonary delivery of PEG$_{12}$KL4/mRNA complexes prepared at different ratios. BALB/c mice (~20 g) were administered intratracheally with PEG$_{12}$KL4/mRNA complexes prepared at 2.5:1; 5:1 and 10:1 ratios w/w, with 10 μg mRNA at a final volume of 75 μL in PBS. Mice treated with PBS were included as control. At 24 h post-administration, (16A) the lungs were isolated for bioluminescence imaging; (16B) luciferase protein expression of lung tissues was measured and the data was expressed at the mean value of relative light unit (RLU) per mg of protein±standard deviation (n=3).

Figures 17A, 17B:
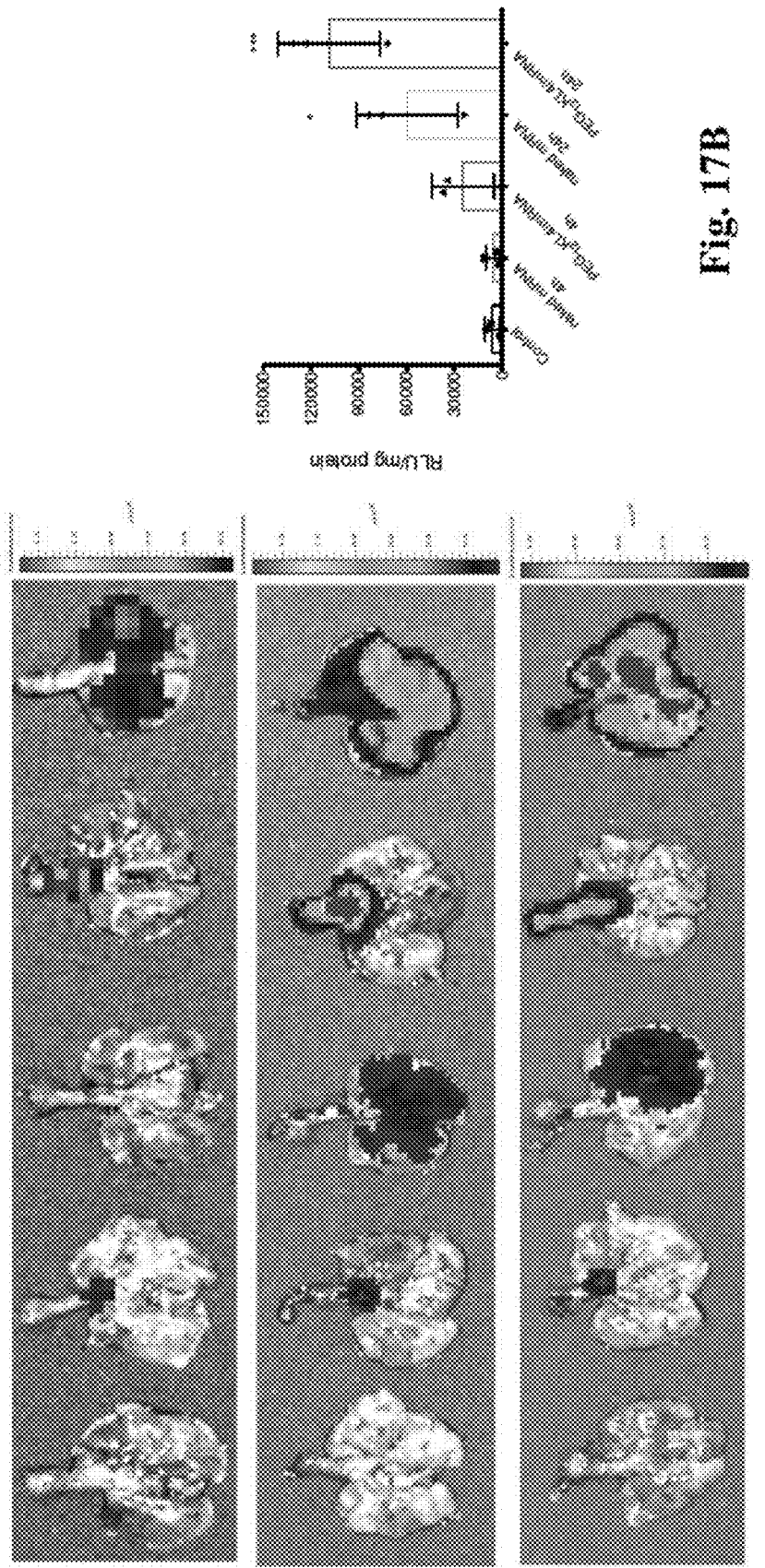

FIGS. 17A-17B. Pulmonary delivery of mRNA formulations at different time points. BALB/c mice (~20 g) were administered intratracheally with (i) PBS as control; (ii) naked mRNA (10 µg mRNA); (iii) PEG12-KL4/mRNA complexes at 10:1 ratio (10 µg mRNA), all in a final volume of 75 µL in PBS. At 4 h and 24 h post-administration, (17A) the lungs were isolated for bioluminescence imaging; (17B) luciferase protein expression of lung tissues was measured and the data was expressed at the mean value of relative light unit (RLU) per mg of protein±standard deviation (n=3). Statistical analysis was conducted by one-way ANOVA followed by Dunnett's post-hoc test as compared with control. *p<0.05, ***p<0.001.

Figure 18:
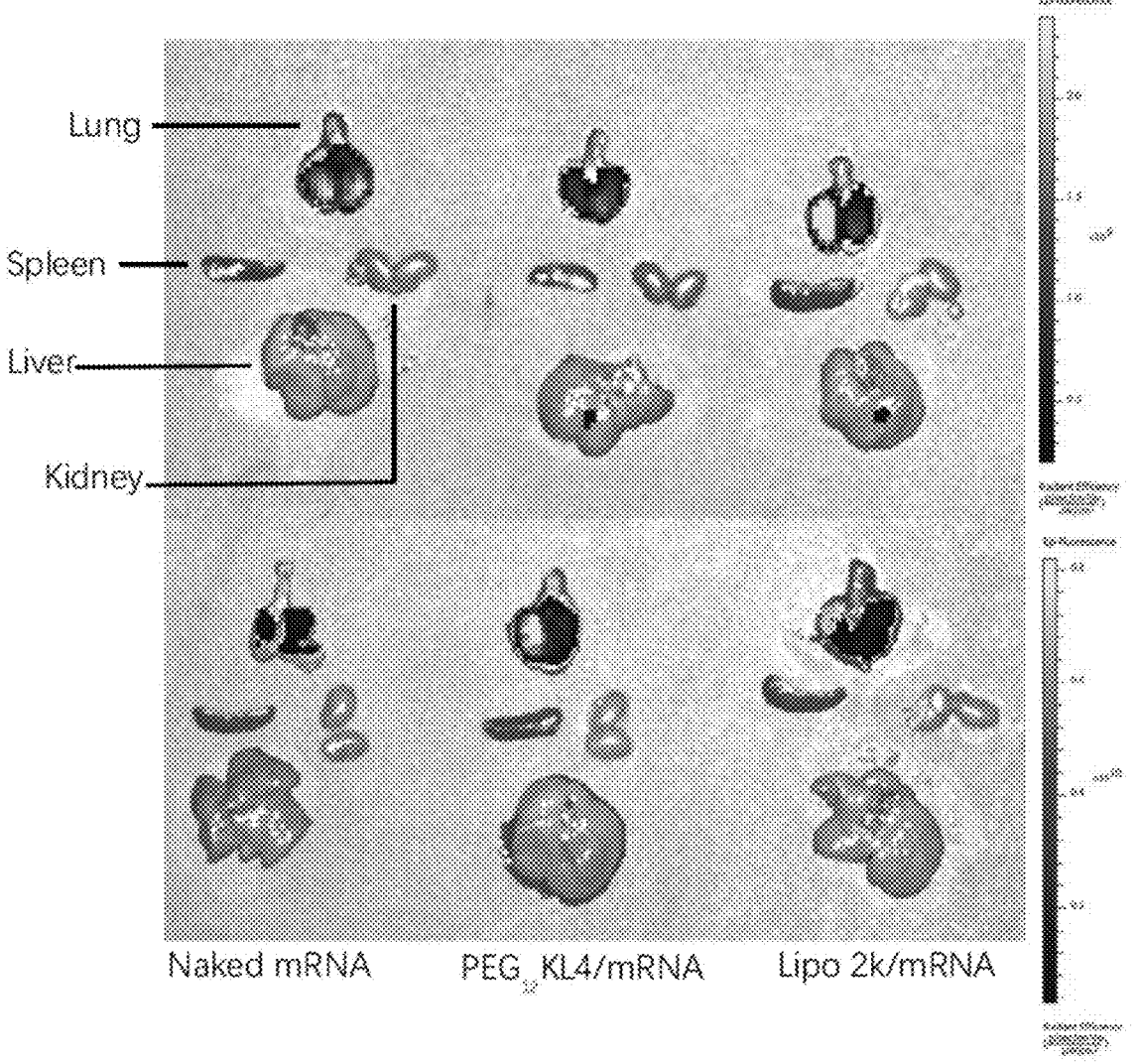

FIG. 18. Biodistribution of cyanine-5 labeled mRNA formulations. BALB/c mice (~20 g) were administered intratracheally with (i) naked mRNA; (ii) $PEG_{12}$-KL4/mRNA complexes at 10:1 ratio (w/w); and (iii) Lipofectamine 2000/mRNA at 2:1 ratio (w/w), all contained 10 µg mRNA in 75 µL PBS. At 4 h post-administration, the lung, liver, kidney and spleen tissues were isolated and the cyanine 5 fluorescent signal of the tissues was measured (n=2).

Figure 19:
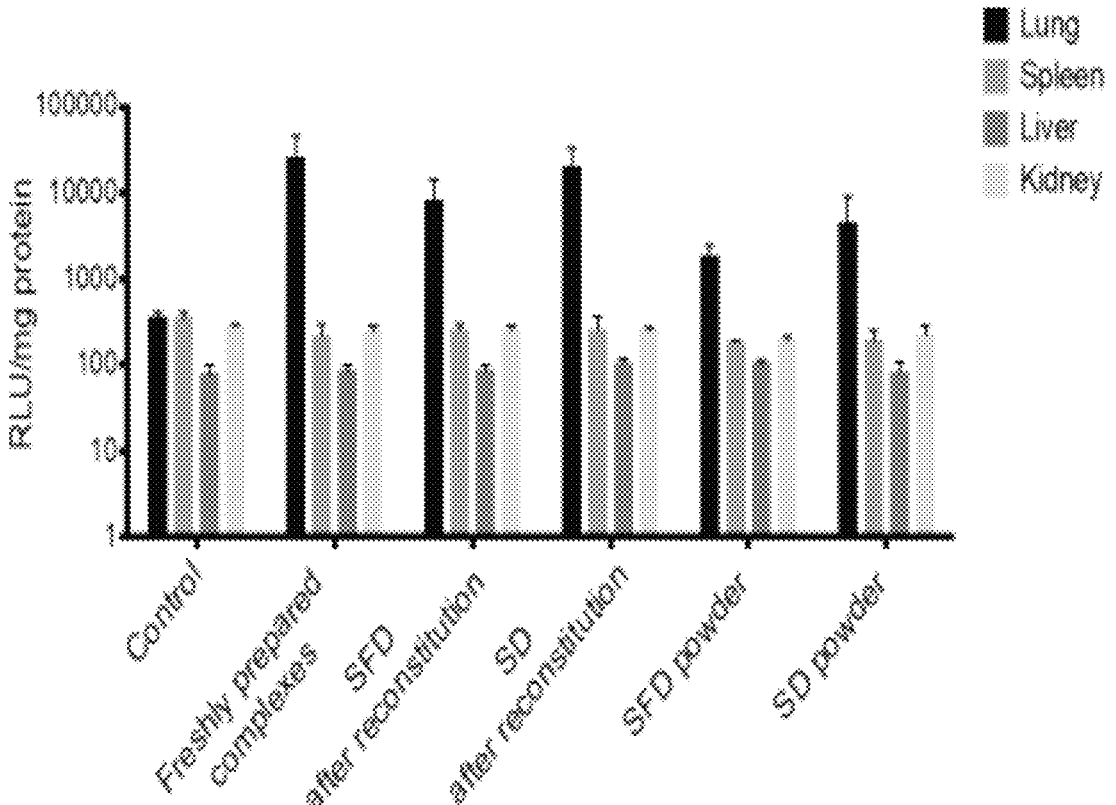

FIG. 19. Biodistribution of PEG12-KL4/mRNA complexes with luciferase mRNA formulations. BALB/c mice (~20 g) were administered intratracheally with (i) PBS as control; (ii) PEG12-KL4/mRNA complexes prepared 10:1 ratio (w/w) as liquid aerosol; (iii) SFD-0.5% mRNA formulation after reconstitution as liquid aerosol; (iv) SD-0.5% mRNA formulation after reconstitution as liquid aerosol; (v) SFD-0.5% mRNA formulation as powder aerosol; (vi) SD-0.5% mRNA formulation as powder aerosol. All samples (except PBS) contained 5 µg of mRNA. At 24 h post-administration, the lung, liver, kidney and spleen tissue were isolated and the luciferase protein expression of the tissues was measured and the data was expressed at the mean value of relative light unit (RLU) per mg of protein±standard deviation (n=4-7).

Figure 20:
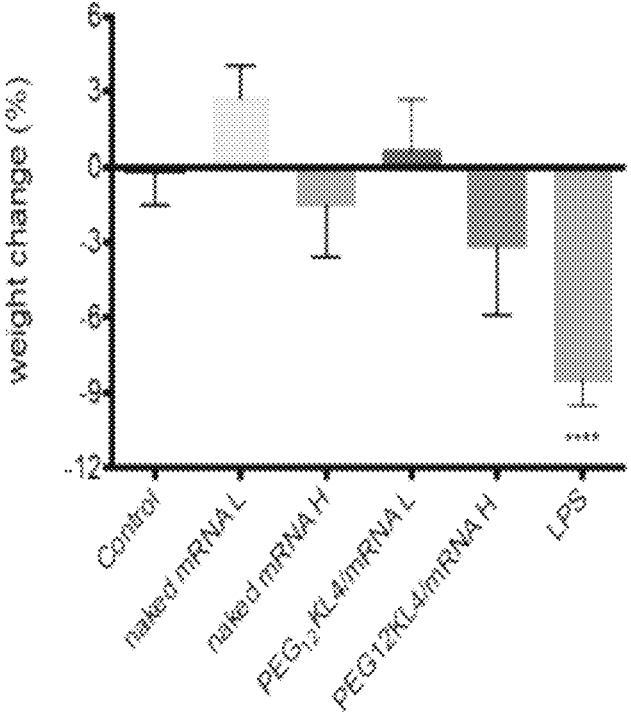

FIG. 20. Percentage of body weight change of BALB/c mice after administration of mRNA formulations. BALB/c mice were administered intratracheally with (i) PBS as control; (ii) naked mRNA L (low dose of 5 µg); (iii) naked mRNA H (high dose of 10 µg); (iv) $PEG_{12}$KL4/mRNA L (low dose of 5 µg); (v) $PEG_{12}$KL4/mRNA H (high dose of 10 µg); (vi) LPS (10 µg), in a final volume of 75 µL PBS. The body weight of the mice was measured before and 24 h after administration. Data are % body weight change expressed as mean±standard deviation (n=4-6). Statistical analysis was conducted by one-way ANOVA followed by Dunnett's post-hoc test as compared with control. ****p<0.0001.

Figure 21:
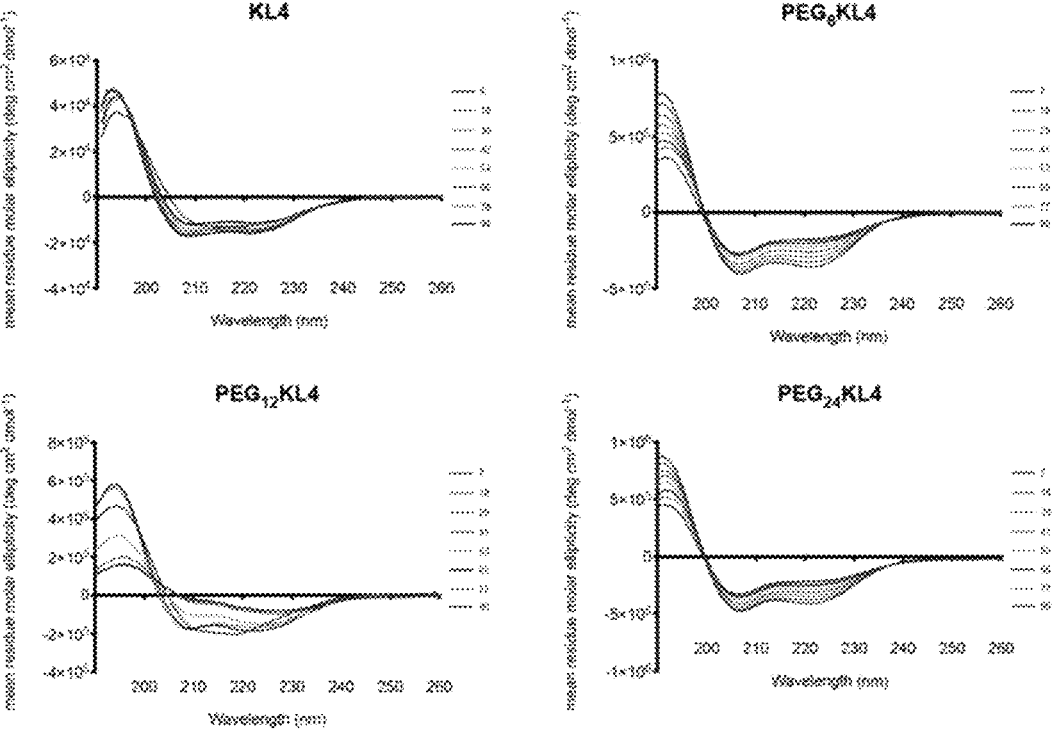

FIG. 21. Far-UV CD spectra of KL4, $PEG_6$KL4, $PEG_{12}$KL4 and $PEG_{24}$KL4 peptides measured at different temperatures from 6 to 94° C. The samples were prepared in 5 mM Tris-HCl buffer. Spectra were recorded from 190 to 260 nm using a 0.5 mm pathlength and were processed using Chirascan software where a spectrum of the peptide-free solution was subtracted and SavitzkyGorlay smoothing applied.

Figure 22A:
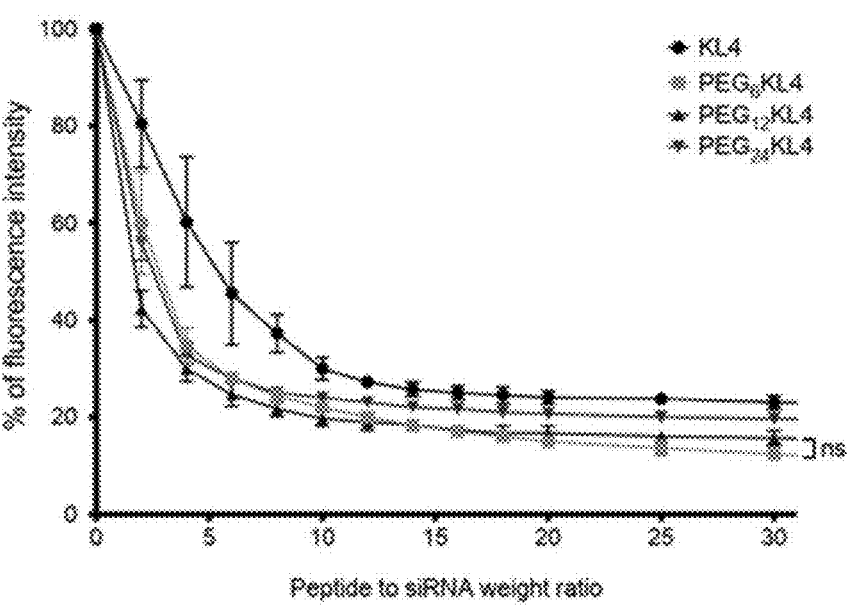
Figure 22B:
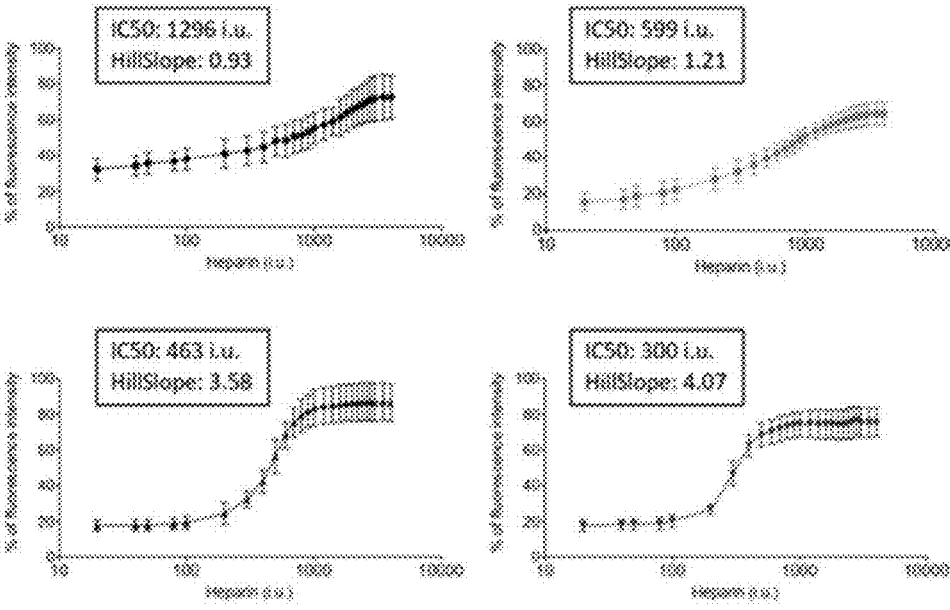

FIGS. 22A-22B. siRNA binding affinity of KL4, $PEG_6$KL4, $PEG_{12}$KL4 and $PEG_{24}$KL4 peptides using fluorescence displacement assay. (22A) Peptides were titrated to the siRNA/SYBR® Gold mixtures in Tris-acetate-EDTA (TAE) buffer, leading to a reduction of fluorescence intensity. Fluorescence intensity was plotted as percentage against peptide to siRNA ratios (w/w) upon titration (n=3). The data were analyzed by two-way ANOVA followed by Sidak post hoc test. All groups showed statistical difference with each other except $PEG_6$KL4 and $PEG_{12}$KL4. (22B) Peptide/siRNA complexes were formed at 10:1 ratio (w/w) in the presence of fluorescence dye. Heparin was titrated to dissociate the complexes and release the siRNA, leading to an increase in fluorescent intensity. Fluorescence intensity was plotted as a percentage against the amount of heparin upon titration (n=3). The data was fit to a fourparameter logistic sigmoidal curve and the $IC_{50}$ and hillslope were calculated.

Figure 23:
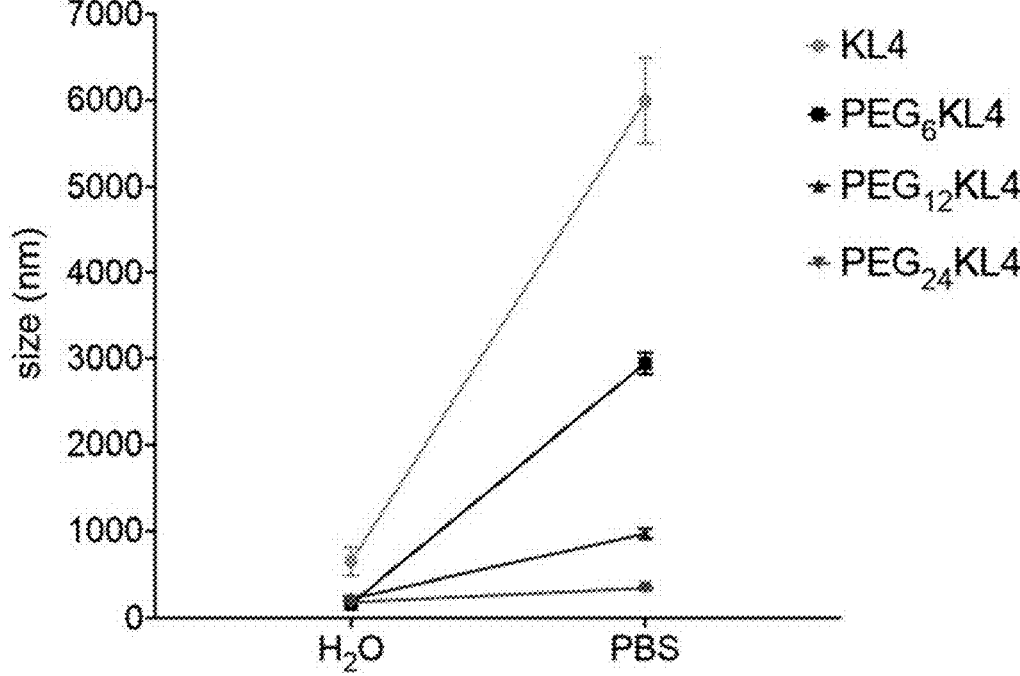

FIG. 23. The change of the particle size of KL4/siRNA, $PEG_6$KL4/siRNA, $PEG_{12}$KL4/siRNA and $PEG_{24}$KL4/siRNA complexes in the presence of phosphate buffer saline (PBS). Peptide/siRNA complexes were first formed in water at ratio 10:1 (w/w). PBS was added to the complexes to a final phosphate buffer concentration of 10 mM. The particle size was measured by dynamic light scattering after 30 min of incubation. The data was presented as mean±standard deviation (n=3).

Figures 24A, 24B:
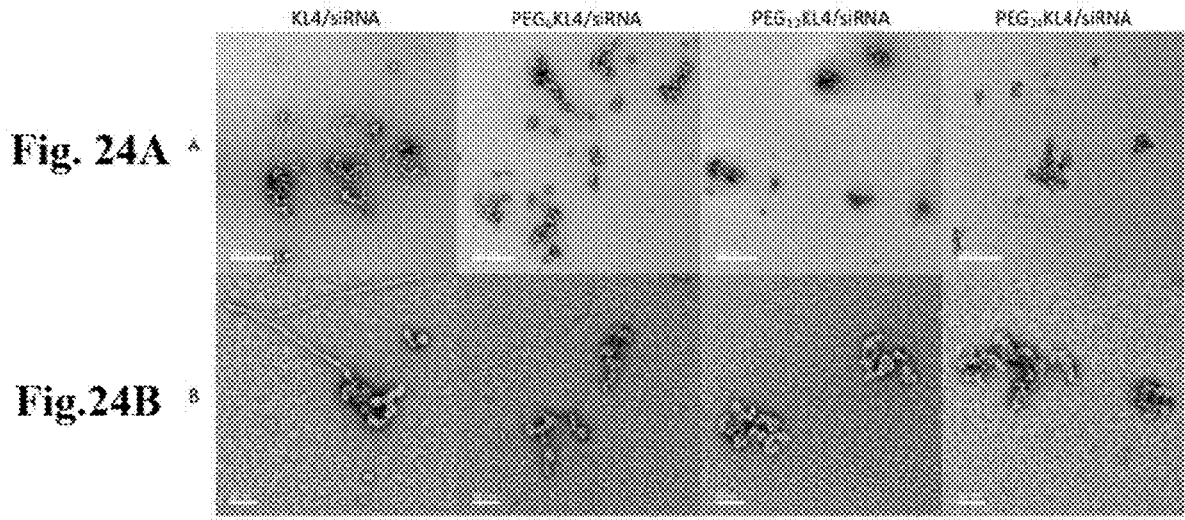

FIGS. 24A-24B. Transmission electron microscopy (TEM) images of KL4/siRNA, $PEG_6$KL4/siRNA, $PEG_{12}$KL4/siRNA and $PEG_{24}$KL4/siRNA complexes prepared at 10:1 ratio (w/w). The complexes were stained with 4% (w/v) uranyl acetate before imaging. (24A) Scale bar=200 nm and (24B) Scale bar=50 nm.

Figure 25A:
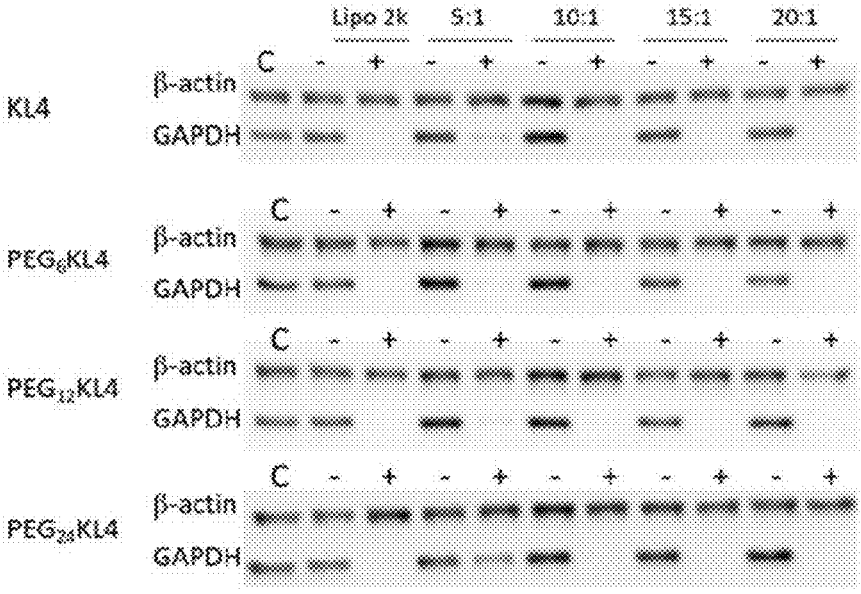
Figure 25B:
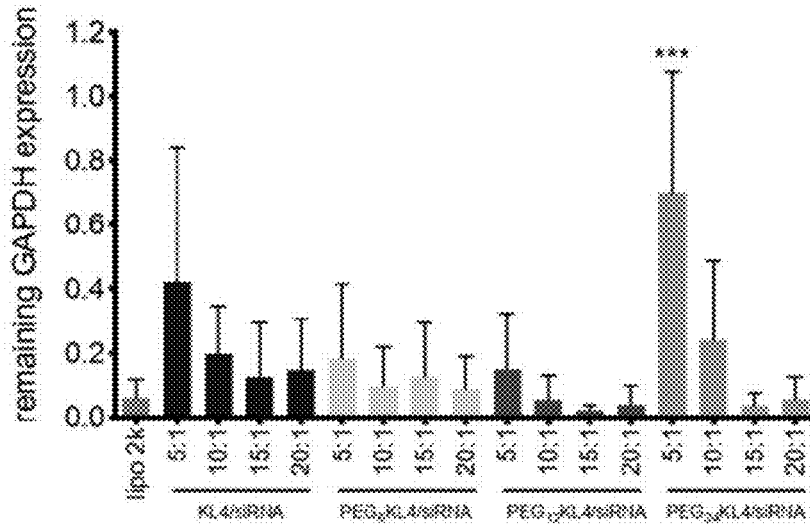

FIGS. 25A-25B. siRNA transfection on A549 cells. KL4/siRNA, $PEG_6$KL4/siRNA, $PEG_{12}$KL4/siRNA and $PEG_{24}$KL4/siRNA complexes were prepared at different ratios from 5:1 to 20:1 (w/w) with 50 pmol of GAPDH siRNA (+) or negative control siRNA (−) per well in a six-well plate (50 nM of siRNA). Lipofectamine 2000 (Lipo2k)/siRNA at 2:1 ratio (w/w) was used as positive control and cells in OptiMEM was used as negative control. (25A) Western blot analysis of GAPDH protein was performed at 72 h post-transfection with β-actin used as internal control. (25B) Densitometry results were shown as the mean±standard deviation of three independent repeats (n=3). The data were analyzed by one-way ANOVA followed by Dunnett's post hoc test as compared with Lipo2k, ***p<0.001.

Figure 26A:
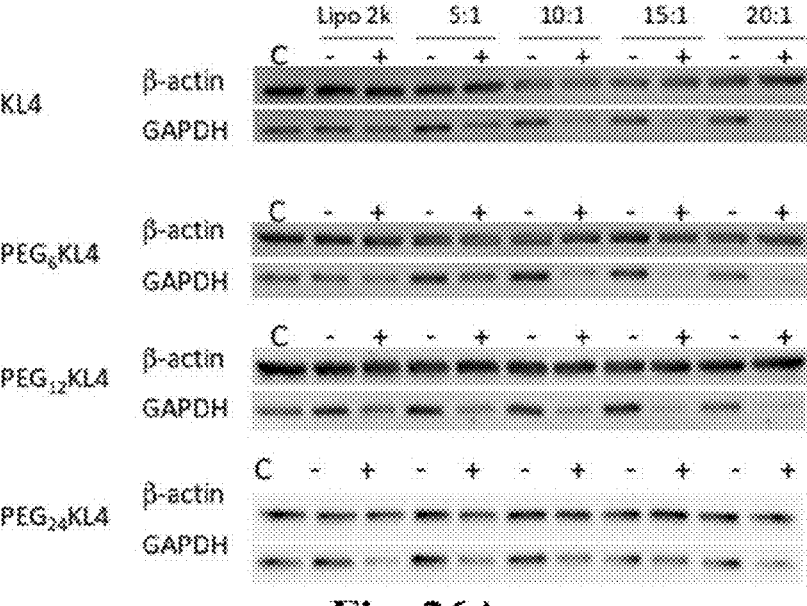
Figure 26B:
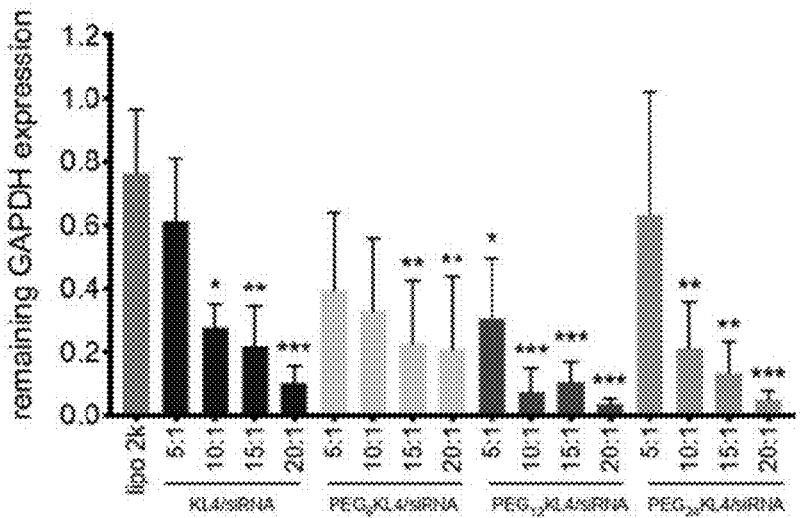

FIGS. 26A-26B. siRNA transfection on Calu-3 cells. KL4/siRNA, $PEG_6$KL4/siRNA, $PEG_{12}$KL4/siRNA and $PEG_{24}$KL4/siRNA complexes were prepared at different ratios from 5:1 to 20:1 (w/w) with 50 pmol of GAPDH siRNA (+) or negative control siRNA (−) per well in a six-well plate (50 nM of siRNA). Lipofectamine 2000 (Lipo2k)/siRNA at 2:1 ratio (w/w) was used as positive control and cells in OptiMEM was used as negative control. (26A) Western blot analysis of GAPDH protein was performed at 72 h post-transfection with β-actin used as internal control. (26B) Densitometry results were shown as the mean±standard deviation of three independent repeats (n=3). The data were analyzed by one-way ANOVA followed by Dunnett's post hoc test as compared with Lipo2k, *p<0.05. p<0.01,*p<0.001.

Figure 27A:
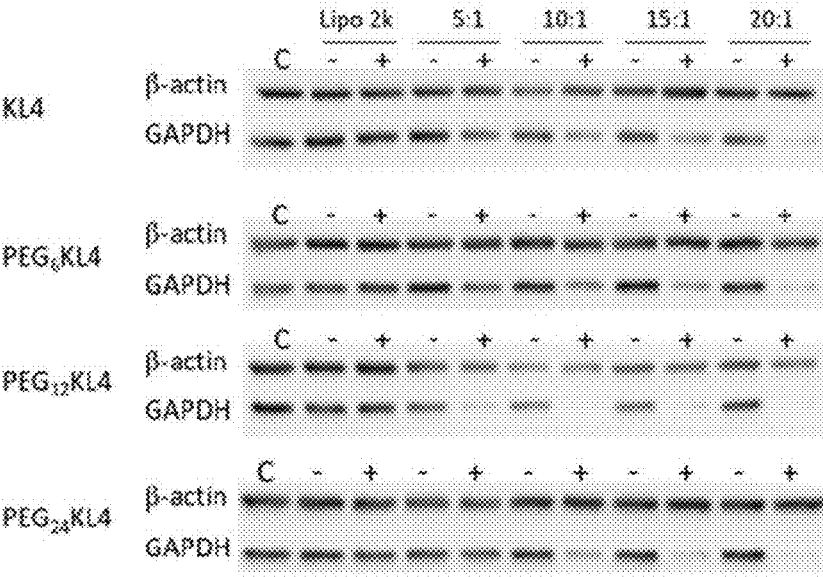
Figure 27B:
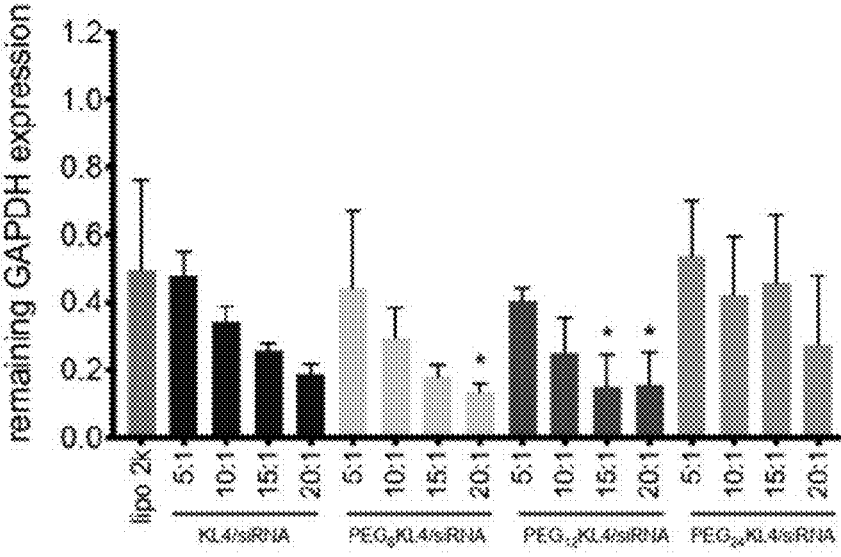

FIGS. 27A-27B. siRNA transfection on BEAS-2B cells. KL4/siRNA, $PEG_6$KL4/siRNA, $PEG_{12}$KL4/siRNA and $PEG_{24}$KL4/siRNA complexes were prepared at different ratios from 5:1 to 20:1 (w/w) with 50 pmol of GAPDH siRNA (+) or negative control siRNA (−) per well in a six-well plate (50 nM of siRNA). Lipofectamine 2000 (Lipo2k)/siRNA at 2:1 ratio (w/w) was used as positive control and cells in OptiMEM was used as negative control. (27A) Western blot analysis of GAPDH protein was performed at 72 h post-transfection with β-actin used as internal control. (27B) Densitometry results were shown as the mean±standard deviation of three independent repeats (n=3). The data were analyzed by one-way ANOVA followed by Dunnett's post hoc test as compared with Lipo2k, *p<0.05.

Figure 28A:
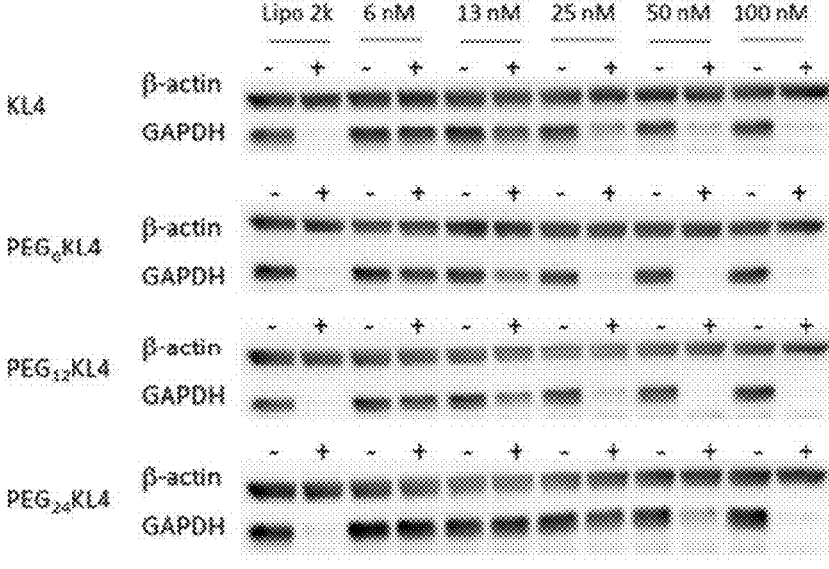
Figure 28B:
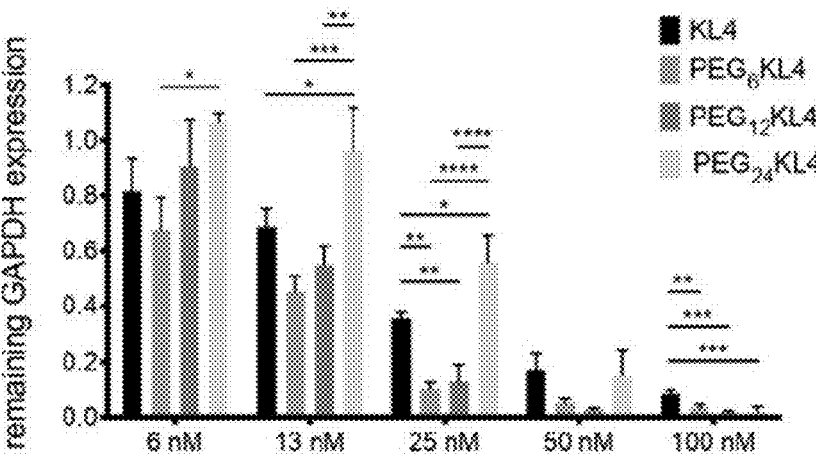

FIGS. 28A-28B. siRNA transfection in various siRNA concentration on A549 cells. KL4/siRNA, $PEG_6KL4/$ siRNA, $PEG_{12}KL4/siRNA$ and $PEG_{24}KL4/siRNA$ complexes were prepared at 10:1 ratio (w/w), and Lipofectamine 2000 (Lipo 2k)/siRNA complexes were prepared at 2:1 ratio (v/w). GAPDH siRNA (+) or negative control siRNA (−) were used for transfection at 6 pmol to 100 pmol per well (6 nM to 100 nM). (28A) Western blot analysis of GAPDH protein was performed at 72 h post-transfection, with β-actin used as internal control. (28B) Densitometry results were shown as the average of three independently repeated experiments (n=3). The data were analyzed by one-way ANOVA followed by Tukey's post-hoc test, *p<0.05, p<0.01, *p<0.001, ****p<0.0001.

FIGS. 29A-29D. Cellular uptake study of KL4/siRNA, $PEG_6KL4/siRNA$, $PEG_{12}KL4/siRNA$ and $PEG_{24}KL4/$ siRNA complexes using flow cytometry. (29A and 29B) A549 cells and (29C and 29D) Calu-3 cells were treated with peptide/siRNA complexes at 10:1 ratio (w/w) containing 150 pmol fluorescently labelled siRNA per well in a six-well plate in OptiMEM. The extracellular florescence signal was quenched with 0.04% (w/v) trypan blue solution and the fluorescence intensity of cells was measured at 4 h post-transfection. (29A and 29C) Percentage of cells with siRNA uptake. (29B and 29D) Median fluorescence intensity of the cells. Values are the mean±standard deviation. The data was analyzed by one-way ANOVA followed by Tukey's post hoc test, p<0.01, **p<0.0001 (n=3).

Figures 30A, 30B:
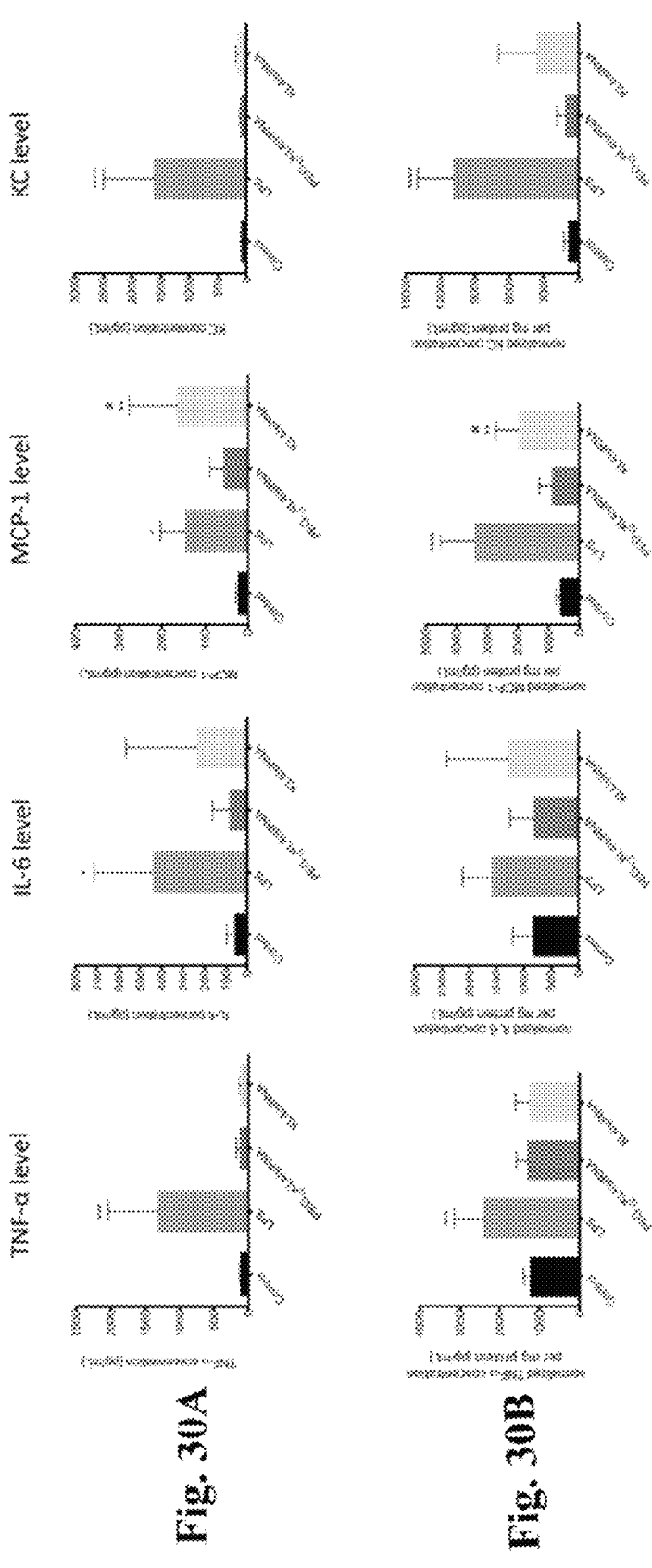

FIGS. 30A-30B. Level of pro-inflammatory cytokines following pulmonary delivery of siRNA. BALB/c mice were administered intratracheally with PBS as control; LPS (10 µg); $PEG_{12}KL4/siRNA$ (100 µg/10 µg) or KL4/siRNA (100 µg/10 µg), all in a final volume of 75 µl PBS except LPS, which was prepared in 25 µL of PBS. At 24 h postadministration, cytokines and chemokines levels in (30A) bronchoalveolar lavage fluid (BALF) and (30B) lung homogenates were detected by ELISA. Data are expressed as mean±SD (n=6-7). Statistical analysis was conducted by one-way ANOVA (Tukey's post hoc test). *p<0.05, p<0.01, *p<0.001, ****p<0.0001 as compared with control group treated with PBS; #p<0.05 as compared with $PEG_{12}KL4/siRNA$ group.

Figure 31:
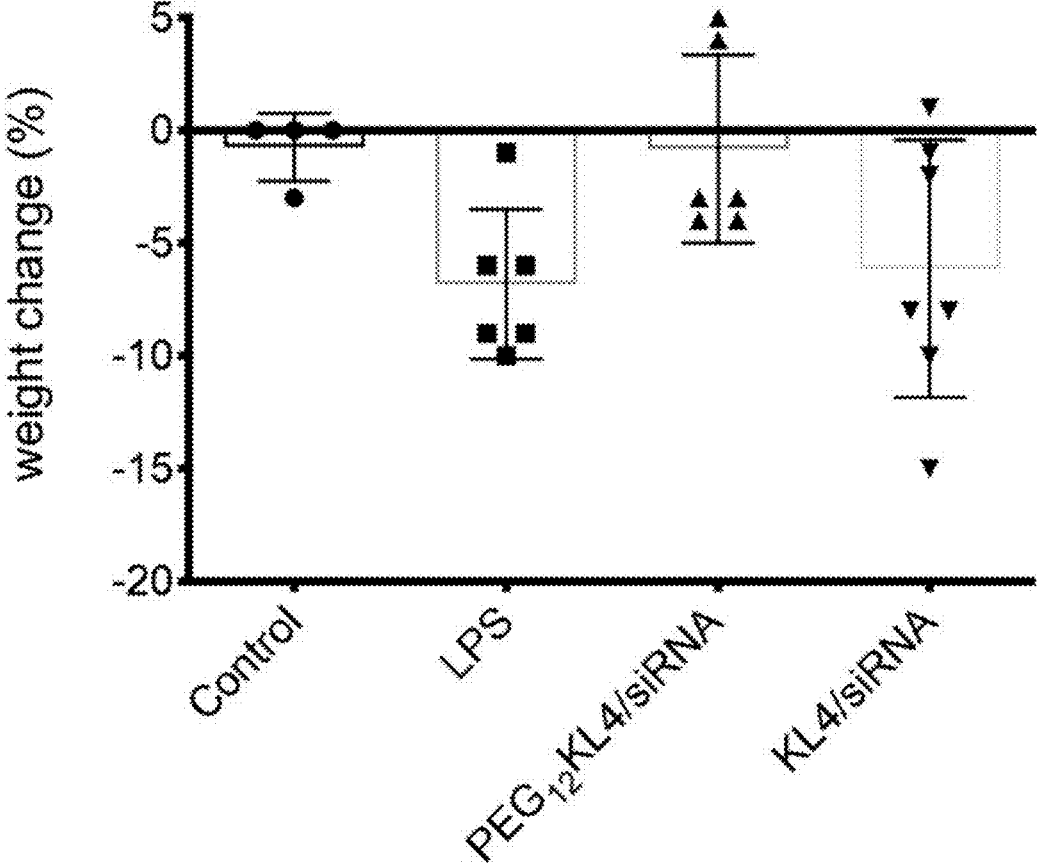

FIG. 31. Change of body weight of the mice. BALB/c mice were administered intratracheally with PBS as control; LPS (10 µg); $PEG_{12}KL4/siRNA$ (100 µg/10 µg) or KL4/siRNA (100 µg/10 µg), all in a final volume of 75 µl PBS, except LPS which was prepared in 25 µL of PBS. The body weight of the mice was monitored before and 24 h postadministration. The data was presented as mean value of percentage of weight change±standard deviation (n=4-7).

Figure 32:
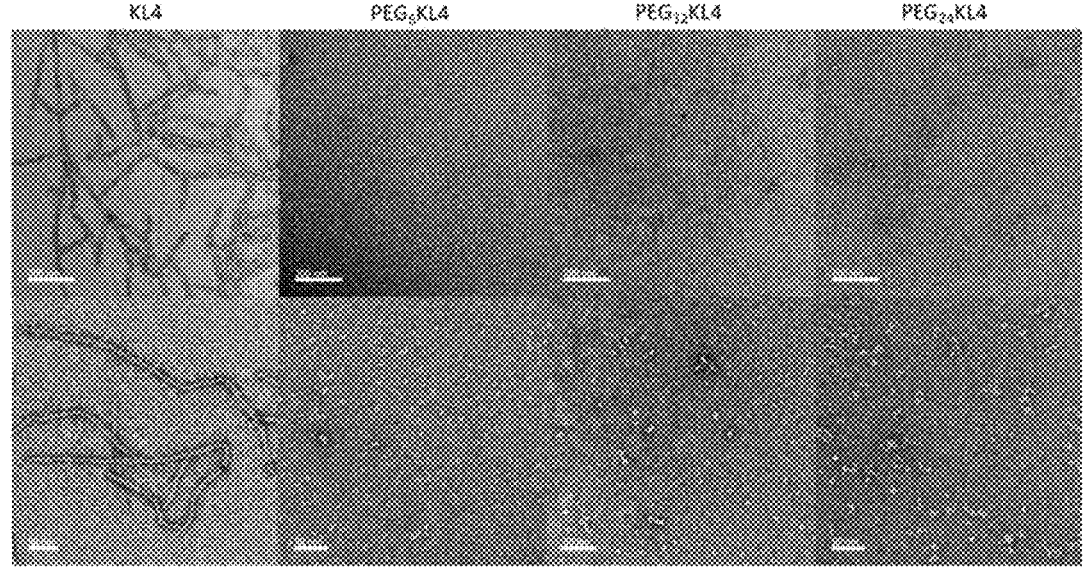

FIG. 32. Transmission electron microscopy (TEM) images of KL4, $PEG_6KL4$, $PEG_{12}KL4$ and $PEG_{24}KL4$ peptides prepared at 0.5 mg/mL. The complexes were stained with 4% (w/v) uranyl acetate before imaging. Scale bar=200 nm (upper panel) and 50 nm (lower panel).

Figures 33A, 33B:
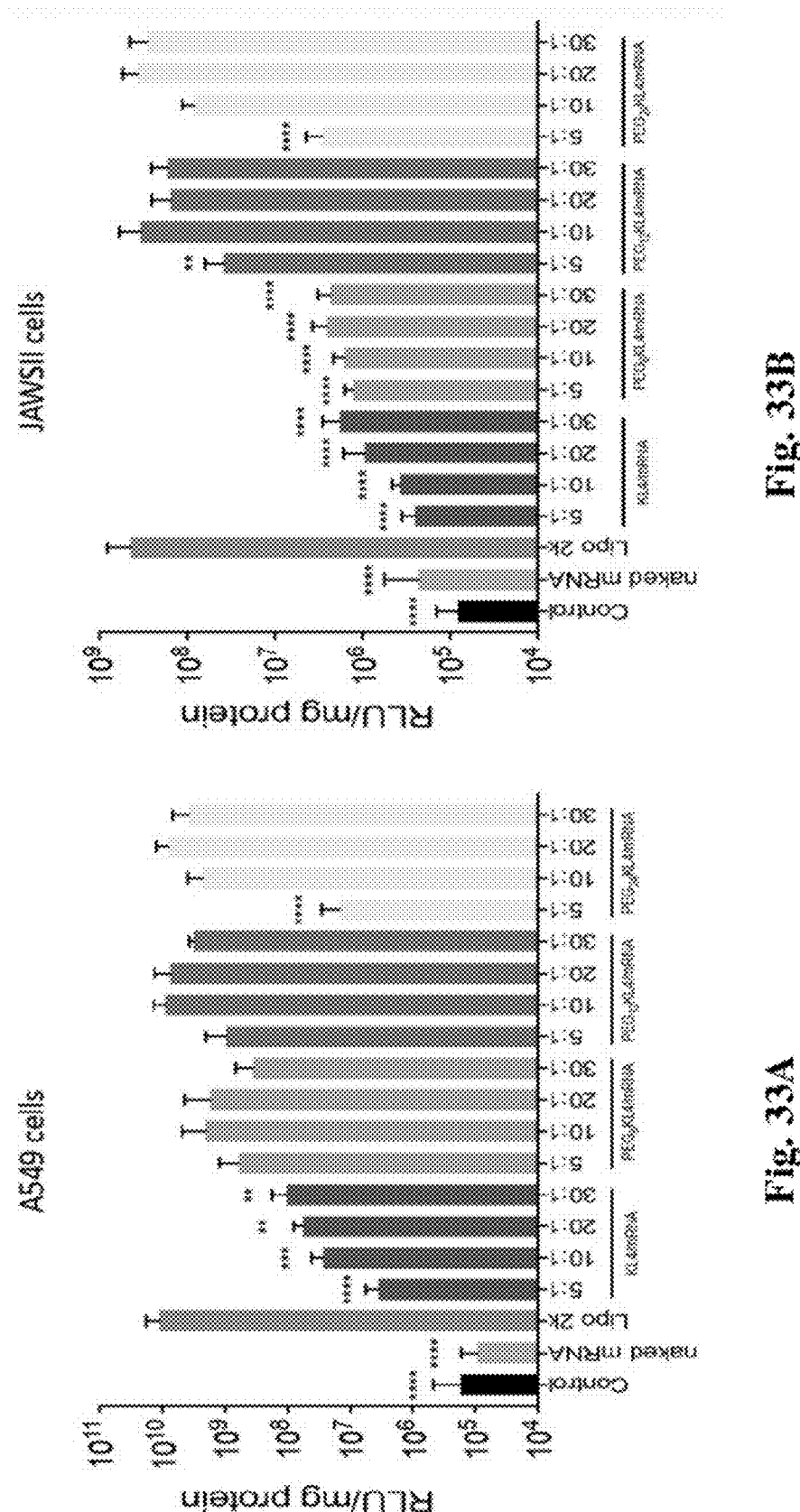

FIGS. 33A-33B. mRNA (luciferase) transfection on (33A) A549 cells; and (33B) JAWSII cells. KL4/mRNA, $PEG_6KL4/mRNA$, $PEG_{12}KL4/mRNA$ and $PEG_{24}KL4/$ mRNA complexes were prepared at 5:1 to 30:1 ratios (w/w) with 1 µg of mRNA in a 24-well plate. Untreated cells, naked mRNA and Lipofectamine 2000 (Lipo2K)/mRNA complexes (2:1 w/w) were used as controls. Luciferase expression was measured at 24 h post-transfection. The data was expressed as the mean value of relative light unit (RLU)

per mg of protein±standard deviation (n=3). The data were analyzed by one-way ANOVA followed by Dunnett's post hoc test as compared with lipo2k, p<0.01,*p<0.001, ****p<0.0001.

FIG. 34. Comparison of mRNA transfection efficiency within the same peptide prepared at different peptide to mRNA ratios, and comparison between different peptides prepared at the same peptide to mRNA ratios. The data were analyzed by one-way ANOVA followed by Tukey's post hoc test, n.s. not significant, *p<0.05, p<0.01, *p<0.001, ****p<0.0001.

Figures 35A, 35B:
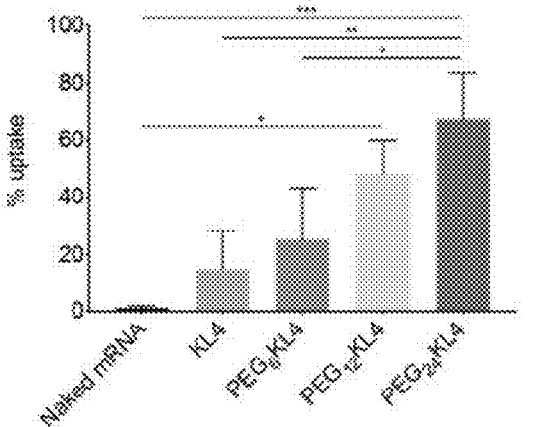

FIGS. 35A-35B. Cellular uptake study using flow cytometry. A549 cells were treated with naked mRNA, $PEG_6KL4/$ mRNA, $PEG_{12}KL4/mRNA$ and $PEG_{24}KL4/mRNA$ complexes prepared at 10:1 ratio (w/w) with cyanine-5 labeled mRNA. Cells were examined at 4 h post-transfection using flow cytometry—(35A) percentage of cells with mRNA uptake; and (35B) median fluorescence intensity of the cells. Values are the mean±standard deviation. The data was analyzed by one-way ANOVA followed by Tukey's post-hoc test. *p<0.05, p<0.01, *p<0.001 (n=3).

Figure 36:
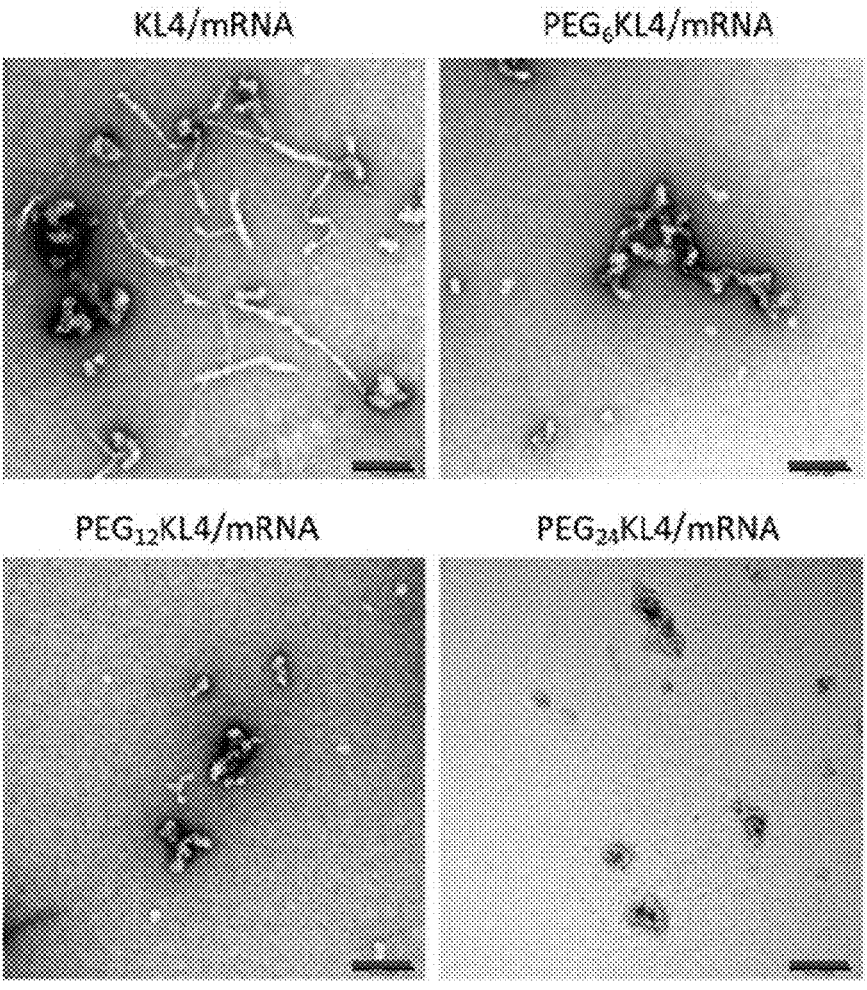

FIG. 36. Transmission electron microscopy (TEM) images of KL4/mRNA, $PEG_6KL4/mRNA$, $PEG_{12}KL4/$ mRNA and $PEG_{24}KL4/mRNA$ complexes prepared at 10:1 ratio (w/w). The complexes were stained with 4% (w/v) uranyl acetate before imaging. Scale bar=100 nm.

Figure 37:
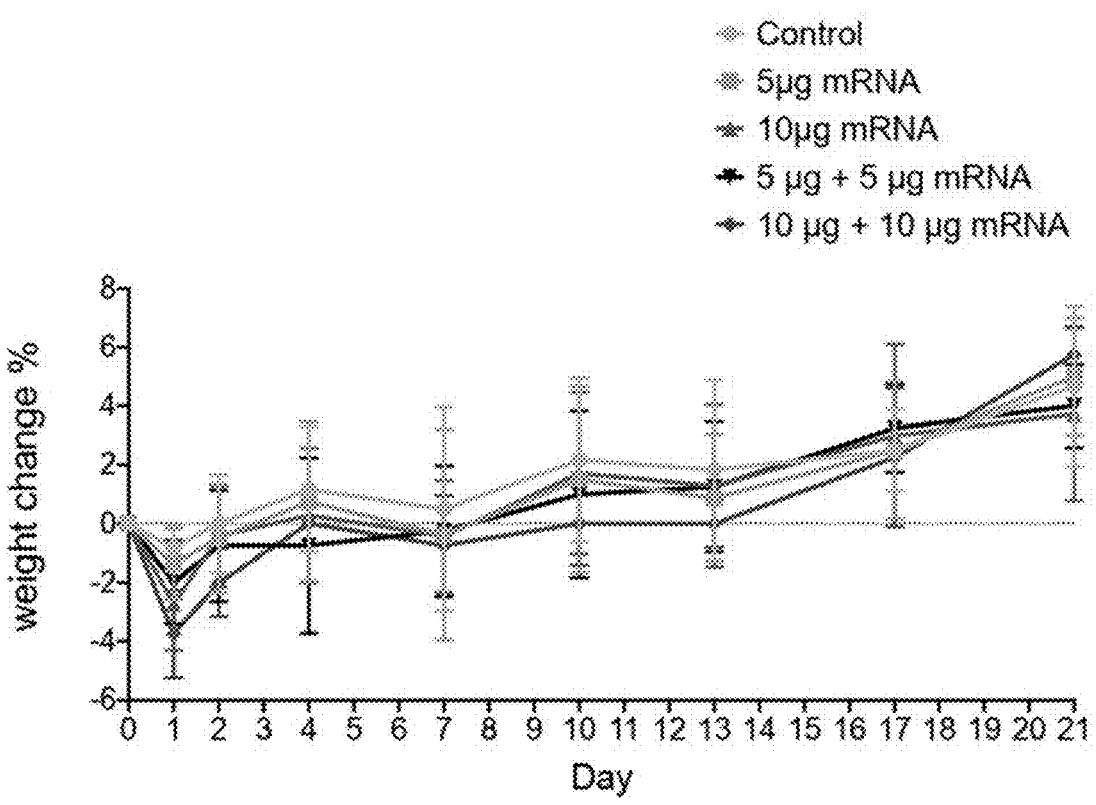

FIG. 37. Long term in vivo safety of $PEG_{12}KL4/mRNA$ complexes. BALB/c mice were administered intratracheally of $PEG_{12}KL4/mRNA$ complexes prepared at 10:1 ratio (w/w) in 75 µL PBS containing 5 µg or 10 µg of mRNA per mice once or twice (with 3 weeks apart), using MicroSprayer (Penn Century). PBS was used as control. The body weight of the mice was monitored before and 21 days post-administration. The data was presented as mean value of percentage of weight change±standard deviation (n=4-8).

Figure 38:
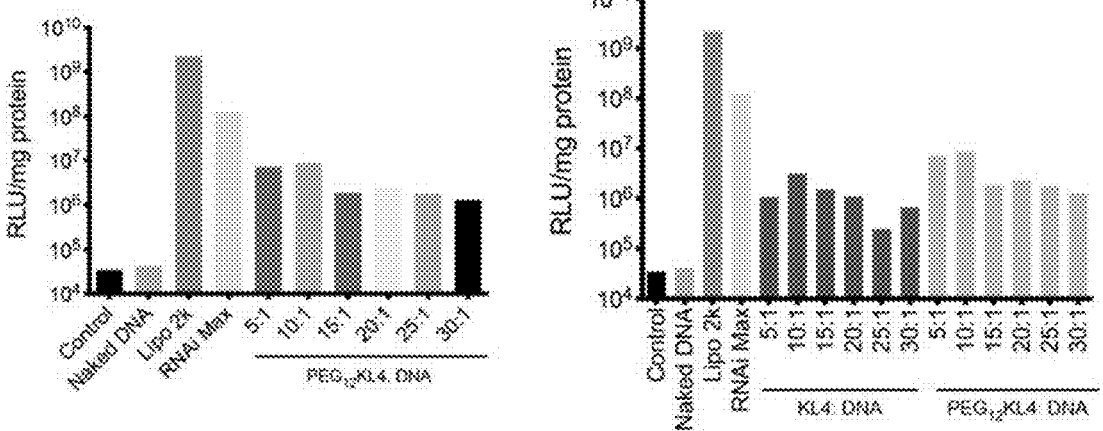

FIG. 38. DNA (luciferase) transfection on A549 cells. KL4/DNA and $PEG_{12}KL4/DNA$ complexes were prepared at 5:1 to 30:1 ratios (w/w) with 1 µg of DNA in a 24-well plate. Untreated cells, naked DNA and Lipofectamine 2000 (Lipo2K)/DNA complexes (2:1 w/w), RNAiMax/DNA complexes (2:1 w/w) were used as controls. Luciferase expression was measured at 24 h post-transfection.

FIG. 39. The mRNA dry powders were reconstituted and added to the cells at 1 µg mRNA per well in a 24-well plate. Naked mRNA, Lipofectamine 2000 (Lipo2k)/mRNA complexes (2:1 w/w ratio) and freshly prepared $PEG_{12}KL4/$ mRNA complexes (10:1 w/w ratio) were used as controls. Luciferase expression was measured at 24 h post-transfection. The data was expressed as the mean value of relative light unit (RLU) per mg of protein±standard deviation (n=3). The data were analyzed by one-way ANOVA followed by Dunnett's post-hoc test, *p<0.05, p<0.01, **p<0.0001 as compared with freshly prepared $PEG_{12}KL4/mRNA$ complexes.

5. DETAILED DESCRIPTION

The translation of mRNA therapeutics for the treatment of lung diseases is hindered by the lack of a safe and effective mRNA delivery system with good stability for pulmonary delivery. Provided herein is an inhalable dry powder formulation of mRNA. In one embodiment, the dry powder aerosol formulation of mRNA is administered directly to the lungs to induce the expression of target protein in vivo. In one embodiment, the formulation comprises: (i) mannitol as bulking agent; (ii) a synthetic PEGylated KL4 peptide as transfection agent; and (iii) mRNA for protein expression. In certain embodiments, the method of making the dry powder formulation comprises spray drying or spray freeze drying. The dry powder formulation that are suitable for inhalation, while the biological activity of the mRNA is successfully preserved. An additional advantage of dry powder formulation of mRNA is the better stability over liquid aerosol.

In one embodiment, provided herein is a dry powder formulation comprises of: (i) PEGylated KL4 peptide which is synthetic peptide to mediate efficient mRNA transfection in vivo; (ii) using spray drying or spray freeze drying techniques to produce inhalable powder formulation to improve formulation stability. The PEGylation of KL4 peptide can improve the water solubility and reduce the immunogenicity of the peptide, making it a safe and effective nucleic acid delivery agent.

In one embodiment, provided herein is a novel RNA delivery vector, $PEG_{12}KL4$ peptide, in which the synthetic cationic KL4 peptide is attached to a monodisperse linear PEG of 12-mers. In one embodiment, the $PEG_{12}KL4$ forms nano-sized complexes with mRNA at 10:1 ratio (w/w) through electrostatic interaction and mediated effective transfection on human lung epithelial cells.

In certain embodiments, $PEG_{12}KL4$/mRNA complexes are formulated into dry powder by spray drying (SD) and spray freeze drying (SFD) techniques. Both SD and SFD powder exhibited satisfactory aerosol properties for inhalation, with mass median aerodynamic diameter (MMAD) of 4.5 μm and 1.5 μm, respectively. In certain embodiments, the biological activity of the $PEG_{12}KL4$/mRNA complexes is preserved after drying. In one embodiment, the dry powder aerosol formulation comprises: (i) mannitol as bulking agent; (ii) $PEG_{12}KL4$ as transfection agent; and (iii) mRNA for protein expression.

In certain embodiments, the spray drying and spray freeze drying techniques are used to produce inhalable powder formulation of PEGylated KL4/mRNA system. The powder produced is in the suitable aerodynamic diameter range for effective lung deposition (aerodynamic diameter <5 μm) and good powder dispersion property (fine particle fraction>40% in cascade impactor study). In one embodiment, the length of PEG used for the PEGylation is about 5-10, 10-15, 15-20, 20-25, 25-30 units of PEG. In certain embodiments, the length of PEG is 6, 7, 8, 9, 10, 11, 12, 13, 14, 15, 16, 17, 18, 19, 20, 21, 22, 23, 24, 25 units of PEG. In one embodiment, the PEG is monodispersed. In one embodiment, the PEG is a 12 unit in length. In one embodiment, the PEG is about 600 Da. In certain embodiments, the presently disclosed delivery system is used for mRNA vaccines (e.g. influenza) delivery. In certain embodiment, the present mRNA delivery system is used for the treatment of lung diseases (e.g. cystic fibrosis, lung inflammatory diseases). In certain embodiment, the delivery system is administered via inhalation or nasal administration.

6. EXAMPLES: MATERIALS AND METHODS

6.1 Materials

KL4 peptide (KLLLLKLLLLKLLLLKLLLLK-NH2 (SEQ ID NO: 1)) was purchased from ChinaPeptides (Shanghai, China). $PEG_{12}KL4$ peptide (with monodisperse dodecaethylene glycol, $PEG_{12}$) was purchased from EZBiolab (Carmel, NJ, USA) with purity>90%. The KL4 peptide stock solution was prepared at 1 mg/mL in 1% (v/v) DMSO. The $PEG_{12}KL4$ stock solution was prepared at 2 mg/mL in distilled water. CleanCap® firefly luciferase mRNA and cyanine-5 EGFP mRNA were purchased from TriLink Bio Technologies (San Diego, CA, USA). The luciferase mRNA stock solution was prepared at 1 mg/mL in 1 mM sodium citrate buffer. Dulbecco's modified Eagle's medium (DMEM), Keratinocyte-SFM, Roswell Park Memorial Institute (RPMI) 1640, OptiMEM I reduced serum medium, trypsin-EDTA (0.25%), Fetal Bovine Serum (FBS), Antibiotic-Antimycotic (100×), Lipofectamine 2000, DNA Gel Loading Dye (6×), Hoechst 33258 were purchased from Thermo-Fisher Scientific (Waltham, Massachusetts, USA). GelRed nucleic acid stain was purchased from Biotium (Hayward, CA, USA). The luciferase assay system and beetle luciferin potassium salt were purchased from Promega (Madison, WI, USA). Mouse tumor necrosis factor-alpha (TNF-α), monocyte chemoattractant protein-1 (MCP-1), and interleukin-6 (IL-6) ELISA kits were purchased from R&D Systems (Minneapolis, MN, USA). Mannitol (Pearlitol 160C) was obtained from Roquette (Lestrem, France). Lipopolysaccharide (LPS) from E. coli O111:B4 was purchased from Sigma-Aldrich (St. Louis, MO, USA). Other reagents were obtained from Sigma-Aldrich (Saint Louis, MO, USA) as analytical grade or better.

6.2 Gel Retardation Assay

The gel retardation assay was carried out to examine the mRNA binding affinity of the KL4 and $PEG_{12}KL4$ peptides. Both KL4/mRNA and $PEG_{12}KL4$/mRNA complexes were prepared at 0.5:1 to 10:1 peptide to mRNA ratios (w/w), with 1 μg of mRNA in 10 μL of TAE buffer. The complexes were incubated at room temperature for 30 min, followed by the addition of 2 μL of gel loading dye. The complexes were loaded into a 2% (w/v) agarose gel stained with GelRed. Electrophoresis was run in TAE buffer at 125 V for 25 min. The gel was visualized under UV illumination. For the mRNA release study, both KL4/mRNA and $PEG_{12}KL4$/mRNA complexes were prepared at 10:1 ratio (w/w). At 30 min after complexes formation, different concentrations of sodium dodecyl sulfonate (SDS) solution from 1 mM to 8 mM were added, and the mixtures were incubated at room temperature for 30 min. The samples were loaded into an agarose gel and electrophoresis was performed as described above.

6.3 Particle Size and Zeta Potential Measurement

For particle size measurement, KL4/mRNA and $PEG_{12}KL4$/mRNA complexes were prepared at 10:1 ratio (w/w) with 4 μg of mRNA in 100 μL of ultrapure water. At 30 min after complexes formation, the hydrodynamic size was measured by dynamic light scattering (Delsa™ Nano C, Beckman Coulter, CA, USA). For zeta potential measurement, the KL4/mRNA and $PEG_{12}KL4$/mRNA complexes were prepared at 10:1 ratio (w/w) with 20 μg of mRNA in 500 μL of 2% PBS. At 30 min after complexes formation, the zeta potential was measured in a flow cell using electrophoretic light scattering (Delsa™ Nano C, Beckman Coulter, CA, USA). The size and zeta potential of $PEG_{12}KL4$/mRNA complexes in the SD and SFD powder formulations were also measured after reconstitution.

6.4 Cell Culture

A549 cells (human alveolar epithelial adenocarcinoma), BEAS-2B cells (human bronchial epithelial cells) and THP-1 cells (human monocyte) were obtained from ATCC (Manassas, VA, USA). A549 cells were cultured in DMEM supplemented with 10% (v/v) FBS and 1% (v/v) antibiotic-antimycotic. BEAS-2B cells were cultured in Keratinocyte-SFM supplemented with human recombinant Epidermal Growth Factor (rEGF), Bovine Pituitary Extract (BPE), and 1% (v/v) antibiotic-antimycotic. THP-1 cells were cultured in RPMI-1640 supplemented with 10% (v/v) FBS and 1%

(v/v) antibiotic-antimycotic. All the cells were maintained at 5% $CO_2$, 37° C., and subcultured according to ATCC instruction.

6.5 mRNA Transfection In Vitro

A549 cells and BEAS-2B cells were seeded in 24-well plates at a density of $0.5 \times 10^5$ and $1 \times 10^5$ cells per well, respectively, for overnight. The KL4/mRNA and $PEG_{12}KL4$/mRNA complexes formed at 5:1 to 30:1 ratio (w/w) in OptiMEM I reduced serum medium were added to the cells at 0.5 or 1 μg mRNA per well. Naked mRNA and lipoplexes (Lipofectamine 2000/mRNA complexes) were used as controls. After 4 h of incubation, the transfection medium was replaced with serum supplemented cell culture medium. At 24 h post-transfection, the cells were washed and lysed with reporter cell lysis buffer. The luciferase expression was detected using the luciferase assay system according to the manufacturer's protocol. The luminescence was measured with luminometer (SpectraMax L Microplate Reader, Molecular devices, CA, USA) and the protein concentrations of the cell lysates were quantified by Bradford protein assay. The results were expressed as relative light unit (RLU) per mg of total protein. To study the transfection efficiency of $PEG_{12}KL4$/mRNA in SD and SFD powder formulations, the powders were reconstituted before adding to the cells. The luciferase expression was examined at 24 h post-transfection as described above.

6.6 Cellular Uptake Study

The cellular uptake of the mRNA was studied by flow cytometry and confocal microscopy. For the flow cytometry study, A549 cells were seeded in 24-well plates at a density of $0.5 \times 10^5$ cells per well one day before the experiment. The cells were transfected with naked mRNA, KL4/mRNA and $PEG_{12}KL4$/mRNA complexes at 10:1 ratio (w/w) in OptiMEM I reduced serum medium containing 1 μg of cyanine-5 labelled EGFP mRNA per well. After 4 h of incubation, the cells were washed and trypsinized. Cells from three separate wells of the same treatment were combined and suspended in culture medium. The extracellular florescent signal was quenched with 0.04% (w/v) trypan blue solution. After 2 min, the cells were washed, resuspended in 300 μL of PBS and sieved with a sterile 40 μm cell strainer (BD Biosciences, CA, USA). The fluorescence intensity was analyzed by flow cytometry (BD FACSCantoII Analyzer, BD Biosciences, CA, USA). At least $1 \times 10^4$ single cells were analyzed for each sample. For the confocal study, A549 cells were seeded in a 35 mm Mattek glass bottom culture dish (Mattek Corp. Ashland, MA, USA) at a density of $1 \times 10^5$ cells per well one day before imaging. Naked mRNA, KL4/mRNA and $PEG_{12}KL4$/mRNA complexes at 10:1 ratio (w/w) were prepared in Opti-MEM I reduced serum medium with 2 μg of cyanine-5 labelled mRNA per dish. After 3.5 h of incubation with the cells, the transfection medium was removed and replaced with fresh culture medium. Hoechst stain (5 μg/mL) was added to the cells for nuclei staining. After 30 min of incubation, the cells were washed and visualized at 4 h post-transfection by the confocal laser scanning microscope (Zeiss LSM 780 inverted microscope, Jena, Germany).

6.7 In Vitro Immunogenicity Study

THP-1 cells were seeded in 24-well plates at $2 \times 10^5$ cells per well. Cells were differentiated (into macrophage-like cells) with 100 nM phorbol 12 myristate 13-acetate (PMA) for 48 h. A549 cells were seeded in 24-well plates at $1 \times 10^5$ cells per well. Before the experiment, the cells were starved overnight with fresh medium supplemented with 1% FBS. The cells were then incubated with $PEG_{12}KL4$/mRNA complexes prepared at 10:1 ratio (w/w) containing 0.25 to 2 μg mRNA per well in OptiMEM I reduced serum medium. The level of TNF-α, MCP-1, and IL-8 secreted in cell medium were measured by ELISA at 24 h post-transfection. Untreated cells and cells treated with LPS (at 10 and 100 ng/mL for THP-1 cells; at 10 and 100 μg/mL for A549 cells) were used as negative and positive controls, respectively.

6.8 Preparation of Dry Powder Formulations $PEG_{12}KL4$/mRNA complexes were prepared at 10:1 ratio (w/w) in ultrapure water. Mannitol (as bulking excipient) was dissolved in water and added to the complexes after 30 min of incubation. The SD and SFD formulations were prepared at 1.5% and 3% (w/v) solute concentrations, respectively, with mRNA concentrations at 0.1% or 0.5% (w/w). Mannitol-only formulations were prepared for comparison. The operation parameters for SD and SFD were optimized in our previous studies [19, 20]. For the preparation of SD powder, the solutions were spray dried using a laboratory scale spray dryer with a high performance cyclone in suction mode and closed loop configuration (Mini Spray Dryer B-290 and Dehumidifier B-296; Büchi Labortechnik, Flawil, Switzerland) under the following operating conditions: inlet temperature of 80° C. (outlet temperature of around 50° C.), rate of aspiration at 90% (approximately 35 $m^3$/h), liquid feed rate of 1.4 mL/min and compressed air atomization flow rate at 742 L/h. A two-fluid nozzle with an internal diameter of 0.7 mm was used (Buchi stainless steel two-fluid nozzle, Switzerland). For the preparation of SFD powder, the solutions were transferred into a syringe and atomized by the two-fluid nozzle with nitrogen gas flow rate of 601 L/h. The liquid feed rate was controlled by a syringe pump at 1.5 mL/min. The atomized liquid droplets were frozen and collected in liquid nitrogen, and the samples were subjected to freeze drying (FreeZone® 6 Liter Benchtop Freeze Dry System with Stoppering Tray Dryer, Labconco Corporation, MO, USA) in which the samples were kept under vacuum (chamber pressure below 0.133 mBar) at −25° C. for 40 h, followed by a secondary drying at 20° C. for 20 h. All the dried powders were collected in glass vials and stored in a desiccator with silica gel at ambient temperature until further analysis. One batch of powder was prepared for each formulation. A summary of the drying methods, composition and production yield of all the dry powder formulations was shown in Table 1.

TABLE 1

Summary of spray dried (SD) and spray freeze dried (SFD) formulations of $PEG_{12}KL4$/mRNA complexes (at 10:1 ratio). Mannitol-only formulations were also prepared as controls.

| Formulation | Drying method | % by weight (w/w) | | | % Production yield |
| --- | --- | --- | --- | --- | --- |
| | | mRNA | $PEG_{12}KL4$/ mRNA | Mannitol | |
| SD-Mannitol | SD | 0 | 0 | 100 | 45.8 |
| SD-0.1% mRNA | | 0.1 | 1 | 98.9 | 75.8 |
| SD-0.5% mRNA | | 0.5 | 5 | 94.5 | 59.0 |
| SFD-Mannitol | SFD | 0 | 0 | 100 | 84.7 |
| SFD-0.1% mRNA | | 0.1 | 1 | 98.9 | 78.0 |
| SFD-0.5% mRNA | | 0.5 | 5 | 94.5 | 82.2 |

6.9 Morphology and Aerosol Performance of Powder Formulations

The morphology of SD and SFD powders was visualized using field emission scanning electron microscopy (SEM; Hitachi S-4800 FEG, Hitachi, Tokyo, Japan). Powder samples were sprinkled onto carbon adhesive tape that was mounted on SEM stubs. Excess powders were removed by blowing with clean compressed air. Prior to imaging, the powders were sputter coated with approximately 11 nm gold-palladium alloy in two cycles to avoid overheating. The aerosol performance of the powder formulations was evaluated by the Next Generation Impactor (NGI; Copley, Nottingham, UK) in accordance to the British Pharmacopoeia (2016) [21]. For each dispersion, approximately 8.5±0.5 mg and 5.0±0.5 mg of SD and SFD powders, respectively, were loaded in a size 3 hydroxypropyl methylcellulose capsule (Capsugel, West Ryde, NSW, Australia), which was placed in a Breezhaler® (Novartis Pharmaceuticals, Hong Kong). The flow rate and dispersion duration were 90 L/min and 2.7 s, respectively. Prior to each dispersion, a thin layer of silicon grease (LPS Laboratories, Illinois, GA, USA) was coated onto the impactor stages to reduce particle bounce. After dispersion, the powders deposited on the inhaler and NGI stages were collected by rinsing with 4 mL of ultrapure water. Recovered dose was defined as the sum of powder mass assayed on inhaler and all NGI stages in a single run, as calculated with the assayed mannitol obtained from the liquid chromatography (which is described in the next section). The emitted fraction (EF) referred to the fraction of powder that exited the inhaler with respect to the recovered dose. Fine particle fraction (FPF) was the fraction of powder with aerodynamic diameter <5.0 µm with respect to the recovered dose. The mass median aerodynamic diameter (MMAD) together with the geometric standard deviation (GSD) were calculated based on the NGI results using the method modified from an online calculator (www.mmadcalculator.com/).

6.10 High Performance Liquid Chromatography (HPLC)

The amount of mannitol (which contributed to at least 94.5% by mass in all formulations) in the dispersed samples of NGI was quantified using HPLC (Agilent 1260 Infinity; Agilent Technologies, Santa Clara, USA) with a refractive index detector (RID G1362A; Agilent Technologies). Filtered samples with 50 µL in volume were injected and passed through an ion-exchange ligand-exchange column (Agilent Hi-Plex Ca column, 7.7×50 mm, 8 µm; Agilent Technologies) maintained at 75° C. with ultrapure water running at a flow rate of 0.6 mL/min as the mobile phase. The actual mass of powder deposited in various stages of the NGI was calculated based on the formulation compositions.

6.11 Animals

Female BALB/c mice with average age of 8 to 9 weeks and body weight of 18 to 22 g were used. The mice were housed under a 12 h dark-light cycle at a constant temperature and with ad libitum feeding on tap water and standard chow. All mice were obtained from the Laboratory Animal Unit (The University of Hong Kong). All experiments conducted were approved by the Committee on the Use of Live Animals for Teaching and Research (CULATR), The University of Hong Kong.

6.12 Intratracheal Administration

Before intratracheal administration, the mice were anaesthetized with intra-peritoneal injection of anaesthetics (80 mg/kg ketamine and 4.5 mg/kg xylazine in PBS) and a guiding cannula was intubated gently inside the trachea. The liquid or dry powder formulations were administered to the mice intratracheally through the guiding cannula. For liquid aerosol administration, the sample was loaded into a high-pressure syringe (Model FMJ-250; PennCenturyInc., Wyndmoor, PA, USA) and the liquid aerosol was generated by the Microsprayer® Aerosolizers (model IA-1C; Penn Century Inc., Wyndmoor, PA, USA). For powder formulations, the samples were loaded into a 200 µL gel-loading pipette tip which was connected to a 1 mL syringe by a three-way stopcock as previously described [22], and the powder was dispersed with 0.6 mL of air from the syringe.

6.13 mRNA Transfection In Vivo

In vivo mRNA transfection of $PEG_{12}KL4$/mRNA complexes was carried out with liquid or powder aerosol in BALB/c mice. For liquid formulations, $PEG_{12}KL4$/mRNA complexes prepared at 10:1 ratio (w/w) contained 5 or 10 µg mRNA in a final volume 75 µL of PBS were administered as a single dose. Naked mRNA or lipoplexes (Lipofectamine 2000/mRNA complexes at 2:1 ratio v/w), both containing 10 µg mRNA, were used as controls for comparison. For powder formulations, approximately 1 mg of SD-0.5% powder or SFD-0.5% powder (both containing 5 µg mRNA) were administered as a single dose. At 24 h post-administration, luciferin solution was administered intraperitoneally to the mice at a dose of 150 mg/kg body weight under lethal dose of phenobarbital. The lungs were harvested 10 min after luciferin injection, and bioluminescence imaging of the lungs was performed with an IVIS Spectrum in vivo imaging system (PerkinElmer, USA). The lung tissues were then homogenized and lysed in reporter cell lysis buffer. The samples were centrifuged at 1,500 g and 4° C. for 10 min. The luciferase expression in the supernatant was detected using the luciferase assay system as mentioned above. The results were expressed as RLU per mg of total protein.

6.14 Immunogenicity Assay and Histological Study

For immunogenicity study, the mice were intratracheally administered with PBS as control, LPS (10 µg), naked mRNA (5 or 10 µg) and $PEG_{12}KL4$/mRNA complexes at ratio 10:1 (w/w) (5 or 10 µg mRNA). All the samples were prepared in 75 µL of PBS and dispersed by Microsprayer® Aerosolizers except LPS which was prepared in 25 µL of PBS and delivered by micropipette. At 24 h post-administration, the mice were injected intraperitoneally with a lethal dose of pentobarbital. The bronchoalveolar lavage fluid (BALF) and the lung tissues were collected. The expressions of TNF-α, MCP-1, KC and IL-6 in BALF and lung homogenates were measured by ELISA. For histological study, the mice were intratracheally administered with PBS, LPS (10 µg), naked mRNA (5 µg), $PEG_{12}KL4$/mRNA complexes at ratio 10:1 (w/w) (5 µg mRNA), SD-0.5% mRNA powder (1 mg) and SFD-0.5% mRNA powder (1 mg). Naïve mice without any treatment were also included for comparison. At 24 h post-administration, the mice were injected intraperitoneally with a lethal dose of pentobarbital. The lungs were collected and gently inflated with 4% buffered formalin before fixation in formalin for 24 h. The left lobe of the lung was transferred to 80% of ethanol until they were embedded in a paraffin block. Sections of embedded tissue were mounted on slides and stained with hematoxylin and eosin (H&E). Slides were viewed with an upright microscope (Olympus BX50, Tokyo, Japan) using a UPlanFI 20x/0.5 objective. The images were taken by a digital camera (Sony NEX-6, Tokyo, Japan).

6.15 Statistical Analysis

A statistical test was carried out using Prism software version 6 (GraphPad Software Inc., San Diego, CA, USA) and analyzed by one-way analysis of variance (ANOVA) followed by Tukey's or Dunnett's post-hoc test unless specified. Differences were considered as statistically significant at p<0.05.

6.16 Background on Pulmonary siRNA Delivery

RNA interference (RNAi) is an endogenous post-transcription gene regulatory mechanism. It involves the interaction between small interfering RNA (siRNA) and the target messenger RNA (mRNA) through complementary binding, leading to the inhibition of specific gene expression. SiRNA has therapeutic potential in treating respiratory diseases such as asthma, chronic obstructive pulmonary disease (COPD), lung infections and cancer. The development of siRNA formulation suitable for pulmonary delivery is a key to its clinical translation. While KL4 peptide has previously demonstrated to mediate siRNA transfection on human lung epithelial cells, its clinical application is limited by its poor water solubility and the trigger of immunogenic responses. Through PEGylation of KL4 peptide, the solubility of the peptides is improved. The siRNA transfection (in vitro) mediated by PEG-KL4 is better than that of KL4. Furthermore, the immunogenicity and toxicity (in vivo) of the PEG-KL4/siRNA complexes are lower/negligible following intratracheal administration in mice, suggesting the PEG-KL4 is a promising candidate for pulmonary siRNA delivery in clinical applications.

6.17 Materials

PEG$_6$KL4, PEG$_{12}$KL4 and PEG$_{24}$KL4 peptides were purchased from EZBiolab (Carmel, NJ, USA) with purity>90%. The PEGylated KL4 stock solutions were prepared at 2 mg/mL in distilled water. Silencer Select GAPDH positive control and Silencer Select negative control siRNA were purchased from ThermoFisher Scientific (Waltham, MA, USA). SiRNA stock solutions were prepared at 1 mg/mL in ultrapure water.

6.18 SiRNA Transfection In Vitro

A549 cells were seeded in 6-well plates at a density of $1.5 \times 10^5$ cells per well one day before transfection. The cells were transfected with peptide/siRNA complexes containing 50 pmol of GAPDH siRNA or negative control siRNA per well (50 nM). The complexes were prepared in OptiMEM I reduced serum medium at 10:1, 15:1 and 20:1 ratios (w/w). Lipofectamine 2000 was used as control. The complexes were added to the cells and incubated for 4 h at 5% CO$_2$, 37° C. before being washed with PBS. The transfection medium was removed and replaced with serum supplemented cell culture medium. At 72 h post-transfection, the cells were washed and lysed with cell lysis buffer. Western blotting assay was performed to analyze the level of GAPDH protein. The GAPDH expression was analyzed by densitometry of Western Blots using Image J software. The remaining GAPDH expression was the density of the GAPDH band of positive control (normalized with beta-actin of the corresponding sample) divided by the GAPDH band of negative control (normalized with the beta actin band of the corresponding sample).

6.19 Immunogenicity Assay and Toxicity of siRNA Complexes In Vivo

Female BALB/c mice with average age of 8 to 9 weeks and body weight of 18 to 22 g were used. The mice were intratracheally administered with PBS as control, LPS (10 μg), PEG$_{12}$KL4/siRNA complexes (10:1 w/w) and KL4/siRNA complexes (10:1 w/w). Negative control siRNA was used. All samples were prepared in 75 μL of PBS and dispersed by Microsprayer® Aerosolizers except LPS which was prepared in 25 μL of PBS and delivered by micropipettes. At 24 h post-administration, the bronchoalveolar lavage fluid (BALF) and lung tissues were collected. The expression of TNF-α, MCP-1, KC and IL-6 in BALF and lung homogenates were measured by ELISA. The body weight of the mice was monitored before and at 24 h after administration.

7 RESULTS

7.1 Physicochemical Properties of Peptide/mRNA Complexes

The mRNA binding of peptides was evaluated by gel retardation assay (FIGS. 1A-1B). The mRNA band intensity decreased as the peptide to mRNA ratio (w/w) increased. For PEG$_{12}$KL4, complete binding was observed at 2.5:1 ratio at which the mRNA band was no longer visible. Compared to KL4 peptide, in which complete binding was achieved at a slightly lower ratio of 2:1, PEGylation did not have a major impact on mRNA binding. The binding affinity was further studied by using SDS to dissociate the complexes and displace the mRNA through competitive binding. The PEG$_{12}$KL4/mRNA complexes were dissociated by 2 mM of SDS, whereas the dissociation of the KL4/mRNA complexes required higher concentration of SDS at 4 mM, indicating a stronger association between mRNA and KL4. The particle size and zeta potential of the KL4/mRNA and PEG$_{12}$KL4/mRNA complexes prepared at 10:1 ratio (w/w) were measured (because of the effective in vitro transfection of PEG$_{12}$KL4/mRNA at this ratio) (Table 2). The hydrodynamic diameter of the freshly prepared PEG$_{12}$KL4/mRNA complexes was around 468 nm which was similar to the complexes in SD-0.5% mRNA powder formulations after reconstitution, which was around 432 nm. The particle size of the reconstituted SFD-0.5% mRNA powder formulation was around 375 nm, which was significantly smaller than the freshly prepared complexes. In addition, the freshly prepared PEG$_{12}$KL4/mRNA complexes were significantly larger than the KL4/mRNA complexes. The polydispersity indexes (PDI) of all the samples were similar, from 0.24 to 0.30. The zeta potential of KL4/mRNA and PEG$_{12}$KL4/mRNA complexes were around +26 mV and +27 mV, respectively, which were highly similar to each other. After reconstitution of SD-0.5% mRNA and SFD-0.5% mRNA powder formulations, the zeta potentials of the complexes were found to be +28 mV and +31 mV, respectively, which were also similar to the freshly prepared complexes albeit a small increase. The results showed that the physicochemical properties of the PEG$_{12}$KL4/mRNA complexes were not significantly affected by the two drying methods.

TABLE 2

Particle size and zeta potential of KL4/mRNA and PEG$_{12}$KL4/mRNA complexes. The complexes were prepared at 10:1 ratio (w/w). Spray dried (SD) and spray freeze dried (SFD) samples were reconstituted prior to measurement. The data was analysed by one-way ANOVA followed by Dunnett's post-hoc test as compared with the freshly prepared complexes.

|  | Hydrodynamic diameter (nm) | Poly-dispersity index | Zeta potential (mV) |
|---|---|---|---|
| KL4/mRNA complexes | 131.18 ± 20.96**** | 0.24 ± 0.05 | +25.81 ± 2.26 |
| PEG$_{12}$KL4/mRNA complexes | 467.93 ± 24.93 | 0.24 ± 0.02 | +26.50 ± 2.69 |
| Reconstituted SD-0.5% mRNA | 432.03 ± 13.62 | 0.27 ± 0.01 | +27.58 ± 0.83 |
| Reconstituted SFD-0.5% mRNA | 375.03 ± 9.90*** | 0.30 ± 0.01 | +30.58 ± 2.07 |

*p < 0.001, **p < 0.0001.
The data was prepared as mean ± standard deviation (n = 3).

7.2 In Vivo mRNA Transfection, Cellular Uptake and Immunogenicity Study

The mRNA transfection efficiency of the PEG$_{12}$KL4 peptide was studied on two human lung epithelial cell lines, A549 and BEAS-2B cells (FIGS. 2A-2B). The result was compared with KL4 peptide and the commercial transfection agent Lipofectamine 2000. A similar trend was observed on both cell lines. For PEG$_{12}$KL4 peptide, the transfection efficiency was improved when the peptide to mRNA ratio increased from 5:1 to 10:1, but no further improvement was noticed when the ratio continued to increase. There were no statistically significant differences among different ratios. In general, $PEG_{12}KL4$ peptide performed significantly better than KL4 peptide at their respective ratios, with a 1 to 2 log increase in luciferase expression observed, suggesting that PEGylation indeed improved mRNA transfection efficiency of KL4 peptide. In addition, the mRNA transfection efficiency of $PEG_{12}KL4$ peptide was comparable to that of Lipofectamine 2000. To further compare the cellular uptake efficiency of KL4/mRNA and $PEG_{12}$ KL4/mRNA complexes, confocal imaging and flow cytometry studies were carried out on A549 cells (FIGS. 3A-3D). Over 60% of the cells showed uptake of mRNA mediated by $PEG_{12}KL4$, whereas only 15% of cells showed mRNA uptake by KL4. Both the percentage of cell uptake and the median fluorescence intensity of the $PEG_{12}KL4$/mRNA were significantly higher than that of naked mRNA and KL4/mRNA complexes. The confocal images showed that the naked mRNA could not enter the cells as expected. Both the $PEG_{12}KL4$/mRNA and KL4/mRNA complexes were taken up by the cells as demonstrated by the intracellular red fluorescent signals. The green fluorescence was only present in the $PEG_{12}KL4$/mRNA transfected cells but not the KL4/mRNA transfected cells, suggesting that $PEG_{12}KL4$ was more efficient in mediating the cellular uptake and transfection of mRNA. The in vitro immunogenicity of the $PEG_{12}KL4$ peptide was examined on A549 and THP-1 cells (FIGS. 4A-4B). The levels of cytokines including MCP-1, TNF-$\alpha$ and IL-6 released from the transfected cells were similar to that of the negative control (no significant difference) and were significantly lower than that of the LPS treated samples, suggesting that $PEG_{12}KL4$ peptide/mRNA complexes did not induce an immunogenic response in vitro.

7.3 Morphology, Aerosol Performance and In Vitro mRNA Transfection of Powder Formulations The morphology of the $PEG_{12}KL4$/mRNA dry powder formulations was examined with SEM (FIG. 5). All the SD formulations appeared to be spherical in shape, and the geometric size of particles was well below 5 μm. There was no striking difference in appearance between the SD-0.1% mRNA and the SD-0.5% mRNA formulations, although the surface of both mRNA containing particles appeared to be rougher than the mannitol only (SD-mannitol) formulation. The particles prepared by SFD were much larger in size of over 10 m in diameter. These particles were highly porous with small amount of debris noticed in the SEM images. The particles containing mannitol only (SFD-mannitol) were highly aggregating and clumped together. On the other hand, the particles of the SFD-0.5% mRNA formulation appeared to be more discrete and spherical. The presence of peptide/mRNA complexes appeared to increase the physical robustness of the SFD particles. The aerosol performance of the dry powder formulations was evaluated by the NGI and was expressed in terms of EF and FPF (FIGS. 6A-6B). The EF which indicates the amount of powder successfully exited the inhaler was satisfactory for all the formulations, with a value of at least 75% or above. The FPF represents the respiration fraction of the powder. For the SD formulations, the presence of peptide/mRNA complexes lower the aerosol performance of the powder, with a significant reduction of FPF compared to the SD-mannitol formulation. The FPF of the SD-mannitol formulation was 60%, and the value decreased to 36% and 41% for the SD-0.1% mRNA and SD-0.5% mRNA formulations, respectively. An opposite trend was observed with the SFD preparations. The FPF of SFD-mannitol was 44%, and the value increased significantly to 62% and 68% for the SFD-0.1% mRNA and SFD-0.5% mRNA formulations, respectively. Overall, the SFD formulations of peptide/mRNA complexes performed significantly better, in terms of FPF, than their SD counterparts. The mass median aerodynamic diameter (MMAD) and the geometric standard deviation (GSD) were calculated based on the NGI data (Table 3). The MMAD of all the formulations were less than 6 μm with GSD less than 5 μm. For both drying methods, the 0.5% mRNA formulation exhibited a smaller MMAD and higher FPF compared to the 0.1% mRNA formulation prepared by the same method, suggesting that formulation containing a higher amount of $PEG_{12}KL4$/mRNA complexes exhibited better aerosol characteristics for inhalation.

TABLE 3

The mass median aerodynamic diameter (MMAD) and geometric standard deviation (GSD) of the spray dried (SD) and spray freeze dried (SFD) powder formulations. The values were calculated based on the Next Generation Impactor (NGI) data. The data was presented as mean ± standard deviation (n = 3).

| Formulation | MMAD (μm) | GSD (μm) |
|---|---|---|
| SD-Mannitol | 2.43 ± 0.68 | 4.10 ± 0.94 |
| SD-0.1% mRNA | 5.54 ± 0.81 | 4.71 ± 0.50 |
| SD-0.5% mRNA | 4.45 ± 0.36 | 4.61 ± 0.40 |
| SFD-Mannitol | 3.48 ± 0.34 | 2.79 ± 0.08 |
| SFD-0.1% mRNA | 2.13 ± 0.08 | 2.38 ± 0.02 |
| SFD-0.5% mRNA | 1.53 ± 0.15 | 3.17 ± 0.20 |

To examine the integrity of the mRNA after drying, in vitro transfection was carried out with the SD and SFD formulations on A549 cells (FIGS. 7A-7B). The transfection efficiency of all the dry powder formulations was successfully demonstrated. There was no significant difference between the freshly prepared complexes, and the samples before and after SD, indicating that the mRNA remained intact and the SD procedures did not compromise their biological activity. On the other hand, the transfection efficiency of SFD-0.5% mRNA formulation after drying was significantly lower than that before drying when 0.5 μg of mRNA was used per well, suggesting that there could be some minor degradation of mRNA during the SFD process. However, no significant difference was observed before and after drying with SFD-0.1% mRNA formulations, nor when 1 μg of mRNA per well was used in transfection.

7.4 In Vivo mRNA Transfection

Initially, the in vivo mRNA transfection efficiency of $PEG_{12}KL4$/mRNA complexes was evaluated with different peptide to mRNA ratios (2.5:1, 5:1 and 10:1 w/w) and at different time-points (4 and 24 h) following intratracheal administration as liquid aerosol in mice. The highest luciferase expression was observed with the complexes formed at 10:1 ratio (FIGS. 16A-16B), which was also consistent with the in vitro transfection study. Hence, the 10:1 ratio was adopted in the subsequent in vivo studies as well as the preparation of dry powder formulations. The luciferase expression in the lung was found to be higher at 24 h post-administration (FIGS. 17A-17B), which was used in the subsequent in vivo studies. Luciferase expression was shown in the lungs of mice treated with naked mRNA (FIGS. 8A-8B), but the luminescence was restricted to the trachea region only. On the other hand, the luciferase expression was observed in the lobes of the lungs in mice treated with $PEG_{12}KL4$/mRNA complexes, and the luciferase expression in the lung tissues was much higher than the naked mRNA group. Although the group treated with lipoplexes also demonstrated luciferase expression, similar to the naked mRNA group, the expression was limited to the trachea only, and the level of expression was even lower than that of the naked mRNA group. A biodistribution study was carried out at 4 h post-administration using cyanine-5 labelled mRNA to locate the site of aerosol deposition in the lung following intratracheal administration (FIG. 18). In all three treatment groups, fluorescent signal could be observed in the lobes of the lungs, showing that the aerosol could indeed reach the deep lung area, but only the PEG$_{12}$KL4/mRNA complexes could be successfully transfected to express luciferase in the deep lung, as shown in the bioluminescence images. In addition, it was found that the expression of luciferase mRNA was highly localized in the lung following intratracheal administration of PEG$_{12}$KL4/mRNA complexes, either as liquid aerosol or powder aerosol, but not in other organs at 24 h post-administration (FIG. 19).

The transfection efficiency of the PEG$_{12}$KL4/mRNA complexes at different concentrations in the liquid aerosol was further investigated in vivo (FIGS. 9A-9C). The complexes containing either 5 or 10 μg mRNA (i.e. 50 or 100 μg PEG$_{12}$KL4) were delivered to the mice intratracheally. The luciferase expression in the lung was observed in both treatment groups, with the 5 μg mRNA treatment group displayed a significantly higher luciferase expression. Moreover, the lower dose did not cause any significant change in body weight at 24 h post-administration while the higher dose resulted in about 6% of body weight loss. Therefore, it is concluded here that the 5 μg of mRNA dose could achieve high transfection efficiency and low in vivo toxicity at the same time. Lastly, the SD-0.5% mRNA and SFD-0.5% mRNA formulations were delivered to the mice as reconstituted liquid aerosol or as powder aerosol (FIGS. 10A-10B). Both liquid and powder aerosol could express luciferase at 24 h post-administration, but the former displayed significantly higher transfection efficiency. The SD formulation also performed better than the SFD formulation, indicating that the SD process could preserve the integrity and hence the biological activity of the mRNA better than the SFD process, which was consistent with the in vitro transfection results.

7.5 Safety Profile

The immunogenicity of PEG$_{12}$KL4/mRNA complexes was investigated on mice by measuring the level of pro-inflammatory cytokines in BALF and lung homogenates (FIGS. 11A-11B). The expression of MCP-1, TNF-alpha, KC, and IL-6 was significantly induced by LPS in both BALF and lung homogenates but not affected by naked mRNA and PEG$_{12}$KL4/mRNA, at both 5 and 10 μg mRNA dose, except that the PEG$_{12}$KL4/mRNA at 10 μg mRNA dose significantly induced the MCP-1 expression in BALF. The body weight of mice was also monitored. Only the LPS treatment group caused significant weight loss at 24 h post-administration compared with the mice treated with the control group (FIG. 20). The naked mRNA and PEG$_{12}$KL4/mRNA complexes when administered at 10 μg mRNA dose also caused some weight loss, but the changes were not statistically significant compared to the control group. The histological characteristics of the lungs treated with liquid and powder aerosol of PEG$_{12}$KL4/mRNA complexes (5 μg mRNA) were compared with the untreated control, PBS treated and LPS treated groups (FIGS. 12A-12G). The lungs without any treatment or treated with PBS illustrated a healthy presentation while the lung treated with 10 μg of LPS intratracheally showed irregular distribution of air space and inflammatory cell infiltration into the interstitial and alveolar spaces. The lungs treated with PEG$_{12}$KL4/mRNA complexes, either as liquid or powder aerosol, did not show signs of inflammation. Overall, a single dose of PEG$_{12}$KL4/mRNA at 5 μg mRNA dose per mouse did not show any signs of inflammation and toxicity in the lungs.

8 DISCUSSION

One of the most important barriers to overcome for clinical translation of nucleic acid based therapeutics is delivery [23]. This issue must be addressed before effective in vivo nucleic acid therapy is truly realized. As a mimic of SP-B, the synthetic KL4 was initially employed to dissect the role of surfactants on nucleic acid delivery. The delivery of mRNA is investigated here because (i) the single-stranded mRNA is a challenging molecule to deliver due to its unstable nature; (ii) there is a lack of studies that explore the inhaled dry powder formulation of mRNA (more studies on siRNA) [27, 28]; (iii) mRNA has huge therapeutic potential for treatment of many lung diseases as well as prevention of diseases in form of mRNA vaccines [29, 30]; and (iv) it is relatively easy to quantify the expression of mRNA with reporter gene without establishing a disease model.

The leucine-rich KL4 peptide has a poor aqueous solubility, limiting its application as non-viral vector. As demonstrated in the cellular uptake and transfection studies, PEG$_{12}$KL4 was more efficient than KL4 in delivering mRNA to the cells. The presence of PEG could improve mRNA transfection by promoting cellular entry as well as the release of mRNA in the cells more effectively for protein translation to occur.

Two particle engineering techniques, SD and SFD, were employed to produce inhaled dry powder formulation of mRNA. It is crucial that the integrity of peptide/mRNA complexes can be preserved after drying while the powders exhibit good aerodynamic properties for efficient lung deposition. SD is a single step operation that converts feed liquid into dried particles by atomizing the liquid into fine droplets which are immediately brought into contact with a stream of hot drying gas inside a drying chamber. During the process, molecules are exposed to elevated temperature and shear stress, increasing the risk of RNA degradation [35]. However, this drying method is easily scale-up in industry for mass production. SFD is a multi-step process that involves the atomization of a liquid into cryogen (typically liquid nitrogen) in which the particles are instantaneously frozen, followed by the sublimation of the solvent during freeze-drying. The SFD is more suitable for thermo-labile biological molecules and the formation of porous particles usually exhibit good aerosol properties, but the production time is longer and scale-up is more complicated. According to the physicochemical characterization, the PEG$_{12}$KL4/mRNA complexes behaved similarly before and after drying in terms of particle size and zeta potential, showing that the drying conditions employed did not have a major impact on the properties of PEG$_{12}$KL4/mRNA complexes. In the transfection study, both in vitro and in vivo, the transfection efficiency of the SD formulation was better than the SFD formulation, suggesting that integrity of mRNA could be partially compromised during the SFD process. One interesting observation was that the zeta potential of the reconstituted SFD formulation was slightly higher than the freshly prepared complexes as well as the reconstituted SD formulation, which suggested that some negatively charged mRNA might be degraded during the SFD process, altering the PEG$_{12}$KL4 peptide to mRNA ratio such that the complexes became more positive. The damage of mRNA could be caused by the sudden exposure of extreme low temperature at the spray freeze step or physical impacts during the freeze drying process such as the driving force during the sublimation or phase separation [36]. Nevertheless, there was a considerable amount of intact mRNA remained in the SFD formulation to allow successful transfection to take place.

Both SD and SFD powder formulations exhibited desirable aerosol properties for inhalation. Although the particles of SFD formulations were physically larger, their aerosol performances were indeed better than the SD formulations, reflected by the higher FPF value. This could be attributed to the porous nature of the SFD powder. It is known that SFD can produce porous particles with low density through the sublimation of solvent during the freeze-drying step [37]. The aerodynamic diameter is proportional to the physical size and the density. By making the particles porous, the aerodynamic diameter could be reduced, as demonstrated by the MMAD of 4.5 μm in the SD-0.5% mRNA formulation and 1.5 μm in the corresponding SFD formulations. Compared to the mannitol only powder, the inclusion of $PEG_{12}KL4$/mRNA complexes in the SD formulations had a negative impact on the aerosol performance, resulting in a lower FPF. However, when the amount of mRNA was increased from 0.1% to 0.5%, there was no significant difference in FPF between the two. In contrast, the presence of $PEG_{12}KL4$/mRNA complexes improved the aerosol performance of the SFD formulation.

The in vivo study demonstrated that the $PEG_{12}KL4$ peptide was safe for pulmonary delivery, with low immunogenicity and toxicity at mRNA dose that showed effective transfection efficiency in the lung (5 μg per mouse), although repeated dose is required to demonstrate its long-term safety. Transfection of naked mRNA and lipoplexes were also observed following intratracheal administration, but the luciferase expression was limited to the trachea and they failed to transfect in the deeper region of the lungs. On the contrary, the $PEG_{12}KL4$ could mediate effective mRNA expression in the deep lung area. Naked mRNA and lipoplexes are incapable of penetrating the mucus and pulmonary surfactant barriers to reach the epithelial cells in the deeper lung region, resulting in poor transfection [39]. While mRNA transfection in the lung has been shown by others using different types of polymers [15], none of them reported dry powder formulation for inhalation.

On a closer examination of the in vivo transfection study of $PEG_{12}KL4$/mRNA complexes, the liquid aerosol produced better mRNA expression in the lung as compared to the powder aerosol despite the same mRNA dose was delivered. This could be attributed to the suboptimal powder insufflation during the intratracheal administration which is a challenging procedure [40], resulting in incomplete powder dispersion in the lung of animals. In fact, the cascade impactor study is a more appropriate and relevant method to evaluate powder dispersibility and aerosol performance of the powder formulation. Most importantly, the reconstituted powders were able to mediate good mRNA transfection in the lung of animals. When comparing between SD and SFD method, the former consistently showed better transfection efficiency, possibly due to the better preservation of mRNA integrity during the SD process, although SFD formulations displayed better aerosol performance due to their porous structure with low density. To further improve the mRNA dry powder formulation, the aerosol performance of SD powder could be optimized by reducing the size or density of the particles, or including a dispersion enhancer such as leucine in the formulation, whereas the incorporation of cryoprotectant such as trehalose could be used in the SFD formulation.

Provided herein is the first report of inhalable dry powder mRNA formulation for pulmonary delivery. The modification of the KL4 peptide by PEGylation resulted in the enhancement of solubility as well as transfection efficiency. Dry powder formulations of $PEG_{12}KL4$/mRNA prepared by SD and SFD techniques were suitable for inhalation, with the SD method being superior in preserving mRNA integrity. Effective transfection in the lung was observed when $PEG_{12}KL4$/mRNA complexes were administered intratracheally in mice as either liquid or powder aerosol, with low risk of immunogenicity and toxicity. Provided herein is $PEG_{12}KL4$, a non-viral vector for mRNA pulmonary delivery, in dry powder form, for therapeutic as well as vaccine applications.

9. INSIGHTS INTO THE EFFECT OF PEGYLATION ON SIRNA TRANSFECTION MEDIATED BY KL4 PEPTIDE

9.1 Introduction

Pulmonary delivery of small interfering RNA (siRNA) is a promising therapeutic strategy for treating various respiratory diseases. A carrier is required for effective delivery of siRNA to the cells in the lung. Our previous study demonstrated that the cationic KL4 peptide is effective in mediating robust siRNA transfection in lung epithelial cells. However, its low water solubility due to the high hydrophobic leucine content has limited its application as delivery vector. To address this problem, PEGylation strategy was investigated here to improve the solubility of KL4 peptide. Monodisperse polyethylene glycol (PEG) with length varied between 6 to 24 monomers was covalently attached to the KL4 peptide. All the PEGylated KL4 peptides could bind and form nano-sized complexes with siRNA, but the interaction between siRNA and peptides became weaker as the PEG chain length increased. The transfection efficiency was investigated on three human lung epithelial cell lines, including A549 cells, Calu-3 cells and BEAS-2B cells. All the PEGylation KL4 peptides exhibited satisfactory transfection efficiency on all cell lines. Among all the peptides, $PEG_{12}KL4$ peptide, which contains 12 monomers of PEG, was identified to be optimal for siRNA delivery because of its good water solubility, robust transfection efficiency and high cellular uptake in lung epithelial cells. It also demonstrated low risk of inflammatory response and toxicity in vivo following pulmonary administration.

RNA interference (RNAi) is a powerful gene-silencing process that has great potential for the treatment of many diseases [41]. Since its discovery decades ago, the application of RNAi molecules such as short hairpin RNA (shRNA), small interfering RNA (siRNA) and microRNA (miRNA) have been limited to research tools. This situation has changed when the first ever RNAi drug (Patisiran), an siRNA against hereditary transthyretin amyloidosis, was approved by the FDA in 2018 [42, 43]. Soon after this approval, another siRNA-based drug (Givosiran) for adults with acute hepatic porphyria also obtained FDA approval in 2019 [44, 45]. With this success of translation from bench to bedside, it is expected that more siRNA therapeutics will be in the market in the coming years.

Pulmonary delivery of siRNA holds great promise for the treatment of respiratory diseases such as lung cancers, inflammatory lung diseases, respiratory infections and pulmonary fibrosis [46-49]. Effective delivery vectors are necessary to promote the cellular uptake of siRNA. Inspired by the surfactant protein B (SP-B) in the pulmonary surfactant, which was reported to enhance siRNA delivery of proteolipid coated nanogel formulation [50], our group developed a non-viral vector using the SP-B mimic KL4 peptide [17]. KL4 is a cationic synthetic peptide with 21 amino acids containing repeating KLLLL (SEQ ID NO: 2) sequences. It mediated efficient siRNA transfection in vitro without significant signs of cytotoxicity. However, the high leucine content of KL4 peptide renders it poorly soluble in water.

To overcome the solubility problem, one popular strategy is PEGylation. Studies have shown that the attachment of the hydrophilic polyethylene glycol (PEG) to proteins and peptides could effectively improve solubility, physical stability, circulation time and decrease immunogenic response [51-54]. PEGylation has been widely investigated for siRNA delivery with polymers, lipids and peptides [55, 56]. The PEGylation rate and the PEG chain length could affect size distribution, stability, cellular uptake and transfection efficiency of the delivery system. However, there are conflicting results of how PEGylation affected siRNA delivery. Some studies showed that the increase of PEGylation rate had negative effects on siRNA transfection efficiency because of the reduced cellular uptake or endosomal escape of siRNA [57, 58]. Others showed that when a targeting ligand was included in a delivery system, the incorporation of PEG as a spacer increased siRNA transfection efficiency by promoting the binding between ligand and receptor, or PEGylation simply facilitated the release of siRNA from the vector, thereby enhancing transfection efficiency [59, 60]. Besides, most of these studies used polydisperse PEG polymers which are subjected to batch to batch variation. Compared with polydisperse PEG, monodisperse PEG with a precise and discrete molecular weight is preferred because of its homogeneity and high reproducibility, making it easier for chemical characterization and purity control [61]. However, limited studies used monodisperse PEG in siRNA delivery [62-65], possibly due to the relatively high cost of production. PEG polymer can be directly conjugated to siRNA or study are to understand the impact of PEGylation on siRNA transfection efficiency and identify the optimal candidate through the investigation of peptide conformation, siRNA binding affinity, physicochemical properties of the peptide/siRNA complexes, cellular uptake, toxicity and inflammatory response of the complexes.

9.2 Materials and Methods

Materials

KL4 peptide was purchased from ChinaPeptides (Shanghai, China) and PEGylated KL4 peptides with various PEG length were purchased from EZBiolab (Carmel, NJ, USA) with purity>90% (Table 4). KL4 and PEG$_6$KL4 stock solutions were prepared at 1 mg/mL in 1% (v/v) DMSO. PEG$_{12}$KL4 and PEG$_{24}$KL4 stock solutions were prepared at 2 mg/mL in distilled water. Fluorescently labelled siRNA (siGLO Cyclophilin B Control siRNA) was purchased from GE Dharmacon (Lafayette, CO, USA). Silencer Select GAPDH Positive Control siRNA, Silencer Select negative control siRNA, Dulbecco's modified Eagle's medium (DMEM), Keratinocyte-SFM, OptiMEM I reduced serum medium, trypsin-EDTA (0.25%), Fetal Bovine Serum (FBS), Antibiotic-Antimycotic (100×), Lipofectamine 2000 were purchased from ThermoFisher Scientific (Waltham, Massachusetts, USA). SiRNA stock solutions were prepared at 0.5-1 mg/mL in ultrapure DEPC-treated water. GelRed nucleic acid stain was purchased from Biotium (Hayward, CA, USA). Anti-GAPDH and anti-beta-actin antibodies were purchased from abcam (Cambridge, UK). Secondary antibody and Amersham ECL Western blotting detection reagents were purchased from GE Healthcare (Amersham, UK). Mouse tumor necrosis factor-alpha (TNF-α), monocyte chemoattractant protein-1 (MCP-1), keratinocyte-derived chemokine (KC) and interleukin-6 (IL-6) ELISA kits were purchased from R&D Systems (Minneapolis, MN, USA). Heparin sodium was purchased from Leo Pharmaceutical Ltd (Ballerup, Denmark). Lipopolysaccharide (LPS) from E. coli O111:B4 and other reagents were obtained from Sigma-Aldrich (Saint Louis, MO, USA) as analytical grade or better.

TABLE 4

Sequence, numbers of PEG monomers, molecular weight of peptides used in this study.

| Peptide | Sequence | Number of PEG monomer | Molecular weight (Da) | Solubility in water |
|---------|----------|-----------------------|-----------------------|---------------------|
| KL4 | KLLLLKLLLLKLLLLKLLLLK-NH$_2$ (SEQ ID NO: 1) | 0 | 2468.48 | <1 mg/mL |
| PEG$_6$KL4 | PEG$_6$-KLLLLKLLLLKLLLLKLLLLK-NH$_2$ (SEQ ID NO: 3) | 6 | 2804.06 | <1 mg/mL |
| PEG$_{12}$KL4 | PEG$_{12}$-KLLLLKLLLLKLLLLKLLLLK-NH$_2$ (SEQ ID NO: 4) | 12 | 3068.39 | >2 mg/mL |
| PEG$_{24}$KL4 | PEG$_{24}$-KLLLLKLLLLKLLLLKLLLLK-NH$_2$ (SEQ ID NO: 5) | 24 | 3595.41 | >2 mg/mL |

* K = Lysine; L = Leucine; PEG = polyethylene glycol it is used to modify the delivery vectors to improve biocompatibility. For instance, Wagner et al. used PEG$_{24}$ (PEG with 24 monomers) to shield the surface of the oligomers and minimize unspecific interactions in the blood for DNA and siRNA delivery [65].

In this study, three PEGylated KL4 peptides with chain length of monodisperse PEG varied between 6 to 24 monomers were investigated and compared. The aims of this Circular Dichroism (CD)

KL4 and PEG$_6$KL4 peptides were dissolved in 5 mM Tris-HCl buffer at a final concentration of 0.1 mg/mL in 0.1% (v/v) DMSO. PEG$_{12}$KL4 and PEG$_{24}$KL4 were dissolved in 5 mM Tris-HCl buffer at a final concentration of 0.1 mg/mL without DMSO. CD spectra were acquired on a Chirascan™ Spectrometer (Applied Photophysics, Leatherhead, UK). For temperature ramping experiment, far-UV CD spectra were obtained with the peptide solution incubated from 6° C. to 94° C. Spectra were recorded from 260 to 190 nm using a 0.5 mm path length and were processed using Chirascan software where a spectrum of the peptide free solution was subtracted and Savitzky-Gorlay smoothing applied.

Fluorescence Displacement Assay

The siRNA binding affinity of the peptides was investigated by fluorescence displacement assay using negative control siRNA. The siRNA was added into 1× SYBR® Gold Tris-acetate-EDTA (TAE) buffer and incubated for 30 min at room temperature. The fluorescence intensity was quantified by fluorescence spectrophotometer (SpectraMax® M4, Molecular devices, LLC., CA, USA) at 495 nm excitation and 537 nm emission wavelengths. The peptides at concentration of 1 mg/mL were titrated to the siRNA/dye mixtures. The fluorescence intensity of siRNA/dye mixture in the presence of peptides was expressed as a percentage of that of the siRNA/dye mixture without peptides. The background fluorescence was subtracted from all measurements before analysis. Percentage change of fluorescence intensity was plotted against the weight ratio of peptides to siRNA upon titration. To further investigate the binding profile of the peptide/siRNA complexes, heparin was added to dissociate the complexes and release the siRNA. The peptides were added to the siRNA/dye mixtures at peptide to siRNA ratio 10:1 (w/w) and incubated for 30 min. The heparin diluted in TAE buffer at concentration of 10 or 100 i.u./µL was titrated into the peptide/siRNA/dye mixture and the fluorescence intensity was measured as described above. Percentage change of fluorescence intensity was plotted against the amount of heparin upon titration. The data was fit to a four-parameter logistic sigmoidal curve and the $EC_{50}$ and Hill slope were calculated.

Particle Size and Zeta Potential Measurement

For particle size measurement, peptide/siRNA complexes were prepared at 10:1 ratio (w/w) with 4 µg of siRNA in 100 µL of ultrapure water. At 30 min after complexes formation, the hydrodynamic size was measured by dynamic light scattering (DLS) (Delsa™ Nano C, Beckman Coulter, CA, USA). To study the effects of salt on particle size of the peptide/siRNA complexes, phosphate-buffered saline (PBS) was added to the complexes and the particle size was measured after 30 min of incubation. For zeta potential measurement, the peptide/siRNA complexes were prepared at 10:1 (w/w) with 20 µg of siRNA in 500 µL of 2% PBS. At 30 min after complexes formation, the zeta potential was measured in a flow cell using electrophoretic light scattering (Delsa™ Nano C, Beckman Coulter, CA, USA).

Transmission Electron Microscopy

The peptide/siRNA complexes were prepared at 10:1 ratio (w/w) with 4 µg of siRNA in 200 µL of ultrapure water, and the samples were incubated for 30 min. The complexes were loaded on a discharged copper grid coated with carbon-Formvar and stained with 4% (w/v) uranyl acetate. The morphology of the peptide/siRNA complexes was visualized by the transmission electron microscope (TEM) (FEI Tecnai G² 20 S-TWIN, FEI company, Hillsboro, Oregon, USA) at a voltage of 100 kV. Micrographs were taken using a digital camera (Gatan ORIUS SC600 Model 831 CCD Camera 2.7k×2.7k pixel with Digtalmicrograph software).

Cell Culture

A549 cells (human alveolar epithelial adenocarcinoma), BEAS-2B cells (human bronchial epithelial cells), Calu-3 cells (human lung epithelial adenocarcinoma) were obtained from ATCC (Manassas, VA, USA). A549 cells were cultured in DMEM supplemented with 10% (v/v) FBS and 1% (v/v)

antibiotic-antimycotic. BEAS-2B cells were cultured in Keratinocyte-SFM supplemented with human recombinant Epidermal Growth Factor (rEGF), Bovine Pituitary Extract (BPE), and 1% (v/v) antibiotic-antimycotic. Calu-3 cells were cultured in DMEM/F12 supplemented with 10% (v/v) FBS and 1% (v/v) antibiotic-antimycotic. All the cells were maintained at 5% $CO_2$, 37° C., and subcultured according to ATCC instruction.

siRNA Transfection

A549 cells, BEAS-2B and Calu-3 cells were seeded in six-well plates at a density of $1.6 \times 10^5$ cells per well, $2 \times 10^5$ cells per well and $3 \times 10^5$ cells per well, respectively, one to two days before transfection. The cells were transfected with peptide/siRNA complexes at 5:1 to 20:1 ratio (w/w) containing GAPDH siRNA or negative control siRNA (6 to 100 nM) in OptiMEM I reduced serum medium. Lipofectamine 2000 was used for comparison. After 5 h of incubation, the cells were washed and replaced with serum supplemented cell culture medium. At 72 h post-transfection, the cells were washed and lysed with cell lysis buffer. Western blotting assay was performed to analyze the level of GAPDH protein as previously described [66]. The GAPDH expression was analyzed by densitometry of Western blots using ImageJ software (Version 1.52). The GAPDH expression was normalized with the expression of □-actin of the corresponding sample. The remaining GAPDH expression was the normalized GAPDH expression of positive control divided by the normalized GAPDH expression of negative control.

Flow Cytometry Study

Flow cytometry was used to investigate the cellular uptake of peptide/siRNA complexes. A549 cells and Calu-3 cells were seeded in six-well plates at a density of $2.5 \times 10^5$ cells and $4 \times 10^5$ cells per well, respectively, one day before the experiment. The cells were transfected with peptide/siRNA complexes at 10:1 ratio (w/w) containing fluorescently labelled siRNA (150 nM) in Opti-MEM I reduced serum medium. The transfection medium was removed after 4 h of incubation, and the cells were washed with PBS once. The cells were trypsinized by 0.25% (w/v) trypsin-EDTA and suspended in culture medium. The extracellular fluorescence signal was quenched with 0.04% (w/v) trypan blue solution. After 2 min of incubation, the cells were washed with PBS thrice. The cells were resuspended in 500 µL of PBS and sieved with a sterile 40 µm cell strainer (BD Biosciences, CA, USA). The fluorescence intensity was analyzed by flow cytometry with PE/PI laser (585/42 nm) (BD FACSCantoII Analyzer, BD Biosciences, CA, USA). At least 10,000 single cells were analyzed for each sample.

Animals

Female BALB/c mice with average age of 8 to 9 weeks and body weight of 18 to 22 g were used. The mice were housed under a 12 h dark-light cycle at a constant temperature and with ad libitum feeding on tap water and standard chow. All mice were obtained from the Laboratory Animal Unit (The University of Hong Kong). All experiments conducted were approved by the Committee on the Use of Live Animals for Teaching and Research (CULATR), The University of Hong Kong.

In Vivo Inflammatory Study

The mice were intratracheally administered with KL4/siRNA and $PEG_{12}KL4$/siRNA complexes at ratio 10:1 (w/w) containing 10 µg of siRNA. PBS and LPS (10 µg) were used as controls. Before intratracheal administration, the mice were anaesthetized with intra-peritoneal injection of anaesthetics (80 mg/kg ketamine and 4.5 mg/kg xylazine). All the samples were prepared in 75 µL of PBS and loaded into a high-pressure syringe (Model FMJ-250; Penn- Century Inc., Wyndmoor, PA, USA) and the liquid aerosol was generated by Microsprayer® Aerosolizers (model IA-1C; PennCentury Inc., Wyndmoor, PA, USA) except LPS which was prepared in 25 μL of PBS and delivered by micropipette. The body weight of the mice was monitored before and 24 h after administration. The mice were injected intraperitoneally with a lethal dose of pentobarbital. The bronchoalveolar lavage fluid (BALF) and the lung tissues were collected. The expressions of TNF-α, MCP-1, KC and IL-6 in BALF and lung homogenates were measured by ELISA.

Statistical Analysis

A statistical test was carried out using Prism software version 8 (GraphPad Software Inc., San Diego, CA) and analyzed by one-way analysis of variance (ANOVA). All experiments were repeated at least three times independently unless otherwise indicated. Differences were considered as statistically significant at $p<0.05$.

9.3 Results

Secondary Structure of Peptides

The secondary structures of the peptides in free solution were examined at different temperatures using CD (FIG. 21). At lower temperatures, KL4 peptide adopted an alpha-helical conformation as the typical strong positive band at 190-195 nm and two negative bands at 208-210 nm and 222 nm were observed in the CD spectrum. When the temperature increased to around 90° C., the alpha-helical structure gradually turned to a beta-sheet conformation, as indicated by the single negative band between 215-220 nm and the positive band at 195 nm. The structures of $PEG_6KL4$ and $PEG_{24}KL4$ were very similar, both of which adopted an alpha-helical structure at all tested temperatures, indicating high thermal stability albeit a small gradual reduction of intensity as the temperature went up. The conformation of $PEG_{12}KL4$ peptide was more sensitive in response to temperature compared with the other peptides. As temperature increased, it experienced conformational change from a mixture of alpha-helical and beta-sheet, to typical alpha-helix conformation, and finally to beta-sheet structure.

Fluorescence Displacement Assay

The binding affinity of the peptides to siRNA was studied by the fluorescence displacement assay (FIGS. 22A-22B). There was a sharp decrease of fluorescence intensity as the ratio of peptide to siRNA increased, indicating that the dye was displaced upon the binding between peptides and siRNA. The PEGylated KL4 peptides showed a steeper slope compared to the KL4 peptide up to ratio 10:1 (w/w), indicating that the PEGylated peptides were more effective than KL4 in displacing the dye from siRNA. At ratio 10:1 or above, the curves started to plateau out for all peptides, indicating that the binding between siRNA and peptides was almost complete. To further examine the interaction between siRNA and peptides, all complexes were formed at 10:1 ratio and heparin was added to displace the siRNA from the complexes, leading to the increase in fluorescence intensity. Interestingly, the shapes of the curves of KL4 and $PEG_6KL4$ peptides were different from those for $PEG_{12}KL4$ and $PEG_{24}KL4$ peptides. The data was fit to the four-parameter logistic (4PL) sigmoidal model for further illustration. The coefficient of determination ($R^2$) for all peptides was greater than 0.995, suggesting the model fits well with the data. The $EC_{50}$, which indicated the amount of heparin that caused 50% of increase in fluorescence intensity, and the Hill slope were analyzed with this model. The $EC_{50}$ decreased as the PEG chain length increased, indicating that it was easier for siRNA to release from the complexes upon heparin titration. The Hill slope was used to quantify the steepness of the curve, with steeper the curve, the higher the Hill slope value. As the PEG chain length increased, the Hill slope value increased, suggesting that siRNA was more readily released from peptides with longer PEG length. Both parameters show that the interaction between siRNA and peptides was weaker as the PEG chain length increased.

Physicochemical Properties of Peptide/siRNA Complexes

The hydrodynamic diameter of peptide/siRNA complexes was measured by DLS (Table 5). The mean diameter of the KL4/siRNA complexes was around 650 nm. The particle size of complexes formed with PEGylated KL4 peptides was significantly smaller, ranging from around 160 nm to 230 nm. The zeta potential of the KL4/siRNA complexes was around +33 mV, which was also significantly higher than that of the PEGylated KL4 peptide/siRNA complexes, which ranged from +13 to +19 mV. To examine the effect of electrolyte on the particle size of the complexes, PBS was added into the solution of complexes (FIG. 23). All the peptide/siRNA complexes showed a significant increase in particle size in the presence of PBS, and the effect was most prominent in KL4 in which the size of KL4/siRNA complexes rose to almost 6,000 nm. As the PEG chain length increased, the increase of particle size attenuated. For $PEG_{24}KL4$/siRNA complexes, the size only increased to around 350 nm, suggesting that the longer the PEG chain length, the more stable the particle size was. The morphology of peptide/siRNA complexes was visualized by TEM (FIGS. 24A-24B). The KL4/siRNA complexes appeared as large aggregates with free KL4 peptides observed (free KL4 peptide appeared as filiform structure, see FIG. 32). All the complexes formed by PEGylated KL4 peptides appeared to be smaller in size and more compact, which was consistent with the size measurement by the DLS.

TABLE 5

Particle size and zeta potential of peptide/siRNA complexes prepared at ratio 10:1 (w/w) in water and measured by dynamic light scattering and electrophoretic light scattering. The data was presented as mean ± standard deviation (n = 3).

| Peptide/siRNA | Hydrodynamic diameter (nm) | Polydispersity index | Zeta potential (mV) |
|---|---|---|---|
| KL4/siRNA | 650.65 ± 164.01 | 0.29 ± 0.05 | 32.98 ± 2.25 |
| $PEG_6KL4$/siRNA | 163.57 ± 25.45 | 0.26 ± 0.09 | 13.18 ± 3.93 |
| $PEG_{12}KL4$/siRNA | 274.05 ± 32.26 | 0.22 ± 0.02 | 19.54 ± 5.80 |
| $PEG_{24}KL4$/siRNA | 184.67 ± 1.33 | 0.29 ± 0.02 | 16.55 ± 4.45 |

In Vitro siRNA Transfection

The transfection efficiency of peptides was performed on two human lung cancer cell lines (A549 and Calu-3) and one human non-cancer lung cell line (BEAS-2B) (FIGS. 25A-25B, 26A-26B, 27A-27B). At 72 h post-transfection, the GAPDH protein was downregulated by the peptide/siRNA complexes on all three cell lines from ratio 5:1 to 20:1 (w/w). In general, the higher the ratio, the better the transfection efficiency. On A549 cells (FIGS. 25A-25B), over 80% knockdown of GAPDH protein was achieved in cells transfected with KL4/siRNA, $PEG_6KL4$/siRNA, $PEG_{12}KL4$/siRNA at ratio 10:1 (w/w) and above. There was no significant difference between different peptide/siRNA complexes formed at the same ratio (Table 6), or the complexes of the same peptide formed at different ratios (Table 7), except for $PEG_{24}KL4$/siRNA at ratio 5:1 (w/w), which performed significantly worse than ratio 15:1 and 20:1. The transfection efficacy of these peptides was comparable with the commercial transfection reagent lipofectamine 2000. For Calu-3 cells (FIGS. 26A-26B), over 70% of GAPDH protein expression was inhibited for all peptide/siRNA complexes at ratio 10:1 (w/w) or above. At 10:1 ratio (w/w), the highest knockdown can be observed in the $PEG_{12}KL4$/siRNA complexes, with more than 90% of GAPDH protein suppression achieved. Notably, Lipofectamine 2000 was inefficient in mediating siRNA transfection on this cell line, and all four peptides had significantly higher transfection efficiency compared with lipofectamine 2000. For BEAS-2B cells (FIGS. 27A-27B), the transfection efficiency also increased as the ratio increased for these peptides. Both $PEG_6KL4$ and $PEG_{12}KL4$ peptides had significantly higher transfection efficiency compared with lipofectamine 2000. The transfection efficiency of different peptides was further compared on A549 cells by employing different amount of siRNA while keeping the peptide to siRNA ratio at 10:1 (w/w) (FIGS. 28A-28B). The transfection efficiency of all the peptides was in a concentration-dependent manner. Among these four peptides, $PEG_6KL4$ and $PEG_{12}KL4$ were most effective in transfecting siRNA. These two peptides could inhibit GAPDH protein by 80% at 25 nM siRNA concentration, while the other two peptides required 50 nM siRNA to achieve a similar level of inhibition.

TABLE 6

Comparison between different peptides prepared the same peptide to siRNA ratios.

| Cell lines | 5:1 | 10:1 | 15:1 | 24:1 |
|---|---|---|---|---|
| A549 | n.s. | n.s. | n.s. | n.s. |
| Calu-3 | n.s. | n.s. | $PEG_{24}KL4$ vs $PEG_{24}KL4$* | n.s. |
| BEAS-2B | n.s. | n.s. | n.s. | n.s. |

TABLE 7

Comparison within the same peptide prepared at different peptide to siRNA ratios.

| Cell lines | KL4 | $PEG_6KL4$ | $PEG_{12}KL4$ | $PEG_{24}KL4$ |
|---|---|---|---|---|
| A549 | n.s. | n.s. | n.s. | 5:1 vs 15:1 *<br>5:1 vs 20:1 * |
| Calu-3 | 5:1 vs 10:1 *<br>5:1 vs 15:1 *<br>5:1 vs 20:1 ***<br>10:1 vs 20:1 * | n.s. | 5:1 vs 15:1 *<br>5:1 vs 20:1 * | n.s. |
| BEAS-2B | 5:1 vs 10:1 *<br>5:1 vs 15:1 *<br>5:1 vs 20:1 ** | n.s. | n.s. | 5:1 vs 20:1 * |

The data were analyzed by one-way ANOVA followed by Tukey's post hoc test, n.s. not significant, * $p < 0.05$,  $p < 0.01$, * $p < 0.001$.

Cellular Uptake

The cellular uptake of siRNA mediated by the four peptides was assessed by flow cytometry quantitatively on A549 cells and Calu-3 cells (FIGS. 29A-29D). As expected, naked siRNA could not enter the cells. For A549 cells, less than 20% of cells showed uptake of siRNA mediated by KL4. As the PEG chain length increased, the cellular uptake increased, with over 90% of cellular uptake observed in $PEG_{12}KL4$ and $PEG_{24}KL4$ peptide. Both of these peptides performed significantly better than KL4 and $PEG_6KL4$ in terms of siRNA uptake on A549 cells. The median fluorescence intensity of cells also followed the same trend. Compared to A549 cells, Calu-3 cells were harder to transfect, and the difference of the peptides could not be reflected on this cell line as no significant difference was observed among them, with around 30% to 40% of cellular uptake achieved.

Inflammatory Response In Vivo

The inflammatory responses of KL4/siRNA and $PEG_{12}KL4$/siRNA complexes were investigated in mice following intratracheal administration by measuring the level of pro-inflammatory cytokines in BALF and lung homogenates (FIGS. 30A-30B). The expressions of TNF-alpha, IL-6, MCP-1 and KC were significantly induced by LPS in both BALF and lung homogenates but not affected by $PEG_{12}KL4$/siRNA. KL4/siRNA significantly induced the expression of MCP-1 in both BALF and lung homogenates. The IL-6 level in BALF and KC level in lung homogenates were higher in the KL4/siRNA treated mice compared with the $PEG_{12}KL4$/siRNA treated mice. Moreover, the body weight of the mice was monitored before and at 24 h post-administration (FIG. 31). Both LPS and KL4/siRNA complexes resulted in more than 5% of weight loss after 24 h while $PEG_{12}KL4$/siRNA complexes did not cause significant weight change of the mice.

9.4 Discussion

PEGylation is a common strategy used in the modification of therapeutic proteins, peptides, nucleic acids, as well as delivery systems including liposomes and polymers to improve their physicochemical and/or pharmacokinetic properties [67, 68]. PEG is a versatile polymer with high aqueous solubility, biocompatibility and structural flexibility. These desirable properties enable PEG and its derivatives to be widely used in pharmaceutical applications such as solubilizers, permeation enhancers, drug delivery systems and tissue scaffold in regenerative medicine [69]. In this study, the primary purpose of modifying KL4 peptide with PEG is to enhance peptide solubility. PEG length of 12 monomers or above was found to be effective in improving the solubility of KL4 peptide. However, it is anticipated that the presence of electrically neutral and hydrophilic PEG might provide steric hindrance and hamper the interaction between KL4 peptide and siRNA. As demonstrated in the fluorescence displacement assay, PEGylated KL4 peptides were in fact more effective in displacing the dye from the siRNA/dye mixture. KL4 peptide was inferior to other peptides in interacting with siRNA, possibly due to its self-aggregating property. As shown in the TEM images, KL4 peptide self-assembled into nanofiber structure with a length of over 500 nm (FIG. 32). Other □-helix and □-sheet based self-assembling peptides have been reported to form nanofibers with morphology similar to KL4 peptide [70, 71]. The relatively low CD values for KL4 peptide compared with other PEGylated KL4 peptides were consistent with the TEM image, as much of the KL4 peptide was self-aggregated and was no longer in solution. After PEGylation, the peptides became more hydrophilic overall and were no longer aggregated, allowing siRNA to gain access to the binding site of the peptide more efficiently. The presence of PEG may provide steric hindrance to promote the release of dye from siRNA/dye mixture, leading to a sharp decrease of fluorescence intensity at low ratios. Similar observation was shown in another study in which PEGylated polymer increased dye displacement from the DNA/dye mixture compared with non-PEGylated polymer due to the local crowding of the PEG chains [72]. After PEGylation, the peptides generally adopted alpha-helical conformation, which was crucial for efficient siRNA transfection [73]. However, they responded quite differently to the change of temperature. There was no agreement on the effect of PEGylation on the conformational stability of proteins and peptides in the literature. Some studies reported that PEGylation had no effect on secondary structure while some claimed that the PEGylation can increase or decrease the conformation stability [74-76].

The siRNA release study by the addition of heparin suggested that the strength of interaction between peptides and siRNA becomes weaker as PEG length increases. This is partly because the uncharged PEG chains reduced the effective charge ratio between cationic KL4 and siRNA [77]. The charge ratios of KL4, $PEG_6KL4$, $PEG_{12}KL4$ and $PEG_{24}KL4$ to siRNA at 10:1 weight ratio are 6.1 to 1, 5.5 to 1, 4.9 to 1 and 4.2 to 1, respectively. Consistently, the zeta potential of the PEGylated KL4/siRNA was significantly lower than that of the KL4/siRNA complexes, which suggested that the presence of PEG shielded some of the positive charges on the surface of the complexes. The molecular weight of the PEG used in this study, which is below 1,200 Da, is relatively low compared with others where PEG of 2,000 to 5,000 Da was often used [78-80]. Therefore, PEGylated KL4 peptide/siRNA complexes remained to be positively charged, which is suitable for cellular entry. The zeta potential of peptides with different PEG length was similar, indicating that the overall surface charge was not affected significantly by the length of the PEG. In addition, PEG also provides steric hindrance between the interaction of KL4 and siRNA that weakens the binding, promoting the release of siRNA from the complexes after the addition of heparin.

The stabilization of colloidal system can be achieved by two major mechanisms, steric repulsion and electrostatic repulsion [81]. After the addition of PBS, the size of the KL4/siRNA complexes increased significantly. The presence of counterions in the buffer neutralizes the surface charge [82], leading to the aggregation of particles as the electrostatic repulsion is weakened. As a result, the steric repulsion has become the dominant mechanism in providing colloidal stabilization. PEGylation is an effective way to stabilize particles [83] by providing colloidal stability through steric repulsion of particles and reduces nonspecific interactions, preventing aggregation of complexes [84, 85]. This explains why PEGylated KL4/siRNA complexes were less affected by the presence of physiological salt. The longer the PEG chain length, the smaller the particles, suggesting the length of the PEG chain has an impact on its ability to confer steric stabilization to the particles [84].

The physicochemical properties of the KL4 peptide are affected by PEGylation, which in turn affects the cellular uptake of the peptide/siRNA complexes. Flow cytometry study on A549 cells showed that cellular uptake increased when PEG chain length increased. The distinct cellular uptake percentage of different peptides was because of the improvement of colloidal stability of the PEGylated peptides in the physiological environment, resulting in the formulation of smaller particles for efficient cell entry. However, the trend of cellular uptake was not reflected by the flow cytometry result on Calu-3 cells. One of the possible reasons is the difference in uptake mechanism and cell layer barrier properties between A549 and Calu-3 cells. The internalization, intracellular trafficking and silencing efficiency of siRNA complexes are cell line dependent [86]. On A549 cells, the entry is mediated by both clathrin and caveolin pathways, while in Calu-3 cells, it is more dependent on the clathrin-mediated pathway. It is possible that the siRNA complexes of $PEG_{12}KL4$ and $PEG_{24}KL4$ were more effective in harnessing both clathrin and caveolin pathways, hence their uptake efficiency was significant higher than other complexes on A549 cells. However, the exact uptake mechanisms of PEGylated KL4 peptides in different cell lines remain to be investigated in future studies.

The effect of PEGylation on siRNA gene silencing efficiency was further evaluated on three different cells lines. Across all three cell lines, the transfection efficiency increased as the peptide to siRNA weight ratio increased and there was no significant difference between complexes formed at 10:1 and higher ratios for all PEGylated KL4 peptides. Therefore, to avoid the use of excessive peptides and reduce the risk of toxicity, the 10:1 ratio was chosen for other studies. The commercial transfection reagent lipofectamine 2000 inhibited more than 90% GAPDH expression on A549 cells but it failed to transfect effectively on BEAS-2B and Calu-3 cells, which are known to be difficult to transfect [87, 88]. Calu-3 cells can form monolayers with tight junctions and have secretory activities [89], making it hard to transfect. BEAS-2B cells were also reported to have tight junction but to a lesser extent [89, 90]. Moreover, as a non-cancerous cell line, it is not properly differentiated [91]. The slower rate of internalization and cell division contributes to low transfection in general. Unlike lipofectamine 2000, the transfection efficiency of the PEGylated KL4 peptides was less influenced by cell types with robust gene silencing effects observed in all cell lines used in this study.

To understand why the peptides mediated similar level of gene silencing despite the substantial difference in cellular uptake, A549 cells were transfected with different amount of siRNA. When the cells were transfected with 25 pmol of siRNA, only $PEG_6KL4$ and $PEG_{12}KL4$ peptides could achieve similar level of GAPDH knockdown to the cells transfected with 50 pmol of siRNA. The reduced amount of siRNA uptake was compensated by more efficient intracellular trafficking of these two PEGylated peptides. Among the four peptides, $PEG_{24}KL4$ peptide had the lowest transfection efficiency, which could be due to premature release of the siRNA as the binding affinity between $PEG_{24}KL4$ and siRNA was the weakest. It is crucial to optimize the length of PEG to maintain a good balance between the siRNA binding affinity, water solubility and steric stabilization effect.

The in vivo toxicity and inflammatory response of $PEG_{12}KL4$ peptide were evaluated. Although KL4 peptide did not induce cytotoxicity and inflammatory response in vitro [17], the immune system was activated and the weight of the mice was decreased when KL4/siRNA complexes were delivered to the lung of animal via intratracheal administration. It is well-established that PEGylation is an effective approach in suppressing immunogenicity and immunotoxicity by masking and shielding antigenic epitopes on proteins and peptides [92-94]. Our results demonstrated that the toxicity and inflammatory response were significantly improved after PEGylation as the delivery of $PEG_{12}KL4$/siRNA complexes did not cause any toxicity and inflammatory response in vivo.

9.5 Conclusions

This study investigated the effect of PEGylation on KL4 peptides for siRNA transfection. Three monodisperse PEG with different numbers of monomers were attached to KL4 peptide and compared. The increase of PEG chain length resulted in improved water solubility, better colloidal stability as well as higher cellular uptake of siRNA, but it also weakened the siRNA binding. Based on the in vitro studies, the water-soluble $PEG_{12}KL4$ peptide showed the optimal characteristics in delivering siRNA. It could bind with siRNA with desirable affinity and mediated robust transfection and efficient intracellular transportation, along with low risk of inflammatory response and toxicity in vivo following pulmonary administration. Overall, PEG$_{12}$KL4 has considerable potential to be developed as a non-viral vector for siRNA pulmonary delivery. Future studies will be focused on investigating the in vivo transfection efficiency of the PEG$_{12}$KL4 peptide following pulmonary administration.

REFERENCES

1. Sahin U, Kariko K, and Tureci O: *mRNA-based therapeutics—developing a new class of drugs*. Nat Rev Drug Discov 2014; 13(10): pp 759-80.
2. Wolff J A, Malone R W, Williams P, Chong W, Acsadi G, Jani A, and Felgner P L: *Direct gene transfer into mouse muscle in vivo*. Science 1990; 247(4949 Pt 1): pp 1465-8.
3. Jirikowski G F, Sanna P P, Maciejewski-Lenoir D, and Bloom F E: *Reversal of diabetes insipidus in Brattleboro rats: intrahypothalamic injection of vasopressin mRNA*. Science 1992; 255(5047): pp 996-8.
4. Uchida S, Kataoka K, and Itaka K: *Screening of mRNA Chemical Modification to Maximize Protein Expression with Reduced Immunogenicity*. Pharmaceutics 2015; 7(3): pp 137-51.
5. Holtkamp S, Kreiter S, Selmi A, Simon P, Koslowski M, Huber C, Tureci 0, and Sahin U: *Modification of antigen-encoding RNA increases stability, translational efficacy, and T-cell stimulatory capacity of dendritic cells*. Blood 2006; 108(13): pp 4009-17.
6. Sahu I, Haque A, Weidensee B, Weinmann P, and Kormann M S D: *Recent Developments in mRNA-Based Protein Supplementation Therapy to Target Lung Diseases*. Mol Ther 2019; 27(4): pp 803-823.
7. Mays L E, Ammon-Treiber S, Mothes B, Alkhaled M, Rottenberger J, Muller-Hermelink E S, Grimm M, Mezger M, Beer-Hammer S, von Stebut E, Rieber N, Nurnberg B, Schwab M, Handgretinger R, Idzko M, Hartl D, and Kormann M S: *Modified Foxp3 mRNA protects against asthma through an IL-10-dependent mechanism*. J Clin Invest 2013; 123(3): pp 1216-28.
8. Kormann M S, Hasenpusch G, Aneja M K, Nica G, Flemmer A W, Herber-Jonat S, Huppmann M, Mays L E, Illenyi M, Schams A, Griese M, Bittmann I, Handgretinger R, Hartl D, Rosenecker J, and Rudolph C: *Expression of therapeutic proteins after delivery of chemically modified mRNA in mice*. Nat Biotechnol 2011; 29(2): pp 154-7.
9. Chow M Y and Lam J K: *Dry Powder Formulation of Plasmid DNA and siRNA for Inhalation*. Curr Pharm Des 2015; 21(27): pp 3854-66.
10. Mitchell J and Nagel M: *Particle size analysis of aerosols from medicinal inhalers*. KONA Powder and Particle Journal 2004; 22: pp 32-65.
11. Malcolmson R J and Embleton J K: *Dry powder formulations for pulmonary delivery*. Pharmaceutical science & technology today 1998; 1(9): pp 394-398.
12. Chan H K: *Dry powder aerosol delivery systems: current and future research directions*. J Aerosol Med 2006; 19(1): pp 21-7.
13. Tavernier G, Andries O, Demeester J, Sanders N N, De Smedt S C, and Rejman J: *mRNA as gene therapeutic: how to control protein expression*. J Control Release 2011; 150(3): pp 238-47.
14. Johler S M, Rejman J, Guan S, and Rosenecker J: *Nebulisation of IVT mRNA Complexes for Intrapulmonary Administration*. PLoS One 2015; 10(9): ppe0137504.
15. Patel A K, Kaczmarek J C, Bose S, Kauffman K J, Mir F, Heartlein M W, DeRosa F, Langer R, and Anderson D G: *Inhaled Nanoformulated mRNA Polyplexes for Protein Production in Lung Epithelium*. Adv Mater 2019; 31(8): ppe1805116.
16. Robinson E, MacDonald K D, Slaughter K, McKinney M, Patel S, Sun C, and Sahay G: *Lipid Nanoparticle-Delivered Chemically Modified mRNA Restores Chloride Secretion in Cystic Fibrosis*. Mol Ther 2018; 26(8): pp 2034-2046.
17. Qiu Y, Chow M Y T, Liang W, Chung W W Y, Mak J C W, and Lam J K W: From Pulmonary Surfactant, Synthetic KL4 Peptide as Effective siRNA Delivery Vector for Pulmonary Delivery. Mol Pharm 2017; 14(12): pp 4606-4617.
18. Kinbara K: *Monodisperse engineered PEGs for bio-related applications*. Polymer Journal 2018; 50(8): pp 689.
19. Chow M Y T, Qiu Y, Lo F F K, Lin H H S, Chan H K, Kwok P C L, and Lam J K W: *Inhaled powder formulation of naked siRNA using spray drying technology with l-leucine as dispersion enhancer*. Int J Pharm 2017; 530(1-2): pp 40-52.
20. Liang W, Chow M Y T, Chow S F, Chan H K, Kwok P C L, and Lam J K W: *Using two-fluid nozzle for spray freeze drying to produce porous powder formulation of naked siRNA for inhalation*. Int J Pharm 2018; 552(1-2): pp 67-75.
21. The British Pharmacopoeia Commission Secretariat of the Medicines and Healthcare Products Regulatory Agency, *The British Pharmacopoeia* 2016. 2016, The Stationery Office.
22. Liao Q, Yip L, Chow M Y T, Chow S F, Chan H K, Kwok P C L, and Lam J K W: *Porous and highly dispersible voriconazole dry powders produced by spray freeze drying for pulmonary delivery with efficient lung deposition*. Int J Pharm 2019; 560: pp 144-154.
23. Guan S and Rosenecker J: *Nanotechnologies in delivery of mRNA therapeutics using nonviral vector-based delivery systems*. Gene therapy 2017; 24(3): pp 133.
24. Ito T, Okuda T, Takayama R, and Okamoto H: *Establishment of an Evaluation Method for Gene Silencing by Serial Pulmonary Administration of siRNA and pDNA Powders: Naked siRNA Inhalation Powder Suppresses Luciferase Gene Expression in the Lung*. J Pharm Sci 2019.
25. Asai-Tajiri Y, Matsumoto K, Fukuyama S, Kan-o K, Nakano T, Tonai K, Ohno T, Azuma M, Inoue H, and Nakanishi Y: *Small interfering RNA against CD86 during allergen challenge blocks experimental allergic asthma*. Respiratory research 2014; 15(1): pp 132.
26. Goh F Y, Cook K L, Upton N, Tao L, Lah L C, Leung B P, and Wong W F: *Receptor-interacting protein 2 gene silencing attenuates allergic airway inflammation*. The Journal of Immunology 2013; 191(5): pp 2691-2699.
27. Miwata K, Okamoto H, Nakashima T, Ihara D, Horimasu Y, Masuda T, Miyamoto S, Iwamoto H, Fujitaka K, and Hamada H: *Intratracheal Administration of siRNA Dry Powder Targeting Vascular Endothelial Growth Factor Inhibits Lung Tumor Growth in Mice*. Molecular Therapy-Nucleic Acids 2018; 12: pp 698-706.
28. Agnoletti M, Bohr A, Thanki K, Wan F, Zeng X, Boetker J P, Yang M, and Foged C: *Inhalable siRNA-loaded nano-embedded microparticles engineered using microfluidics and spray drying*. European Journal of Pharmaceutics and Biopharmaceutics 2017; 120: pp 9-21.
29. Sebastian M, Papachristofilou A, Weiss C, Fruh M, Cathomas R, Hilbe W, Wehler T, Rippin G, Koch S D, Scheel B, Fotin-Mleczek M, Heidenreich R, Kallen K J, Gnad-Vogt U, and Zippelius A: *Phase Ib study evaluating a self-adjuvanted mRNA cancer vaccine (RNActive(R)) combined with local radiation as consolidation and maintenance treatment for patients with stage IV non-small cell lung cancer*. BMC Cancer 2014; 14: pp 748.

30. Bahl K, Senn J J, Yuzhakov O, Bulychev A, Brito L A, Hassett K J, Laska M E, Smith M, Almarsson O, Thompson J, Ribeiro A M, Watson M, Zaks T, and Ciaramella G: *Preclinical and Clinical Demonstration of Immunogenicity by mRNA Vaccines against H10N8 and H7N9 Influenza Viruses*. Mol Ther 2017; 25(6): pp 1316-1327.

31. D'Souza A A and Shegokar R: *Polyethylene glycol (PEG): a versatile polymer for pharmaceutical applications*. Expert Opin Drug Deliv 2016; 13(9): pp 1257-75.

32. Osman G, Rodriguez J, Chan S Y, Chisholm J, Duncan G, Kim N, Tatler A L, Shakesheff K M, Hanes J, Suk J S, and Dixon J E: *PEGylated enhanced cell penetrating peptide nanoparticles for lung gene therapy*. J Control Release 2018; 285: pp 35-45.

33. Huckaby J T and Lai S K: *PEGylation for enhancing nanoparticle diffusion in mucus*. Adv Drug Deliv Rev 2018; 124: pp 125-139.

34. Okuda T, Morishita M, Mizutani K, Shibayama A, Okazaki M, and Okamoto H: *Development of spray-freeze-dried siRNA/PEI powder for inhalation with high aerosol performance and strong pulmonary gene silencing activity*. J Control Release 2018; 279: pp 99-113.

35. Wu J, Wu L, Wan F, Rantanen J, Cun D, and Yang M: *Effect of thermal and shear stresses in the spray drying process on the stability of siRNA dry powders*. Int J Pharm 2019; 566: pp 32-39.

36. Liu B and Zhou X: *Freeze-drying of proteins*. Methods Mol Biol 2015; 1257: pp 459-76.

37. Maa Y F, Nguyen P A, Sweeney T, Shire S J, and Hsu C C: *Protein inhalation powders: spray drying vs spray freeze drying*. Pharm Res 1999; 16(2): pp 249-54.

38. Farkas D R, Hindle M, and Longest P W: *Characterization of a New High-Dose Dry Powder Inhaler (DPI) Based on a Fluidized Bed Design*. Ann Biomed Eng 2015; 43(11): pp 2804-15.

39. Sanders N, Rudolph C, Braeckmans K, De Smedt S C, and Demeester J: *Extracellular barriers in respiratory gene therapy*. Advanced drug delivery reviews 2009; 61(2): pp 115-127.

40. Price D N, Kunda N K, and Muttil P: *Challenges Associated with the Pulmonary Delivery of Therapeutic Dry Powders for Preclinical Testing*. KONA Powder and Particle Journal 2019; 36: pp 129-144.

41. Fire, A., et al., Potent and specific genetic interference by double-stranded RNA in *Caenorhabditis elegans*. Nature, 1998. 391(6669): p. 806-11.

42. Adams, D., et al., Patisiran, an RNAi Therapeutic, for Hereditary Transthyretin Amyloidosis. N Engl J Med, 2018. 379(1): p. 11-21.

43. Ruger, J., et al., Oligonucleotides to the (Gene) Rescue: FDA Approvals 2017-2019. Trends Pharmacol Sci, 2020. 41(1): p. 27-41.

44. Scott, L. J., Givosiran: First Approval. Drugs, 2020.

45. de Paula Brandao, P. R., S. S. Titze-de-Almeida, and R. Titze-de-Almeida, Leading RNA Interference Therapeutics Part 2: Silencing Delta-Aminolevulinic Acid Synthase 1, with a Focus on Givosiran. Mol Diagn Ther, 2020. 24(1): p. 61-68.

46. Garbuzenko, O. B., et al., Strategy to enhance lung cancer treatment by five essential elements: inhalation delivery, nanotechnology, tumor-receptor targeting, chemo- and gene therapy. Theranostics, 2019. 9(26): p. 8362-8376.

47. Choi, M., et al., Targeted delivery of Chil3/Chil4 siRNA to alveolar macrophages using ternary complexes composed of HMG and oligoarginine micelles. Nanoscale, 2020. 12(2): p. 933-943.

48. Park, A. M., et al., Heat Shock Protein 27 Plays a Pivotal Role in Myofibroblast Differentiation and in the Development of Bleomycin-Induced Pulmonary Fibrosis. PLoS One, 2016. 11(2): p. e0148998.

49. Bohr, A., et al., Anti-Inflammatory Effect of Anti-TNF-alpha SiRNA Cationic Phosphorus Dendrimer Nanocomplexes Administered Intranasally in a Murine Acute Lung Injury Model. Biomacromolecules, 2017. 18(8): p. 2379-2388.

50. Merckx, P., et al., Surfactant protein B (SP-B) enhances the cellular siRNA delivery of proteolipid coated nanogels for inhalation therapy. Acta Biomater, 2018. 78: p. 236-246.

51. Nucci, M. L., R. Shorr, and A. Abuchowski, The therapeutic value of poly (ethylene glycol)-modified proteins. Advanced drug delivery reviews, 1991. 6(2): p. 133-151.

52. Bhadra, D., et al., Pegnology: a review of PEG-ylated systems. Die Pharmazie, 2002. 57(1): p. 5-29.

53. Harris, J. M. and R. B. Chess, Effect of pegylation on pharmaceuticals. Nature reviews Drug discovery, 2003. 2(3): p. 214-221.

54. Luo, T., et al., PEGylation of paclitaxel largely improves its safety and anti-tumor efficacy following pulmonary delivery in a mouse model of lung carcinoma. J Control Release, 2016. 239: p. 62-71.

55. Aldayel, A. M., et al., Lipid nanoparticles with minimum burst release of TNF-α siRNA show strong activity against rheumatoid arthritis unresponsive to methotrexate. Journal of Controlled Release, 2018. 283: p. 280-289.

56. Malhotra, M., et al., Development and characterization of chitosan-PEG-TAT nanoparticles for the intracellular delivery of siRNA. International journal of nanomedicine, 2013. 8: p. 2041.

57. Aldrian, G., et al., PEGylation rate influences peptide-based nanoparticles mediated siRNA delivery in vitro and in vivo. Journal of Controlled Release, 2017. 256: p. 79-91.

58. Lechanteur, A., et al., PEGylation of lipoplexes: The right balance between cytotoxicity and siRNA effectiveness. European Journal of Pharmaceutical Sciences, 2016. 93: p. 493-503.

59. Mao, S., et al., Influence of polyethylene glycol chain length on the physicochemical and biological properties of poly (ethylene imine)-graft-poly (ethylene glycol) block copolymer/SiRNA polyplexes. Bioconjugate chemistry, 2006. 17(5): p. 1209-1218.

60. Santiwarangkool, S., et al., PEGylation of the GALA peptide enhances the lung-targeting activity of nanocarriers that contain encapsulated siRNA. Journal of pharmaceutical sciences, 2017. 106(9): p. 2420-2427.

61. Kinbara, K., Monodisperse engineered PEGs for biorelated applications. Polymer Journal, 2018. 50(8): p. 689-697.

62. Gaziova, Z., et al., Chemically defined polyethylene glycol siRNA conjugates with enhanced gene silencing effect. Bioorg Med Chem, 2014. 22(7): p. 2320-6.

63. Dohmen, C., et al., Defined Folate-PEG-siRNA Conjugates for Receptor-specific Gene Silencing. Mol Ther Nucleic Acids, 2012. 1: p. e7.

64. Zhang, C. Y., et al., Native chemical ligation for conversion of sequence-defined oligomers into targeted pDNA and siRNA carriers. J Control Release, 2014. 180: p. 42-50.

65. He, D., et al., Combinatorial Optimization of Sequence-Defined Oligo(ethanamino)amides for Folate Receptor-Targeted pDNA and siRNA Delivery. Bioconjug Chem, 2016. 27(3): p. 647-59.

66. Liang, W., et al., Inhalable dry powder formulations of siRNA and pH-responsive peptides with antiviral activity against H1N1 influenza virus. Mol Pharm, 2015. 12(3): p. 910-21.

67. Suk, J. S., et al., PEGylation as a strategy for improving nanoparticle-based drug and gene delivery. Adv Drug Deliv Rev, 2016. 99(Pt A): p. 28-51.

68. Milla, P., F. Dosio, and L. Cattel, PEGylation of proteins and liposomes: a powerful and flexible strategy to improve the drug delivery. Curr Drug Metab, 2012. 13(1): p. 105-19.

69. D'Souza A, A. and R. Shegokar, Polyethylene glycol (PEG): a versatile polymer for pharmaceutical applications. Expert Opin Drug Deliv, 2016. 13(9): p. 1257-75.

70. Bakota, E. L., et al., Self-assembling multidomain peptide fibers with aromatic cores. Biomacromolecules, 2013. 14(5): p. 1370-8.

71. Wu, Y., et al., A Supramolecular Vaccine Platform Based on alpha-Helical Peptide Nanofibers. ACS Biomater Sci Eng, 2017. 3(12): p. 3128-3132.

72. Deshpande, M. C., et al., Influence of polymer architecture on the structure of complexes formed by PEG-tertiary amine methacrylate copolymers and phosphorothioate oligonucleotide. J Control Release, 2002. 81(1-2): p. 185-99.

73. Qiu, Y., et al., Modification of KL4 Peptide Revealed the Importance of Alpha-Helical Structure for Efficient Small Interfering RNA Delivery. Nucleic Acid Ther, 2020.

74. Rodriguez-Martinez, J. A., et al., Stabilization of alpha-chymotrypsin upon PEGylation correlates with reduced structural dynamics. Biotechnol Bioeng, 2008. 101(6): p. 1142-9.

75. Lawrence, P. B. and J. L. Price, How PEGylation influences protein conformational stability. Curr Opin Chem Biol, 2016. 34: p. 88-94.

76. Plesner, B., et al., Effects of PEG size on structure, function and stability of PEGylated BSA. Eur J Pharm Biopharm, 2011. 79(2): p. 399-405.

77. Merkel, O. M., et al., Nonviral siRNA delivery to the lung: investigation of PEG-PEI polyplexes and their in vivo performance. Mol Pharm, 2009. 6(4): p. 1246-60.

78. Yan, Y., et al., Aerosol delivery of stabilized polyester-siRNA nanoparticles to silence gene expression in orthotopic lung tumors. Biomaterials, 2017. 118: p. 84-93.

79. Feldmann, D. P., et al., The impact of microfluidic mixing of triblock micelleplexes on in vitro/in vivo gene silencing and intracellular trafficking. Nanotechnology, 2017. 28(22): p. 224001.

80. Kanehira, Y., et al., Intratumoral delivery and therapeutic efficacy of nanoparticle-encapsulated anti-tumor siRNA following intrapulmonary administration for potential treatment of lung cancer. Pharm Dev Technol, 2019. 24(9): p. 1095-1103.

81. M. G. Ivanov, D. M. I., Chapter 14—Nanodiamond Nanoparticles as Additives to Lubricants, in Ultrananocrystalline Diamond: Synthesis, Properties, and Applications, D. M. G. Olga A. Shenderova, Editor. 2012, William Andrew.

82. Brown, M. A., A. Goel, and Z. Abbas, Effect of Electrolyte Concentration on the Stern Layer Thickness at a Charged Interface. Angew Chem Int Ed Engl, 2016. 55(11): p. 3790-4.

83. Mishra, S., P. Webster, and M. E. Davis, PEGylation significantly affects cellular uptake and intracellular trafficking of non-viral gene delivery particles. Eur J Cell Biol, 2004. 83(3): p. 97-111.

84. Bartlett, D. W. and M. E. Davis, Physicochemical and biological characterization of targeted, nucleic acid-containing nanoparticles. Bioconjug Chem, 2007. 18(2): p. 456-68.

85. O'Mahony, A. M., et al., Cationic and PEGylated Amphiphilic Cyclodextrins: Co-Formulation Opportunities for Neuronal Sirna Delivery. PLoS One, 2013. 8(6): p. e66413.

86. Capel, V., et al., Insight into the relationship between the cell culture model, cell trafficking and siRNA silencing efficiency. Biochem Biophys Res Commun, 2016. 477(2): p. 260-5.

87. Danilkovitch-Miagkova, A., et al., Hyaluronidase 2 negatively regulates RON receptor tyrosine kinase and mediates transformation of epithelial cells by jaagsiekte sheep retrovirus. Proc Natl Acad Sci USA, 2003. 100(8): p. 4580-5.

88. Ramachandran, S., et al., Efficient delivery of RNA interference oligonucleotides to polarized airway epithelia in vitro. Am J Physiol Lung Cell Mol Physiol, 2013. 305(1): p. L23-32.

89. Stewart, C. E., et al., Evaluation of differentiated human bronchial epithelial cell culture systems for asthma research. J Allergy (Cairo), 2012. 2012: p. 943982.

90. Noah, T. L., et al., Tight junctions and mucin mRNA in BEAS-2B cells. In Vitro Cell Dev Biol Anim, 1995. 31(10): p. 738-40.

91. Ghio, A. J., et al., Growth of human bronchial epithelial cells at an air-liquid interface alters the response to particle exposure. Part Fibre Toxicol, 2013. 10: p. 25.

92. Veronese, F. M. and A. Mero, The impact of PEGylation on biological therapies. BioDrugs, 2008. 22(5): p. 315-29.

93. Zheng, J. C., et al., PEGylation is effective in reducing immunogenicity, immunotoxicity, and hepatotoxicity of alpha-momorcharin in vivo. Immunopharmacol Immunotoxicol, 2012. 34(5): p. 866-73.

94. Xu, Y., et al., Structure-based antigenic epitope and PEGylation improve the efficacy of staphylokinase. Microb Cell Fact, 2017. 16(1): p. 197.

The foregoing description of the specific embodiments will so fully reveal the general nature of the disclosure that others can, by applying knowledge within the skill of the relevant art(s) (including the contents of the documents cited and incorporated by reference herein), readily modify and/or adapt for various applications such specific embodiments, without undue experimentation, without departing from the general concept of the present disclosure. Such adaptations and modifications are therefore intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s).

While various embodiments of the present disclosure have been described above, it should be understood that they have been presented by way of examples, and not limitation. It would be apparent to one skilled in the relevant art(s) that various changes in form and detail could be made therein without departing from the spirit and scope of the disclosure.

Thus, the present disclosure should not be limited by any of the above-described exemplary embodiments, but should be defined only in accordance with the following claims and their equivalents.

The invention claimed is:

1. A complex comprising a pegylated peptide comprising a cationic KL4 peptide and a monodisperse linear PEG comprising 6-24 units, which peptide is PEG$_{6-24}$KL4; and a nucleic acid selected from the group consisting of an mRNA, an siRNA and a DNA.

2. The complex of claim 1 wherein the peptide comprises 6 PEG units, 12 PEG units, or 24 PEG units, which peptide is PEG$_6$KL4, PEG$_{12}$KL4 or PEG$_{24}$KL4, respectively.

3. The complex of claim 1 comprising a PEG$_{6-24}$KL4 peptide and an mRNA.

4. The complex of claim 3 wherein the peptide is PEG$_{12}$KL4.

5. The complex of claim 4 wherein the ratio of PEG$_{12}$KL4 to mRNA is 10:1, 15:1, or 20:1.

6. A composition comprising the complex of claim 3 and a bulking agent.

7. The composition of claim 6 wherein the bulking agent is mannitol.

8. The composition of claim 6 which is in a dry powder formulation.

9. The composition of claim 8 where the dry powder formulation has a powder size of about 5 μm.

10. The composition of claim 8 wherein the powder has a dispersion property of a fine particle fraction that is >40% in a cascade impactor study.

11. The complex of claim 1 comprising a PEG$_{6-24}$KL4 peptide and an siRNA.

12. The complex of claim 11 wherein the peptide is PEG$_{12}$KL4.

13. The complex of claim 12 wherein the ratio of PEG$_{12}$KL4 to siRNA is 10:1, 15:1, or 20:1.

14. The complex of claim 1 comprising a PEG$_{6-24}$KL4 peptide and a DNA.

15. The complex of claim 14 wherein the peptide is PEG$_{12}$KL4.

16. The complex of claim 15 wherein the ratio of PEG$_{12}$KL4 to DNA is 10:1, 15:1, or 20:1.

17. A method of treating a lung disease or providing vaccination, said method comprising the step of administering the complex of claim 1 via inhalation or nasal administration.

18. The method of claim 17 wherein the complex is delivered to lung epithelial cells of the subject.

19. The method of claim 17 wherein the lung disease is cystic fibrosis or lung inflammatory diseases.

20. The method of claim 17 wherein the vaccination is against influenza.

* * * * *

```
                            SEQUENCE LISTING

<160> NUMBER OF SEQ ID NOS: 5

<210> SEQ ID NO 1
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Leu Leu Leu Leu Lys Leu Leu Leu Leu Lys Leu Leu Leu Leu Lys
1               5                   10                  15

Leu Leu Leu Leu Lys
            20

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Leu Leu Leu Leu
1               5

<210> SEQ ID NO 3
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Leu Leu Leu Leu Lys Leu Leu Leu Leu Lys Leu Leu Leu Leu Lys
1               5                   10                  15

Leu Leu Leu Leu Lys
            20

<210> SEQ ID NO 4
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Lys Leu Leu Leu Leu Lys Leu Leu Leu Leu Lys Leu Leu Leu Leu Lys
1               5                   10                  15

Leu Leu Leu Leu Lys
            20

<210> SEQ ID NO 5
<211> LENGTH: 21
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 5

Lys Leu Leu Leu Leu Lys Leu Leu Leu Leu Lys Leu Leu Leu Leu Lys
1               5                   10                  15

Leu Leu Leu Leu Lys
            20